US011160810B2

(12) United States Patent
McKinnell et al.

(10) Patent No.: US 11,160,810 B2
(45) Date of Patent: Nov. 2, 2021

(54) FUSED IMIDAZO-PIPERIDINE JAK INHIBITOR COMPOUND

(71) Applicant: THERAVANCE BIOPHARMA R&D IP, LLC, South San Francisco, CA (US)

(72) Inventors: Robert Murray McKinnell, Millbrae, CA (US); Venkat R. Thalladi, Foster City, CA (US); Hao Zhang, Foster City, CA (US); Paul R. Fatheree, San Francisco, CA (US); Lan Jiang, Foster City, CA (US); Marta Dabros, Foster City, CA (US); Jerry Nzerem, South San Francisco, CA (US)

(73) Assignee: Theravance Biopharma R&D IP, LLC, South San Francisco, CA (US)

(*) Notice: Subject to any disclaimer, the term of this patent is extended or adjusted under 35 U.S.C. 154(b) by 228 days.

(21) Appl. No.: 16/656,940

(22) Filed: Oct. 18, 2019

(65) Prior Publication Data
US 2020/0046719 A1    Feb. 13, 2020

Related U.S. Application Data

(62) Division of application No. 15/966,467, filed on Apr. 30, 2018, now Pat. No. 10,493,077.

(60) Provisional application No. 62/492,574, filed on May 1, 2017.

(51) Int. Cl.
| *A61K 31/5377* | (2006.01) |
| *A61K 9/10* | (2006.01) |
| *A61K 9/00* | (2006.01) |
| *A61P 29/00* | (2006.01) |
| *A61P 11/08* | (2006.01) |
| *A61P 17/04* | (2006.01) |
| *A61P 27/02* | (2006.01) |
| *A61P 11/06* | (2006.01) |
| *C07D 471/04* | (2006.01) |
| *A61P 11/00* | (2006.01) |
| *A61P 17/00* | (2006.01) |

(52) U.S. Cl.
CPC ........ *A61K 31/5377* (2013.01); *A61K 9/0019* (2013.01); *A61K 9/0048* (2013.01); *A61K 9/10* (2013.01); *A61P 11/00* (2018.01); *A61P 11/06* (2018.01); *A61P 11/08* (2018.01); *A61P 17/00* (2018.01); *A61P 17/04* (2018.01); *A61P 27/02* (2018.01); *A61P 29/00* (2018.01); *C07D 471/04* (2013.01)

(58) Field of Classification Search
CPC .................................................. A61K 31/5377
See application file for complete search history.

(56) References Cited

U.S. PATENT DOCUMENTS

| 6,534,524 | B1 | 3/2003 | Kania et al. |
| 6,884,890 | B2 | 4/2005 | Kania et al. |
| 7,884,109 | B2 | 2/2011 | Ohlmeyer et al. |
| 8,450,340 | B2 | 5/2013 | Hood et al. |
| 8,575,336 | B2 | 11/2013 | Coe et al. |
| 8,648,069 | B2 | 2/2014 | Akritopoulou-Zanze |
| 8,895,544 | B2 | 11/2014 | Coe et al. |
| 10,100,049 | B2 | 10/2018 | Fatheree et al. |
| 10,183,942 | B2 | 1/2019 | Benjamin et al. |
| 10,196,393 | B2 | 2/2019 | Fatheree et al. |
| 10,208,040 | B2 | 2/2019 | Fatheree et al. |
| 10,251,874 | B2 | 4/2019 | Dabros et al. |
| 10,392,386 | B2 | 8/2019 | Fatheree et al. |
| 10,406,148 | B2 | 9/2019 | Thalladi et al. |
| 2005/0090529 | A1 | 4/2005 | McAlpine et al. |
| 2015/0158864 | A1 | 6/2015 | Thorarensen et al. |
| 2015/0329542 | A1 | 11/2015 | Coe et al. |
| 2016/0289196 | A1 | 10/2016 | Choi et al. |
| 2018/0311255 | A1 | 11/2018 | Fatheree et al. |
| 2019/0106420 | A1 | 4/2019 | Fatheree et al. |

(Continued)

FOREIGN PATENT DOCUMENTS

| JP | 2010111624 A | 5/2010 |
| WO | 2005009389 A2 | 2/2005 |

(Continued)

OTHER PUBLICATIONS

Yano et al., "Ipilimumab augments antitumor activity of bispecific antibody-armed T cells", Journal of Translational Medicine, 12: 191 (2014).
Zeiser et al., "Ruxolitinib in corticosteroid-refractory graft-versus-host disease after allogeneic stem cell transplantation: a multi-center survey", Leukemia, 29(10): 2062-2068 (Oct. 2015).
Zhou et al., "Cytokines and Behcet's Disease", Autoimmunity Reviews, 11: 699-704 (2012).

(Continued)

*Primary Examiner* — Karen Cheng
(74) *Attorney, Agent, or Firm* — Jeffrey A. Hagenah; Florence Jovic

(57) ABSTRACT

The invention provides a compound of formula 1 or a pharmaceutically-acceptable salt thereof, that is useful as a JAK inhibitor. The invention also provides crystalline forms of the compound, pharmaceutical compositions comprising the compound, methods of using the compound to treat diseases amenable to a JAK inhibitor, and processes and intermediates useful for preparing the compound.

27 Claims, 5 Drawing Sheets

(56) References Cited

U.S. PATENT DOCUMENTS

| | | | |
|---|---|---|---|
| 2019/0127371 A1 | 5/2019 | Fatheree et al. | |
| 2019/0337945 A1 | 11/2019 | Fatheree et al. | |
| 2019/0350916 A1 | 11/2019 | Kleinschek et al. | |

FOREIGN PATENT DOCUMENTS

| | | |
|---|---|---|
| WO | 2010114971 A1 | 10/2010 |
| WO | 2013014567 A1 | 1/2013 |
| WO | 2015173683 A1 | 11/2015 |
| WO | 2016026078 A1 | 2/2016 |
| WO | 2017077283 A1 | 5/2017 |
| WO | 2017077288 A1 | 5/2017 |

OTHER PUBLICATIONS

PCT International Search Report for PCT/US2018/030148 dated Jul. 6, 2018).
Kudlacz et al., "The JAK-3 inhibitor CP-690550 is a potent anti-inflammatory agent in a murine model of pulmonary eosinophilia", European Journal of Pharmacology, 582:154-161 (2008).
Abcouwer, "Angiogenic factors and cytokines in diabetic retinopathy", J Clin Cell Immunol, Supplement 1: 1-12 (2013).
Bao et al., "The involvement of the JAK-STAT signaling pathway in chronic inflammatory skin disease atopic dermatitis", JAK-STAT, 2(3): e24137-1-e24137-8 (2013).
Berastegui et al., "BALF cytokines in different phenotypes of chronic lung allograft dysfunction in lung transplant patients". Clinical Transplantation, 31: e12898 (2017).
Coghill et al., "Effector CD4+ T cells, the cytokines they generate, and GVHD: something old and something new", Blood, 117(12): 3268-3276 (Mar. 24, 2011).
Cottin, "Eosinophilic lung diseases", Clin Chest Med, 37: 535-556 (2016).
Craiglow et al., "Tofacitinib citrate for the treatment of vitiligo: A pathogenesis-directed therapy", JAMA Dermatology, 151: 1110-1112 (2015).
De Nitto et al., "Involvement of interleukin-15 and interleukin-21, two gamma-chain-related cytokines, in celiac disease". World J Gastroenterol, 15(37): 4609-4614 (Oct. 7, 2009).
Del Amo et al., "Current and future ophthalmic drug delivery systems. A shift to the posterior segment", Drug Discovery Today, 13(3/4): 135-143 (Feb. 2008).
Deobhakta et al., "Inflammation in retinal vein occlusion", International Journal of Inflammation, vol. 2013, 6 pages (2013).
El-Hashemite et al., "Interferon-gamma-Jak-Stat signaling in pulmonary lymphangioleiomyomatosis and renal angiomyolipoma". Am J Respir Cell Mol Biol, 33: 227-230 (2005).
El-Hashemite et al., "Perturbed IFN-gamma-Jak-signal transducers and activators of transcription signaling in tuberous sclerosis mouse models: Synergistic effects of rapamycin-IFN-gamma treatment", Cancer Research, 64: 3436-3443 (May 15, 2004).
Fang et al., "Interleukin-6-572C/G polymorphism is associated with serum interleukin-6 levels and risk of idiopathic pulmonary arterial hypertension", Journal of the American Society of Hypertension, 11(3): 171-177 (2017).
Feliciani et al., "A TH2-like cytokine response is involved in bullous pemphigoid. The role of IL-4 and IL-5 in the pathogenesis of the disease", International Journal of Immunopathology and Pharmacology, 12(2): 55-61 (1999).
Fenwick et al., "Effect of JAK inhibitors on release of CXCL9, CXCL10 and CXCL11 from human airway epithelial cells", PLOS One, 10(6): e0128757 (2015).
Foloppe et al., "Identification of a buried pocket for potent and selective inhibition of Chk1: Prediction and verification", Bioorganic & Medicinal Chemistry, 14: 1792-1804 (2006).
Funatsu et al., "Association of vitreous inflammatory factors with diabetic macular edema", Ophthalmology, 116: 73-79 (2009).
Gauthier et al., "Update on chronic lung allograft dysfunction", Curr Transplant Rep, 3(3): 185-191 (Sep. 2016).
Graczyk, "Gini coefficient: a new way to express selectivity of kinase inhibitors against a family of kinases", J Med Chem, 50: 5773-5779 (2007).
Horai et al., "Cytokines in autoimmune uveitis", Journal of Interferon & Cytokine Research, 31(10): 733-744 (2011).
Huang et al., "Glycoprotein 130 inhibitor ameliorates monocrotalline-induced pulmonary hypertension in rats", Canadian Journal of Cardiology, 32: 1356.e1-1356.e10 (2016).
Jones et al., "Design and synthesis of a Pan-Janus kinase inhibitor clinical candidate (PF-06263276) suitable for inhaled and topical delivery for the treatment of inflammatory diseases of the lungs and skin", J. Med. Chem., 60: 767-786 (2017).
Knickelbein et al., "Inflammatory mechanisms of age-related macular degeneration", International Ophthalmology Clinics, 55(3): 63-78 (2015).
Kumawat et al., "Microscopic colitis patients demonstrate a mixed Th17/Tc17 and Th1/Tc1 mucosal cytokine profile", Molecular Immunology, 55: 355-364 (2013).
Kuno et al., "Recent advances in ocular drug delivery systems", Polymers, 3: 193-221 (2011).
Malaviya et al., "Janus Kinase-3 dependent inflammatory responses in allergic asthma", International Immunopharmacology, 10: 829-836 (2010).
Matsunaga et al., "Effects of a Janus kinase inhibitor, pyridone 6, on airway responses in a murine model of asthma", Biochemical and Biophysical Research Communications, 404: 261-267 (2011).
McBride et al., "Design and structure-activity relationship of 3-benzimidazol-2-yl-1H-indazoles as inhibitors of receptor tyrosine kinases", Bioorganic & Medicinal Chemistry Letters, 16: 3595-3599 (2006).
McBride et al., "3-Benzimidazol-2-yl-1H-indazoles as potent c-ABL inhibitors", Bioorganic & Medicinal Chemistry Letters, 16: 3789-3792 (2006).
Netchiporouk et al., "Deregulation in STAT signaling is important for cutaneous T-cell lymphoma (CTCL) pathogenesis and cancer progression", Cell Cycle, 13(21): 3331-3335 (Nov. 1, 2014).
Okiyama et al., "Reversal of CD8 T-cell-mediated mucocutaneous graft-versus-host-like disease by the JAK inhibitor tofacitinib", Journal of Investigative Dermatology, 134: 992-1000 (2014).
Owen et al., "Soluble mediators of diabetic macular edema: The diagnostic role of aqueous VEGF and cytokine levels in diabetic macular edema", Curr Diab Rep, 13(4): 476-480 (Aug. 2013).
Reimund et al., "Mucosal inflammatory cytokine production by intestinal biopsies in patients with ulcerative colitis and Crohn's disease", Journal of Clinical Immunology, 16(3): 144-150 (1996).
Shchuko et al., "Intraocular cytokines in retinal vein occlusion and its relation to the efficiency of anti-vascular endothelial growth factor therapy", Indian Journal of Ophthalmology, 63: 905-911 (2015).
Shino et al., "The prognostic importance of CXCR3 chemokine during organizing pneumonia on the risk of chronic lung allograft dysfunction after lung transplantation", PLOS One, 12(7): e0180281 (2017).
Short, "Safety evaluation of ocular drug delivery formulations: techniques and practical considerations", Toxicologic Pathology, 36: 49-62 (2008).
Simov et al., "Structure-based design and development of (benz)imidazole pyridones as JAK1-selective kinase inhibitors", Bioorganic & Medicinal Chemistry Letters, 26: 1803-1808 (2016).
Sohn et al., "Changes in aqueous concentrations of various cytokines after intravitreal triamcinolone versus bevacizumab for diabetic macular edema", Ophthalmology, 152: 686-694 (2011).
Sonkoly et al., "IL-31: A new link between T cells and pruritus in atopic skin inflammation", J Allergy Clin Immunol, 117(2): 411-417 (2006).
Stallmach et al., "Cytokine/chemokine transcript profiles reflect mucosal inflammation in Crohn's disease", Int J Colorectal Dis, 19: 308-315 (2004).
Stevenson et al., "Dry eye disease", Arch Ophthalmol, 130(1): 90-100 (Jan. 2012).
Tanaka et al., "New insight into mechanisms of pruritus from molecular studies on familial primary localized cutaneous amyloidosis", British Journal of Dermatology, 161: 1217-1224 (2009).

(56) References Cited

OTHER PUBLICATIONS

Trujillo et al., "2-(6-Phenyl-1H-indazol-3-yl)-1H-benzo[d]imidazoles: Design and synthesis of a potent and isoform selective PKC-zeta inhibitor", Bioorganic & Medicinal Chemistry Letters, 19: 908-911 (2009).
Vincenti et al., "Randomized phase 2b trial of tofacitinib (CP-690,550) in de novo kidney transplant patients: Efficacy, renal function and safety at 1 year", American Journal of Transplantation, 12: 2446-2456 (2012).
Weinbrand-Goichberg et al., "Eosinophilic esophagitis: an immune-mediated esophageal disease", Immunol Res, 56: 249-260 (2013).
Welz-Kubiak et al., "IL-31 is overexpressed in lichen planus but its level does not correlate with pruritus severity", Journal of Immunology Research, Article 854747, 6 pages (2015).
Woywodt et al., "Mucosal cytokine expression, cellular markers and adhesion molecules in inflammatory bowel disease", European Journal of Gastroenterology & Hepatology, 11: 267-276 (1999).
Xing et al., "Alopecia areata is driven by cytotoxic T lymphocytes and is reversed by JAK inhibition", Nature Medicine, 20(9): 1043-1049 (Sep. 2014).
Yamamoto et al., "Mucosal inflammation in the terminal ileum of ulcerative colitis patients: Endoscopic findings and cytokine profiles", Digestive and Liver Disease, 40: 253-259 (2008).
Yan et al., "Discovery of 3-(5'-Substituted)-benzimidazol-5-(1-(3,5-dichloropyridin-4-yl)ethoxy)-1H-indazoles as potent fibroblast growth factor receptor inhibitors: Design, synthesis, and biological evaluation", J. Med. Chem., 59: 6690-6708 (2016).

FUSED IMIDAZO-PIPERIDINE JAK INHIBITOR COMPOUND

CROSS-REFERENCE TO RELATED APPLICATIONS

This application is a division application of U.S. Ser. No. 15/966,467, filed on Apr. 30, 2018, now allowed, which application claims the benefit of U.S. Provisional Application No. 62/492,574, filed on May 1, 2017, the entire disclosures of which are incorporated herein by reference in their entirety.

BACKGROUND OF THE INVENTION

Field of the Invention

The invention is directed to a JAK kinase inhibitor compound useful for the treatment of multiple diseases, particularly ocular, skin, and respiratory diseases. The invention is also directed to crystalline forms of the compound, pharmaceutical compositions comprising such a compound, methods of using such a compound to treat diseases amenable to treatment with a JAK inhibitor, and processes and intermediates useful for preparing the compound.

State of the Art

Cytokines are intercellular signaling molecules which include chemokines, interferons, interleukins, lymphokines, and tumour necrosis factor. Cytokines are critical for normal cell growth and immunoregulation but also drive immune-mediated diseases and contribute to the growth of malignant cells. Elevated levels of many cytokines have been implicated in the pathology of a large number of diseases or conditions, particularly those diseases characterized by inflammation. Many of the cytokines implicated in disease act through signaling pathways dependent upon the Janus family of tyrosine kinases (JAKs), which signal through the Signal Transducer and Activator of Transcription (STAT) family of transcription factors.

The JAK family comprises four members, JAK1, JAK2, JAK3, and tyrosine kinase 2 (TYK2). Binding of cytokine to a JAK-dependent cytokine receptor induces receptor dimerization which results in phosphorylation of tyrosine residues on the JAK kinase, effecting JAK activation. Phosphorylated JAKs, in turn, bind and phosphorylate various STAT proteins which dimerize, internalize in the cell nucleus and directly modulate gene transcription, leading, among other effects, to the downstream effects associated with inflammatory disease. The JAKs usually associate with cytokine receptors in pairs as homodimers or heterodimers. Specific cytokines are associated with specific JAK pairings. Each of the four members of the JAK family is implicated in the signaling of at least one of the cytokines associated with inflammation.

Inflammation plays a prominent role in many ocular diseases, including uveitis, diabetic retinopathy, diabetic macular edema, dry eye disease, age-related macular degeneration, retinal vein occlusion and atopic keratoconjunctivitis. Uveitis encompasses multiple intraocular inflammatory conditions and is often autoimmune, arising without a known infectious trigger. The condition is estimated to affect about 2 million patients in the US. In some patients, the chronic inflammation associated with uveitis leads to tissue destruction, and it is the fifth leading cause of blindness in the US. Cytokines elevated in uveitis patients' eyes that signal through the JAK-STAT pathway include IL-2, IL-4, IL-4, 5, IL-6, IL-10, IL-23, and IFN-γ. (Horai and Caspi, *J Interferon Cytokine Res,* 2011, 31, 733-744; Ooi et al, *Clinical Medicine and Research,* 2006, 4, 294-309). Existing therapies for uveitis are often suboptimal, and many patients are poorly controlled. Steroids, while often effective, are associated with cataracts and increased intraocular pressure/glaucoma.

Diabetic retinopathy (DR) is caused by damage to the blood vessels in the retina. It is the most common cause of vision loss among people with diabetes. Angiogenic as well as inflammatory pathways play an important role in the disease. Often, DR will progress to diabetic macular edema (DME), the most frequent cause of visual loss in patients with diabetes. The condition is estimated to affect about 1.5 million patients in the US alone, of whom about 20% have disease affecting both eyes. Cytokines which signal through the JAK-STAT pathway, such as IL-6, as well as other cytokines, such as IP-10 and MCP-1 (alternatively termed CCL2), whose production is driven in part by JAK-STAT pathway signaling, are believed to play a role in the inflammation associated with DR/DME (Abcouwer, *J Clin Cell Immunol,* 2013, Suppl 1, 1-12; Sohn et al., *American Journal of Opthalmology,* 2011, 152, 686-694; Owen and Hartnett, *Curr Diab Rep,* 2013, 13, 476-480; Cheung et al, *Molecular Vision,* 2012, 18, 830-837; Dong et al, *Molecular Vision,* 2013, 19, 1734-1746; Funatsu et al, *Ophthalmology,* 2009, 116, 73-79). The existing therapies for DME are suboptimal: intravitreal anti-VEGF treatments are only effective in a fraction of patients and steroids are associated with cataracts and increased intraocular pressure.

Dry eye disease (DED) is a multifactorial disorder that affects approximately 5 million patients in the US. Ocular surface inflammation is believed to play an important role in the development and propagation of this disease. Elevated levels of cytokines such as IL-1, IL-2, IL-4, IL-5, IL-6, and IFN-γ have been noted in the ocular fluids of patients with DED. (Stevenson et al, *Arch Ophthalmol,* 2012, 130, 90-100), and the levels often correlated with disease severity. Age-related macular degeneration and atopic keratoconjunctivitis are also thought to be associated with JAK-dependent cytokines.

Retinal vein occlusion (RVO) is a highly prevalent visually disabling disease. Obstruction of retinal blood flow can lead to damage of the retinal vasculature, hemorrhage, and tissue ischemia. Although the causes for RVO are multifactorial, both vascular as well as inflammatory mediators have been shown to be important (Deobhakta et al, *International Journal of Inflammation,* 2013, article ID 438412). Cytokines which signal through the JAK-STAT pathway, such as IL-6 and IL-13, as well as other cytokines, such as MCP-1, whose production is driven in part by JAK-STAT pathway signaling, have been detected at elevated levels in ocular tissues of patients with RVO (Shchuko et al, *Indian Journal of Ophthalmology,* 2015, 63(12), 905-911). While many patients with RVO are treated by photocoagulation, this is an inherently destructive therapy. Anti-VEGF agents are also used, but they are only effective in a fraction of patients. Steroid medications that reduce the level of inflammation in the eye (Triamcinolone acetonide and dexamethasone implants) have also been shown to provide beneficial results for patients with certain forms of RVO, but they have also been shown to cause cataracts and increased intraocular pressure/glaucoma.

Atopic dermatitis (AD) is a common chronic inflammatory skin disease that affects an estimated 14 million people in the United States alone. It is estimated that AD affects 10-20% of children and 1-3% of adults in developed countries (Bao et al., *JAK-STAT,* 2013, 2, e24137) and the prevalence is increasing. Elevation of pro-inflammatory cytokines that rely on the JAK-STAT pathway, in particular, IL-4, IL-5, IL-10, IL-13, and IFNγ, have been associated with AD (Bao et al., Leung et al., *The Journal of Clinical Investigation,* 2004, 113, 651-657). In addition, upregulation of IL-31, another cytokine that signals through a JAK pairing, has been shown to have a role in the pruritis associated with the chronic state of AD. (Sunkoly et al., *Journal of Allergy and Clinical Immunology,* 2006, 117, 411-417)

Asthma is a chronic disease of the airways for which there are no preventions or cures. The disease is characterized by inflammation, fibrosis, hyperresponsiveness, and remodeling of the airways, all of which contribute to airflow limitation. An estimated 300 million people worldwide suffer from asthma and it is estimated that the number of people with asthma will grow by more than 100 million by 2025. Although most patients can achieve control of asthma symptoms with the use of inhaled corticosteroids that may be combined with a leukotriene modifier and/or a long acting beta agonist, there remains a subset of patients with severe asthma whose disease is not controlled by conventional therapies. Cytokines implicated in asthma inflammation which signal through the JAK-STAT pathway include IL-2, IL-3, IL-4, IL-5, IL-6, IL-9, IL-11, IL-13, IL-23, IL-31, IL-27, thymic stromal lymphopoietin (TSLP), interferon-γ (IFNγ) and granulocyte-macrophage colony-stimulating factor (GM-CSF). Inflammation of the airways is characteristic of other respiratory diseases in addition to asthma. Chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, bronchiolitis obliterans, and sarcoidosis are also respiratory tract diseases in which the pathophysiology is believed to be related to JAK-signaling cytokines.

Given the number of cytokines elevated in inflammatory diseases and that each cytokine is associated with a particular JAK pairing, a chemical inhibitor with pan-activity against all members of the JAK family could have broad utility for the treatment of ocular, skin, and respiratory disease. The need remains for a potent pan-JAK inhibitor.

SUMMARY OF THE INVENTION

In one aspect, the invention provides a JAK inhibitor compound useful for the treatment of inflammatory disease.

In particular, in one aspect, the invention provides 1-(2-(6-(2-ethyl-5-fluoro-4-hydroxyphenyl)-4-fluoro-1H-indazol-3-yl)-1,4,6,7-tetrahydro-5H-imidazo[4,5-c]pyridin-5-yl)-2-morpholinoethan-1-one of the formula

1

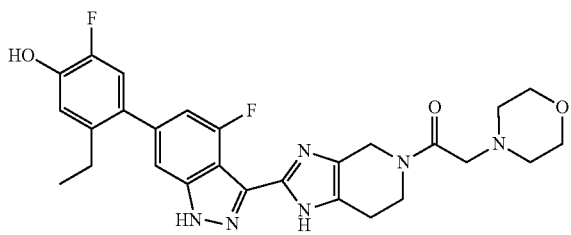

hereinafter compound 1, or a pharmaceutically-acceptable salt thereof.

The invention also provides crystalline forms of the compound, Form 1 and Form 2.

The invention also provides a pharmaceutical composition comprising compound 1, or a pharmaceutically acceptable salt thereof, and a pharmaceutically-acceptable carrier.

In one aspect, the invention provides a method of treating an ocular disease in a mammal, the method comprising administering to the mammal compound 1, or a pharmaceutical composition of the invention. In one aspect the ocular disease is uveitis, diabetic retinopathy, diabetic macular edema, dry eye disease, age-related macular degeneration, retinal vein occlusion and atopic keratoconjunctivitis. In particular, the ocular disease is diabetic macular edema or uveitis.

In yet another method aspect, the invention provides a method of treating an inflammatory disease of the skin, in particular atopic dermatitis, the method comprising applying compound 1, or a pharmaceutical composition of the invention to the skin of the mammal.

In a further aspect, the invention provides a method of treating a respiratory disease in a mammal, the method comprising administering compound 1, or a pharmaceutically-acceptable salt thereof or a pharmaceutical composition of the invention to the mammal.

In separate and distinct aspects, the invention also provides synthetic processes and intermediates described herein, which are useful for preparing compound 1.

The invention also provides compound 1 as described herein for use in medical therapy, as well as the use of the compound of the invention in the manufacture of a formulation or medicament for treating ocular disease, skin disease, or respiratory disease in a mammal.

BRIEF DESCRIPTION OF THE DRAWINGS

Various aspects of the present invention are illustrated by reference to the accompanying drawings.

DETAILED DESCRIPTION OF THE INVENTION

Figure 1:
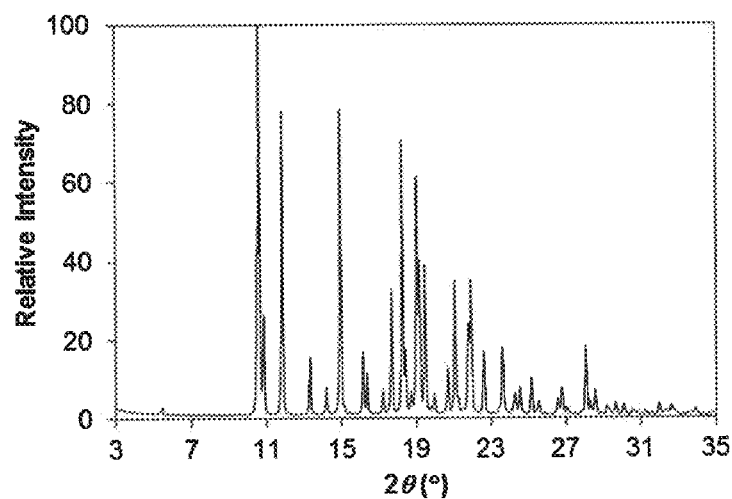
FIG. 1 shows a powder x-ray diffraction (PXRD) pattern of crystalline Form 2 of compound 1 (hereinafter Form 2).

Chemical structures are named herein according to IUPAC conventions as implemented in ChemDraw software (PerkinElmer, Inc., Cambridge, Mass.).

Furthermore, the imidazo portion of the tetrahydroimidazopyridine moiety in the structure of the present compound exists in tautomeric forms. The compound could equivalently be represented as

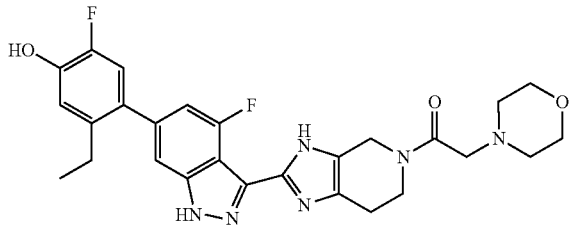 [SMILES: CCc1cc(O)c(F)cc1-c1cc(F)c2c(-c3nc4c([nH]3)CN(C(=O)CN3CCOCC3)CC4)n[nH]c2c1]

According to the IUPAC convention, these representations give rise to different numbering of the atoms of the tetrahydroimidazopyridine portion. Accordingly this structure is designated 1-(2-(6-(2-ethyl-5-fluoro-4-hydroxyphenyl)-4-fluoro-1H-indazol-3-yl)-3,4,6,7-tetrahydro-5H-imidazo[4,5-c]pyridin-5-yl)-2-morpholinoethan-1-one. It can also be designated 1-(2-(6-(2-ethyl-5-fluoro-4-hydroxyphenyl)-4-fluoro-1H-indazol-3-yl)-1,4,6,7-tetrahydro-5H-imidazo[4,5-c]pyridin-5-yl)-2-morpholinoethan-1-one. It will be understood that although structures are shown, or named, in a particular form, the invention also includes the tautomer thereof.

The compounds of the invention contain several basic groups and therefore, the compounds can exist as the free base or in various salt forms, such as a mono-protonated salt form, a di-protonated salt form, or mixtures thereof. All such forms are included within the scope of this invention, unless otherwise indicated.

This invention also includes isotopically-labeled compounds of formula 1, i.e., compounds of formula 1 where an atom has been replaced or enriched with an atom having the same atomic number but an atomic mass different from the atomic mass that predominates in nature. Examples of isotopes that may be incorporated into a compound of formula 1 include, but are not limited to, $^2H$, $^3H$, $^{11}C$, $^{13}C$, $^{14}C$, $^{13}N$, $^{15}N$, $^{15}O$, $^{17}O$, $^{18}O$, and $^{18}F$. Of particular interest are compounds of formula 1 enriched in tritium or carbon-14, which compounds can be used, for example, in tissue distribution studies. Also of particular interest are compounds of formula 1 enriched in deuterium especially at a site of metabolism, which compounds are expected to have greater metabolic stability.

Additionally of particular interest are compounds of formula 1 enriched in a positron emitting isotope, such as $^{11}C$, $^{18}F$, $^{15}O$ and $^{13}N$, which compounds can be used, for example, in Positron Emission Tomography (PET) studies.

Definitions

When describing this invention including its various aspects and embodiments, the follow The term "therapeutically effective amount" means an amount sufficient to effect treatment when administered to a patient in need of treatment.

The term "treating" or "treatment" means preventing, ameliorating or suppressing the medical condition, disease or disorder being treated (e.g., a respiratory disease) in a patient (particularly a human); or alleviating the symptoms of the medical condition, disease or disorder.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "salt thereof" means a compound formed when the hydrogen of an acid is replaced by a cation, such as a metal cation or an organic cation and the like. For example, the cation can be a protonated form of a compound of formula 1, i.e. a form where one or more amino groups have been protonated by an acid. Typically, the salt is a pharmaceutically acceptable salt, although this is not required for salts of intermediate compounds that are not intended for administration to a patient.

The term "amino-protecting group" means a protecting group suitable for preventing undesired reactions at an amino nitrogen. Representative amino-protecting groups include, but are not limited to, formyl; acyl groups, for example alkanoyl groups, such as acetyl and tri-fluoroacetyl; alkoxycarbonyl groups, such as tert butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS), tert-butyldimethylsilyl (TBDMS), [2-(trimethylsilyl)ethoxy]methyl (SEM); and the like.

The term "hydroxy-protecting group" means a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

Numerous protecting groups, and their introduction and removal, are described in T. W. Greene and P. G. M. Wuts, *Protecting Groups in Organic Synthesis*, Third Edition, Wiley, New York General Synthetic Procedures Compound 1, and intermediates thereof, can be prepared according to the following general methods and procedures using commercially-available or routinely-prepared starting materials and reagents. Additionally, compounds having an acidic or basic atom or functional group may be used or may be produced as a salt unless otherwise indicated (in some cases, the use of a salt in a particular reaction will require conversion of the salt to a non-salt form, e.g., a free base, using routine procedures before conducting the reaction).

Although a particular embodiment of the present invention may be shown or described in the following procedures, those skilled in the art will recognize that other embodiments or aspects of the present invention can also be prepared using such procedures or by using other methods, reagents, and starting materials know to those skilled in the art. In particular, it will be appreciated that compound 1 may be prepared by a variety of process routes in which reactants are combined in different orders to provide different intermediates en route to producing final products.

The preparation of 1-(2-(6-(2-ethyl-5-fluoro-4-hydroxyphenyl)-4-fluoro-1H-indazol-3-yl)-1,4,6,7-tetrahydro-5H-imidazo[4,5-c]pyridin-5-yl)-2-morpholinoethan-1-one (compound 1) is described in detail in the appended examples. Key steps are summarized in Scheme 1

Intermediate 3 may be prepared as described in Preparations 1 and 3 below. An alternative method of preparation of the key protected intermediate 5 is illustrated in Scheme 2.

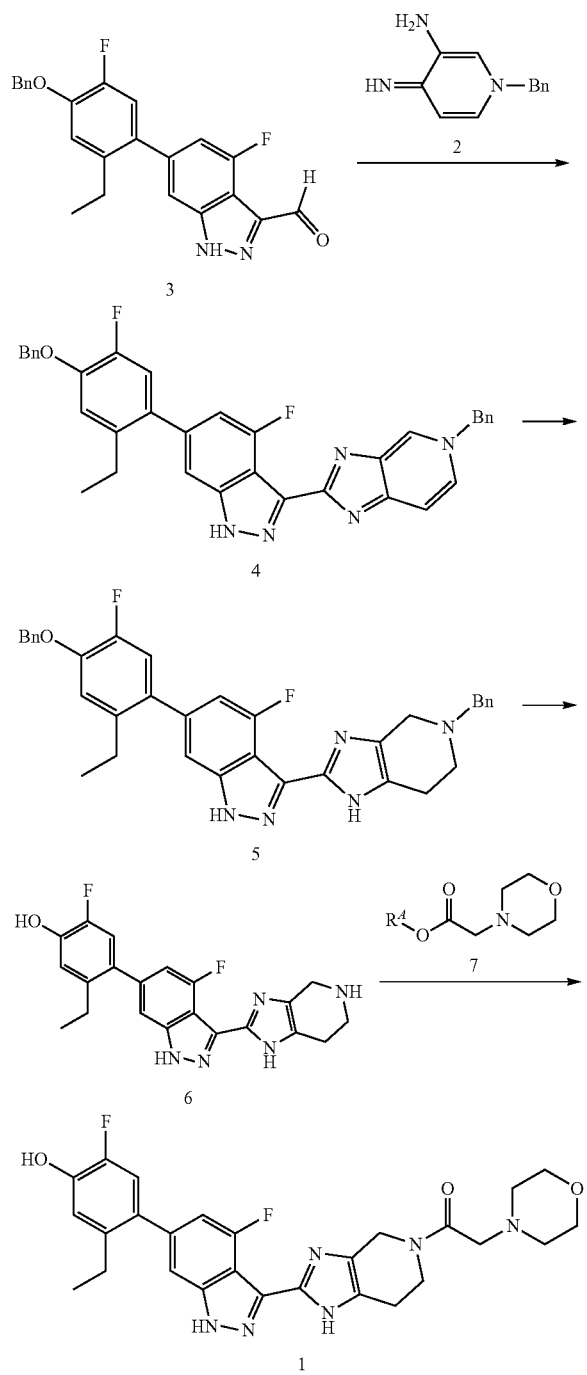

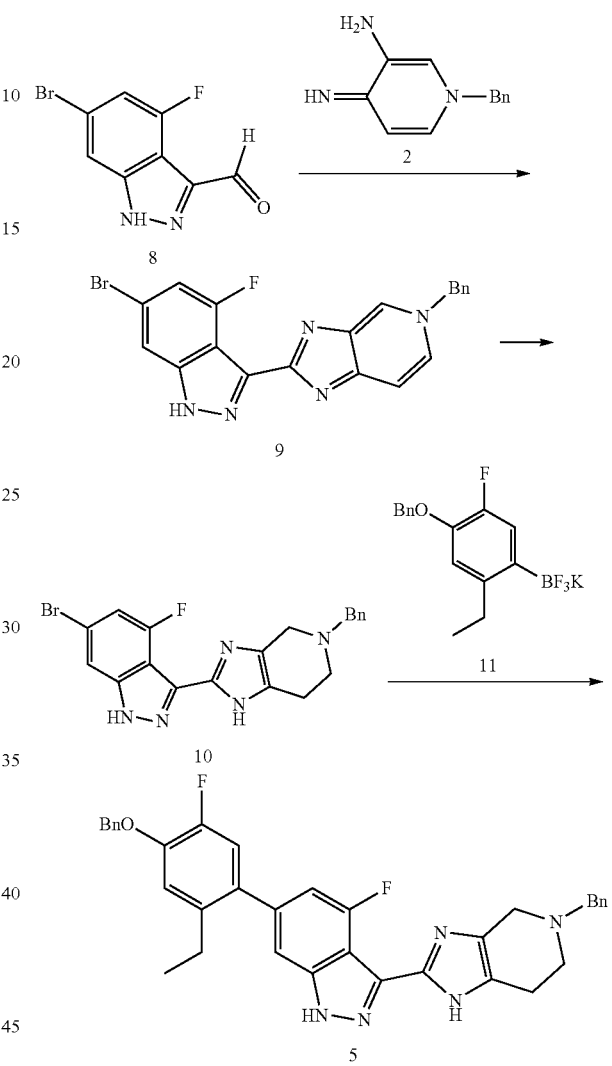

where reagent 7 is 2,5-dioxopyrrolidin-1-yl 2-morpholinoacetate, i.e. the variable $R^A$ represents the activating agent 2,5-dioxopyrrolidinyl, as described in Example 1. Alternatively, morpholin-4-yl acetic acid, i.e. $R^A$ represents hydrogen, is used as reagent 7, under typical amide bond formation conditions, as described in Example 4.

The bromoindazole aldehyde 8 may be reacted with the benzyl protected imine compound 2 to provide intermediate 9. The reaction is typically conducted in the presence of sodium bisulfite, at a temperature of between about 130° C. and about 140° C. for between about 1 and about 6 hours or until the reaction is substantially complete. Compound 9 is reduced using a reducing agent such as sodium borohydride to provide compound 10, which is combined with protected phenyltrifluoroborate 11 under typical Suzuki-Miyaura coupling conditions to provide intermediate 5. The reaction is typically conducted at elevated temperature in the presence of a palladium catalyst. The Suzuki partner 11, shown in Scheme 2 as the trifluoroborate potassium salt can be prepared by reacting the corresponding boronate (Intermediate 1-5 in Preparation 1 below) with potassium hydrogen difluoride to provide intermediate 11. Alternatively, the boronate intermediate can be used in place of the trifluoroborate 11.

Accordingly, in a method aspect, the invention provides a process of preparing a compound of formula 1 or a pharmaceutically acceptable salt thereof, the process comprising reacting a compound of formula 6 with a compound of formula 7, as illustrated in Scheme 1 to provide a compound of formula 1 or a pharmaceutically acceptable salt thereof.

In an additional method aspect, the invention provides a compound of formula 5 and a compound of formula 6, useful in preparing a compound of formula 1.

Crystalline Forms

In another aspect, the invention provides 1-(2-(6-(2-Ethyl-5-fluoro-4-hydroxyphenyl)-4-fluoro-1H-indazol-3-yl)-1,4,6,7-tetrahydro-5H-imidazo[4,5-c]pyridin-5-yl)-2-morpholinoethan-1-one (1) in crystalline form.

Form 1

Crystalline Form 1 of the invention is a crystalline free form of compound 1. In one aspect, Form 1 is characterized by a powder X-ray diffraction (PXRD) pattern having significant diffraction peaks, among other peaks, at 2θ values of 8.16±0.20, 8.97±0.20, 15.29±0.20, 16.70±0.20, 18.00±0.20, and 20.18±0.20. Form 1 may be further characterized by a PXRD pattern having two or more additional diffraction peaks, including three or more and four or more additional diffraction peaks at 2θ values selected from 7.69±0.20, 10.66±0.20, 11.46±0.20, 11.91±0.20, 15.80±0.20, 17.02±0.20, 18.83±0.20, 22.39±0.20, 22.98±0.20, 24.89±0.20, and 26.54±0.20. In another aspect, Form 1 is characterized by a PXRD pattern having three, four, five, or six diffraction peaks at 2θ values selected from 8.16±0.20, 8.97±0.20, 15.29±0.20, 16.70±0.20, 18.00±0.20, and 20.18±0.20.

As is well known in the field of powder X-ray diffraction, peak positions of PXRD pattern are relatively less sensitive to experimental details, such as details of sample preparation and instrument geometry, than are the relative peak heights. Thus, in one aspect, the crystalline Form 1 is characterized by a powder x-ray diffraction pattern in which the peak positions are substantially in accordance with those shown in FIG. 6.

In another aspect, crystalline Form 1 is characterized by its behavior when exposed to high temperature. As demonstrated in FIG. 7, the differential scanning calorimetry (DSC) trace recorded at a heating rate of 10° C. per minute exhibits a peak in endothermic heat flow, identified as a melt transition, in the range of about 210° C. to about 234° C., or in the range of between about 215° C. to about 229° C., or in the range of between about 220° C. to about 224° C. The crystalline Form 1 is characterized by a differential scanning calorimetry trace recorded at a heating rate of 10° C. per minute which shows a maximum in endothermic heat flow with a peak at about 221.7° C. The thermal gravimetric analysis (TGA) trace of FIG. 8 shows no significant weight loss at temperatures below the onset of decomposition at about 293° C.

Figure 9:
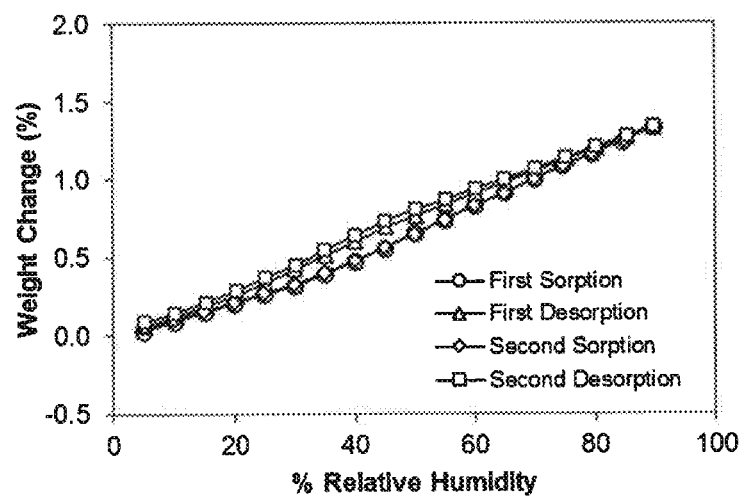
FIG. 9 shows a dynamic moisture sorption (DMS) isotherm of crystalline Form 1 observed at a temperature of about 25° C.
Figure 10:
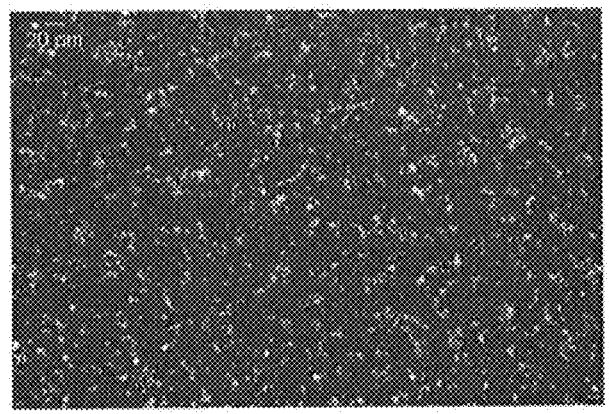
FIG. 10 shows a polarized light microscopy image of Form 1.

A representative dynamic moisture sorption (DMS) trace for the Form 1 crystalline free form of the invention is shown in FIG. 9. Crystalline Form 1 demonstrated a small hysteresis between two cycles of sorption and desorption. Form 1 demonstrated about 0.99% weight gain in the humidity range of 5% to 70% relative humidity and about 1.32% weight gain in the humidity range of 5% to 90% relative humidity at room temperature, as shown in FIG. 9. Form 1 is considered to be slightly-hygroscopic.

Crystalline Form 1 has been shown to be stable upon exposure to elevated temperature and humidity. After 36 weeks at accelerated conditions of 40° C. and 75% relative humidity, no statistically significant changes in chemical purity were observed.

Form 1 may be prepared by dissolving compound 1 in ethanol upon heating, followed by addition of acetronitrile, wherein the ratio of acetonitrile to ethanol is about 1:1, or from about 1:3 to 3:1. The resulting mixture is then warmed, followed by stirring at a temperature of between about 20° C. and about 25° C. for between about 4 hours and about 30 hours, or for about 16 hours. The solid is then filtered and dried to provide Form 1.

Form 1 may also be prepared by mixing compound 1 with ethanol and stirring the mixture at a temperature of between about 50 and about 80° C. for about 2 to 30 minutes, or about 10 minutes, followed by slow addition of acetonitrile at a temperature of between about 50 and about 80° C., wherein the ratio in volume of acetonitrile to ethanol is from about 3:1 to 1:1 or about 1.5:1. Seeds of Form 1 may be added and the reaction mixture stirred at a temperature of between about 20° C. and about 25° C. for between about 4 hours and about 30 hours, or for about 18 hours. The solid is then filtered and dried to provide form 1.

Form 2

Crystalline Form 2 of the invention is a crystalline free form of compound 1. In one aspect, Form 2 is characterized by a powder X-ray diffraction (PXRD) pattern having significant diffraction peaks, among other peaks, at 2θ values of 10.61±0.20, 11.84±0.20, 14.94±0.20, 18.26±0.20, and 19.06±0.20. Form 2 may be further characterized by a PXRD pattern having additional diffraction peaks at 2θ values of 13.32±0.20, 17.69±0.20, and 21.10±0.20. Form 2 may be further characterized by a PXRD pattern having two or more additional diffraction peaks, including three or more and four or more additional diffraction peaks at 2θ values selected from 10.85±0.20, 16.14±0.20, 16.35±0.20, 18.43±0.20, 19.20±0.20, 19.49±0.20, 20.72±0.20, 21.94±0.20, 22.64±0.20, 23.64±0.20, 25.19±0.20, and 28.08±0.20.

In another aspect, Form 2 is characterized by a PXRD pattern having three, four, five, or six diffraction peaks at 2θ values selected from 10.61±0.20, 11.84±0.20, 13.32±0.20, 14.94±0.20, 17.69±0.20, 18.26±0.20, 19.06±0.20 and 21.10±0.20.

As is well known in the field of powder X-ray diffraction, peak positions of PXRD pattern are relatively less sensitive to experimental details, such as details of sample preparation and instrument geometry, than are the relative peak heights. Thus, in one aspect, the crystalline Form 2 is characterized by a powder x-ray diffraction pattern in which the peak positions are substantially in accordance with those shown in FIG. 1.

The structure of crystalline Form 2 has been further characterized by single crystal x-ray diffraction analysis. The crystals belong to an orthorhombic crystal system and Pbca space group. The unit cell dimensions are: a=9.7245(11) Å, b=16.8197(14) Å, c=32.604(4) Å, α=900, β=90°, γ=900, volume=5332.8(10) $Å^3$. The calculated density is 1.302 g/cm$^3$. The crystals contain eight molecules per unit cell. The structure confirms that the crystals do not contain water or other solvent molecules and the molecular structure is consistent with the structure of the compound of Example 1 as depicted herein. Powder X-ray diffraction peaks predicted from the derived atomic positions are in good agreement with observed results.

In another aspect, crystalline Form 2 is characterized by its behavior when exposed to high temperature. As demonstrated in FIG. 2, the differential scanning calorimetry (DSC) trace recorded at a heating rate of 10° C. per minute exhibits a peak in endothermic heat flow, identified as a melt transition, in the range of about 268° C. to about 277° C., or in the range of between about 270° C. to about 275° C., or in the range of between about 271° C. to about 274° C. The crystalline Form 2 is characterized by a differential scanning calorimetry trace recorded at a heating rate of 10° C. per minute which shows a maximum in endothermic heat flow with a peak at about 272.6±2° C.

Figure 3:
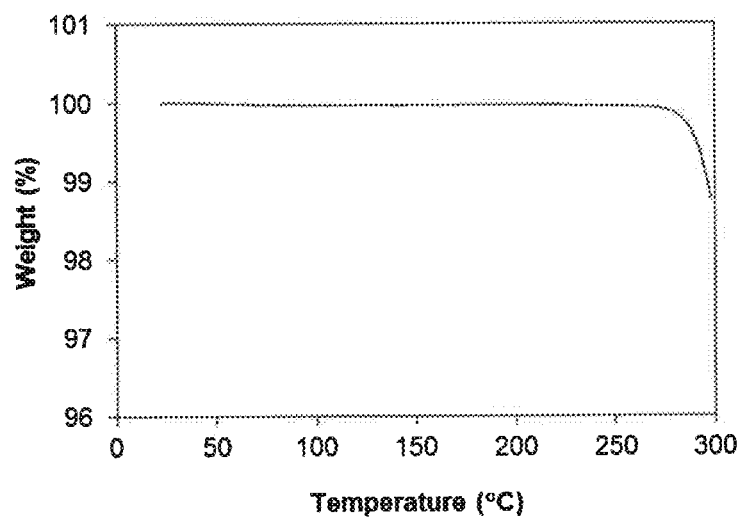
FIG. 3 shows a thermal gravimetric analysis (TGA) plot of crystalline Form 2.

The thermal gravimetric analysis (TGA) trace of FIG. 3 shows no significant weight loss at temperatures below the onset of decomposition at about 269° C.

Figure 4:
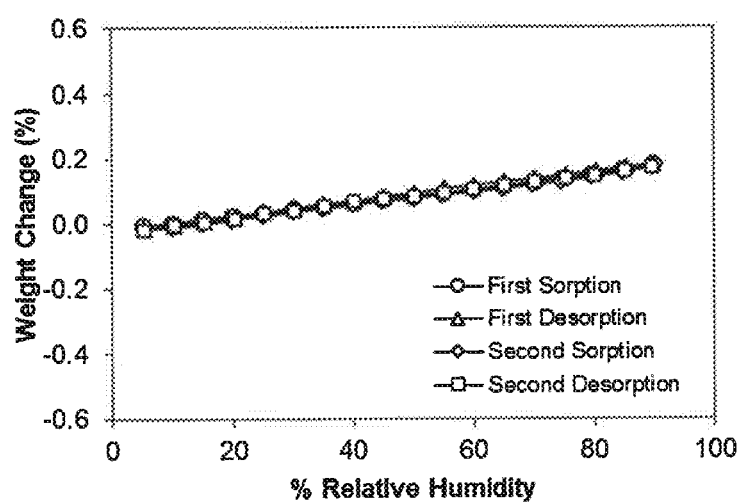
FIG. 4 shows a dynamic moisture sorption (DMS) isotherm of crystalline Form 2 observed at a temperature of about 25° C.
Figure 5:
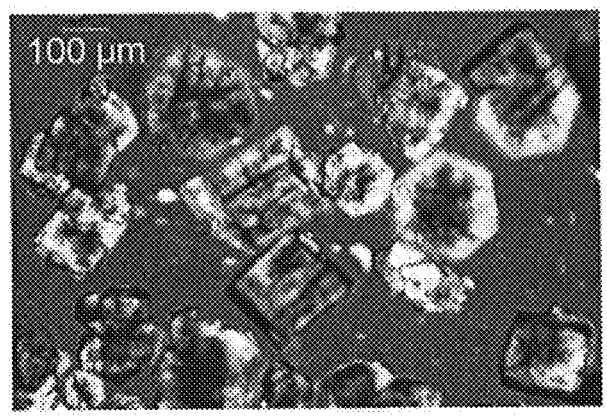
FIG. 5 shows a polarized light microscope image of Form 2.

A representative dynamic moisture sorption (DMS) trace for the Form 2 crystalline free form of the invention is shown in FIG. 4. Crystalline Form 2 showed no hysteresis between two cycles of sorption and desorption and demonstrated an exceptionally small propensity for hygroscopicity. Form 2 demonstrated about 0.18% weight gain in the humidity range of 5% to 90% relative humidity and about 0.12% weight gain in the humidity range of 5% to 70% relative humidity at room temperature, as shown in FIG. 4. Form 2 is considered to be non-hygroscopic.

Form 2 can be prepared by dissolving compound 1 of example 1 in DMSO (for example, at a ratio of 1 g of compound 1 for 1 to 3 mL, or about 2 mL of DMSO) at a temperature between about 45 and 75° C., or at about 60° C., followed by addition of methanol, wherein the ratio in volume of methanol to DMSO is from about 1:4 to about 1:1, or about 1:2. The homogenous mixture is then added dropwise to a premixed solution of methanol and water (wherein the ratio of methanol to DMSO is between 1.5 and 3 to 1), at a temperature between about 60 and about 90° C., or about 75° C., wherein the ratio in volume of the premixed solution of methanol to water is from about 0.5:1 to about 1:2, or about 1:0.9. The mixture is then allowed to stir at a temperature between about 60 and about 90° C., or about 75° C. for about 30 minutes to about 2 hours, or about 1 hour. Water can then be slowly added at a temperature between about 60 and about 90° C., or about 75° C., wherein the ratio in volume of water to methanol is between 2 and 4. The resulting slurry is then slowly cooled down to room temperature (typically, a temperature between about 20 and about 25° C.), typically over about 2 to about 12 hours or about 6 hours. The slurry is then held at room temperature and then filtered and washed with a mixture of water and methanol at about 50 to about 90%, or about 70% water, to provide Form 2.

In one aspect, the invention provides a method of preparing crystalline Form 2 comprising:
(a) forming an homogenous mixture of 1-(2-(6-(2-ethyl-5-fluoro-4-hydroxyphenyl)-4-fluoro-1H-indazol-3-yl)-1,4,6,7-tetrahydro-5H-imidazo[4,5-c]pyridin-5-yl)-2-morpholinoethan-1-one in a polar aprotic solvent, or in a polar water-miscible solvent, or in a mixture of a polar aprotic solvent and a polar water-miscible solvent, at a temperature between 45 and 75° C.;
(b) adding the homogenous mixture to a mixture of a water miscible solvent and water at a temperature between 60 and 90° C. to give a second mixture;
(c) slowly adding water to the second mixture at a temperature between 60 and 90° C. to form a slurry; and
(d) isolating the crystalline form from the slurry.

In some aspects, the polar aprotic solvent of step (a) is selected from the group consisting of DMSO, DMF, NMP, DMAc, and nitromethane, the polar water-miscible solvent of step (a) is selected from the group consisting of acetonitrile, acetone, methanol, ethanol, and THF, and the water miscible solvent of step (b) is selected from the group consisting of acetonitrile, acetone, methanol, ethanol, n-propanol, isopropanol, n-butanol, THF, DMSO, DMF, NMP, DMAc, and nitromethane. In some aspects, the polar aprotic solvent of step (a) is DMSO, the polar water-miscible solvent of step (a) is methanol, and the water miscible solvent of step (b) is methanol.

In some aspects, the slurry obtained in step (c) is cooled down to a temperature between about 20 and 25° C. before step (d).

Alternatively, Form 2 can be formed by stirring the compound 1 obtained in example 1 in a mixture of a polar water miscible solvent and water, at a temperature between 60 and 90° C. In some aspects, the ratio of solvent to water is about 1:1, or from 2:1 to 0.5:1. In some aspects, the polar water miscible solvent is selected from the group consisting of acetonitrile, acetone, methanol, ethanol, n-propanol, isopropanol, n-butanol, THF, DMSO, DMF, NMP, DMAc, and nitromethane.

Pharmaceutical Compositions

Compound 1, and pharmaceutically-acceptable salts thereof are typically used in the form of a pharmaceutical composition or formulation. Such pharmaceutical compositions may advantageously be administered to a patient by any acceptable route of administration including, but not limited to, oral, inhalation, optical injection, topical (including transdermal), rectal, nasal, and parenteral modes of administration.

Accordingly, in one of its compositions aspects, the invention is directed to a pharmaceutical composition comprising a pharmaceutically-acceptable carrier or excipient and compound 1, where, as defined above, "compound 1" means compound 1 or a pharmaceutically-acceptable salt thereof. Optionally, such pharmaceutical compositions may contain other therapeutic and/or formulating agents if desired. When discussing compositions and uses thereof, compound 1 may also be referred to herein as the "active agent".

In some aspects, the disclosure provides a pharmaceutical composition comprising compound 1, or a pharmaceutically acceptable salt thereof, or Form 1 or Form 2 and a pharmaceutically-acceptable carrier. In some aspects, the pharmaceutical composition is suitable for application to the eye. In some aspects, the composition is suitable for injection into the eye. In some aspects, the composition is suitable for intravitreal injection. In some aspects, the composition is a suspension. In some aspects, the composition is a crystalline suspension. In some aspects, the composition is a suspension of Form 1 or Form 2.

The pharmaceutical compositions of the invention typically contain a therapeutically effective amount of compound 1. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.01 to about 95% by weight of the active agent; including, for example, from about 0.05 to about 30% by weight; and from about 0.1% to about 10% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts.

Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for ocular or parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of compound 1 as an active ingredient.

When intended for oral administration in a solid dosage form (i.e., as capsules, tablets, pills and the like), the pharmaceutical compositions of the invention will typically comprise the active agent and one or more pharmaceutically-acceptable carriers. Optionally, such solid dosage forms may comprise: fillers or extenders, such as starches, microcrystalline cellulose, lactose, dicalcium phosphate, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as crosscarmellose sodium, agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, hydroxypropyl methylcellulose, methacrylic acid, methacrylic acid ester copolymers, cellulose acetate trimellitate, carboxymethyl ethyl cellulose, hydroxypropyl methyl cellulose acetate succinate, and the like.

Pharmaceutical compositions of the invention may also be formulated to provide slow or controlled release of the active agent using, by way of example, hydroxypropyl methyl cellulose in varying proportions; or other polymer matrices, liposomes and/or microspheres. In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), oleic acid, glycerol, tetrahydrofuryl alcohol, polyethylene glycols and fatty acid esters of sorbitan, and mixtures thereof. Alternatively, certain liquid formulations can be converted, for example, by spray drying, to a powder, which is used to prepare solid dosage forms by conventional procedures.

Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Compound 1 can also be administered parenterally (e.g. by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Compound 1 may also be formulated as a sterile aqueous suspension or solution for ocular injection. Useful excipients that may be included in such an aqueous formulation include polysorbate 80, cellulose polymers such as carboxymethylcellulose, hydroxypropyl methylcellulose, methylcellulose, potassium chloride, calcium chloride, sodium chloride, magnesium chloride, sodium acetate, sodium citrate, histidine, α-a-trehalose dihydrate, sucrose, polysorbate 20, hydroxypropyl-3-cyclodextrin, benzalkonium chloride, Amberlite IRP-69, polyoxyethylene glycol ethers (lauryl, stearyl and oleyl), ethylenediaminetetra acetic acid sodium salt, sodium taurocholate, saponins and cremophor EL, polycarbophil-cysteine, Xanthan gum, Gellan gum, hyaluronic acid, liposomes, and sodium phosphate. Permeability enhancers, surfactants, bile acids, cyclodextrins such as 2-hydroxypropyl-β-cyclodextrin, and chelating agents may be included in the formulation. Cylindrical oligonucleotides with a hydrophilic outer surface and a lipophilic inner surface that have the ability of forming complexes with an active agent may also be included in the formulation. Benzyl alcohol may serve as a preservative and sodium chloride may be included to adjust tonicity. In addition, hydrochloric acid and/or sodium hydroxide may be added to the solution for pH adjustment. Aqueous formulations for ocular injection may be prepared as preservative-free.

The ocular formulation may allow sustained release of the active ingredient to the eye. The ocular formulation may be formulated as an emulsion (oil in water or water in oil), a suspension, or an ointment. The suspension formulation may contain compound 1, or a pharmaceutically acceptable salt thereof, as a crystalline form, for example Form 1 or Form 2, or in an amorphous state.

Compound 1 may also be formulated to be suitable for eye drop dosing or as an intravitreal implant. The implant may allow delivering constant therapeutic levels of drug. Reservoir implants are typically made with a pelleted drug core surrounded by nonreactive substances such as silicon, ethylene vinyl acetate (EVA), or polyvinyl alcohol (PVA); these implants are nonbiodegradable and can deliver continuous amounts of a drug for months to year. Matrix implants may also be used. They are typically used to deliver a loading dose followed by tapering doses of the drug during a 1-day to 6-month time period. They are most commonly made from the copolymers poly-lactic-acid (PLA) and/or poly-lactic-glycolic acid (PLGA), which degrade to water and carbon dioxide. Iontophoresis may also be used. It is a noninvasive technique in which a small electric current is applied to enhance ionized drug penetration into tissue.

Encapsulated cell technology (ECT), which is a cell-based delivery system may also be used to deliver the therapeutic agent to the eye. Typically, genetically modified cells are packaged in a hollow tube of semipermeable membrane, which prevents immune-cell entry and allows nutrients and therapeutic molecules to diffuse freely across the membrane. Two ends of the polymer section are sealed, and a titanium loop is placed on the anchoring end, which is implanted at the pars plana and anchored to the sclera.

Compound 1 may be formulated into any form allowing delivery to the back of the eye. Examples of modes of delivery are known in the literature (Kuno et al, *Polymers*, 2011, 3, 193-221, del Amo et al, *Drug Discovery Today*, 2008, 13, 135-143, Short, *Toxicologic Pathology*, 2008, 36, 49-62). Such modes of delivery include but are not limited to suprachoroidal delivery which allows delivery to the choroid and retina through the suprachoroidal space, sub-Tenon delivery, periocular delivery, contact lenses, punctal plugs, and scleral plugs. Compound 1 may also be delivered by periocular, suprascleral, retrobulbar, peribulbar, or sub-conjunctival injection.

Compound 1 may be delivered as an emulsion, polymeric micro or nanospheres, liposomes, micro or nanoparticles, microspheres, micelles, or dendrimers. Biodegradable and biocompatible polymers, such as polyactide and PLGA can be used. Compound 1 may be encapsulated.

In addition, compound 1 may be formulated for topical administration to the skin as an ointment or cream. Ointment formulations are semisolid preparations having a base of an oily or greasy material that is typically clear. Suitable oily materials for use in ointment formulations include petrolatum (petroleum jelly), beeswax, cocoa butter, shea butter, and cetyl alcohol. Ointments may optionally additionally include emollients and penetration enhancers, if desired.

Cream formulations may be prepared as emulsions comprising an oil phase and aqueous phase, typically including purified water. Components of cream formulations may include: oil bases, such as petrolatrum, mineral oils, vegetable and animal oils, and triglycerides; cream bases, such as lanolin alcohols, stearic acid, and cetostearyl alcohol; a gel base, such as polyvinyl alcohol; solvents, such as, propylene glycol and polyethylene glycol; emulsifiers, such as polysorbates, stearates, such as glyceryl stearate, octyl-hydroxystearate, polyoxyl stearate, PEG stearyl ethers, isopropyl palmitate, and sorbitan monostearate; stabilizers, such as polysaccharides and sodium sulfite; emollients (i.e. moisturizers), such as medium chain triglycerides, isopropyl myristate, and dimethicone; stiffening agents, such as cetyl alcohol and stearyl alcohol; antimicrobial agents, such as methylparaben, propylparaben, phenoxyethanol, sorbic acid, diazolidinyl urea, and butylated hydroxyanisole; penetration enhancers, such as N-methylpyrrolidone, propylene glycol, polyethylene glycol monolaurate, and the like; and chelating agents, such as edetate disodium.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising compound 1 and a powder suitable for use in a powder inhaler. Suitable powder bases include, by way of example, lactose or starch.

The following non-limiting examples illustrate representative pharmaceutical compositions of the present invention.

Tablet Oral Solid Dosage Form

Compound 1, or a pharmaceutically-acceptable salt thereof is dry blended with microcrystalline cellulose, polyvinyl pyrrolidone, and crosscarmellose sodium in a ratio of 4:5:1:1 and compressed into tablets to provide a unit dosage of, for example, 5 mg, 20 mg or 40 mg active agent per tablet.

Capsule Oral Solid Dosage Form

Compound 1, or a pharmaceutically-acceptable salt thereof is combined with microcrystalline cellulose, polyvinyl pyrrolidone, and crosscarmellose sodium in a ratio of 4:5:1:1 by wet granulation and loaded into gelatin or hydroxypropyl methylcellulose capsules to provide a unit dosage of, for example, 5 mg, 20 mg or 40 mg active agent per capsule.

Liquid Formulation

A liquid formulation comprising compound 1 (0.1%), water (98.9%) and ascorbic acid (1.0%) is formed by adding a compound of the invention to a mixture of water and ascorbic acid.

Enteric Coated Oral Dosage Form

Compound 1 is dissolved in an aqueous solution containing polyvinyl pyrrolidone and spray coated onto microcrystalline cellulose or sugar beads in a ratio of 1:5 w/w active agent:beads and then an approximately 5% weight gain of an enteric coating comprising an acrylic copolymer is applied. The enteric coated beads are loaded into gelatin or hydroxypropyl methylcellulose capsules to provide a unit dosage of, for example, 30 mg active agent per capsule.

Enteric Coated Oral Dosage Form

An enteric coating comprising a combination of Eudragit-L® and Eudragit-S®, or hydroxypropyl methylcellulose acetate succinate is applied to a tablet oral dosage form or a capsule oral dosage form described above.

Aqueous Formulation for Ocular Injection

Each mL of a sterile aqueous suspension includes from 5 mg to 50 mg of compound 1, sodium chloride for tonicity, 0.99% (w/v) benzyl alcohol as a preservative, 0.75% carboxymethylcellulose sodium, and 0.04% polysorbate. Sodium hydroxide or hydrochloric acid may be included to adjust pH to 5 to 7.5.

Aqueous Formulation for Ocular Injection

A sterile preservative-free aqueous suspension includes from 5 mg/mL to 50 mg/mL of compound 1 in 10 mM sodium phosphate, 40 mM sodium chloride, 0.03°% polysorbate 20, and 5% sucrose.

Ointment Formulation for Topical Administration

Compound 1 is combined with petrolatum, $C_8$-$C_{10}$ triglyceride, octylhydroxystearate, and N-methylpyrrolidone in a ratio to provide a composition containing 0.05% to 5% active agent by weight.

Ointment Formulation for Topical Administration

Compound 1 is combined with white petrolatum, propylene glycol, mono- and di-glycerides, paraffin, butylated hydroxytoluene, and edetate calcium disodium in a ratio to provide a composition containing 0.05% to 5% active agent by weight.

Ointment Formulation for Topical Administration

Compound 1 is combined with mineral oil, paraffin, propylene carbonate, white petrolatum and white wax to provide a composition containing 0.05% to 5% active agent by weight.

Cream Formulation for Topical Administration

Mineral oil is combined with compound 1, propylene glycol, isopropyl palmitate, polysorbate 60, cetyl alcohol, sorbitan monostearate, polyoxyl 40 stearate, sorbic acid, methylparaben and propylparaben to form an oil phase, which is combined with purified water by shear blending to provide a composition containing 0.05% to 5% active agent by weight.

Cream Formulation for Topical Administration

A cream formulation comprising compound 1, benzyl alcohol, cetyl alcohol, citric acid anhydrous, mono and di-glycerides, oleyl alcohol, propylene glycol, sodium cetostearyl sulphate, sodium hydroxide, stearyl alcohol, triglycerides, and water contains 0.05% to 5% active agent by weight.

Cream Formulation for Topical Administration

A cream formulation comprising compound 1, cetostearyl alcohol, isopropyl myristate, propylene glycol, cetomacrogol 1000, dimethicone 360, citric acid, sodium citrate, and purified water, with imidurea, methylparaben, and propylparaben, as preservatives, contains 0.05% to 5% active agent by weight.

Dry Powder Composition

Micronized compound 1 (1 g) is blended with milled lactose (25 g). This blended mixture is then loaded into individual blisters of a peelable blister pack in an amount sufficient to provide between about 0.1 mg to about 4 mg of compound 1 per dose. The contents of the blisters are administered using a dry powder inhaler.

Metered-Dose Inhaler Composition

Micronized compound 1 (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μm. The micronized composition is then loaded into metered-dose inhaler cartridges containing pressurized 1,1,1,2-tetrafluoroethane in an amount sufficient to provide about 0.1 mg to about 4 mg of compound 1 per dose when administered by the metered dose inhaler.

Nebulizer Composition

Compound 1 (25 mg) is dissolved in a solution containing 1.5-2.5 equivalents of hydrochloric acid, followed by addition of sodium hydroxide to adjust the pH to 3.5 to 5.5 and 3% by weight of glycerol. The solution is stirred well until all the components are dissolved. The solution is administered using a nebulizer device that provides about 0.1 mg to about 4 mg of compound 1 per dose.

Utility

Compound 1 has been shown to be a potent inhibitor of the JAK family of enzymes: JAK1, JAK2, JAK3, and TYK2.

Ocular Diseases

Many ocular diseases have been shown to be associated with elevations of proinflammatory cytokines that rely on the JAK-STAT pathway. Since compound 1 exhibits potent inhibition at all four JAK enzymes, it is expected to potently inhibit the signaling and pathogenic effects of numerous cytokines (such as IL-6, IL-2 and IFN-γ), that signal through JAK, as well as to prevent the increase in other cytokines (such as MCP-1 and IP-10), whose production is driven by JAK-STAT pathway signaling.

In particular, compound 1 exhibited $pIC_{50}$ values of 6.4 or greater ($IC_{50}$ values of 400 nM or less) for inhibition of IL-6, IL-2, and IFNγ signaling in the cellular assays described in Assays 3 to 6, including assays registering inhibition of the downstream effects of cytokine elevation.

The pharmacokinetic study of Assay 7 demonstrated sustained exposure in rabbit eyes after a single intravitreal injection and a concentration in plasma at least three orders of magnitude lower than that observed in vitreous tissue.

Furthermore, intravitreal dosing of compound 1 has demonstrated significant inhibition of IL-6 induced pSTAT3 in the rat retina/choroid tissue as well as significant and sustained inhibition of IFN-γ induced IP-10 in the rabbit vitreous as well as retina/choroid tissues. Intravitreal dosing of compound 1 has demonstrated significant and sustained inhibition of IFN-γ induced pSTAT1 in the rabbit.

It is expected that sustained ocular JAK inhibition in the absence of significant systemic levels will result in potent, local anti-inflammatory activity in the eye without systemically-driven adverse effects. Compound 1 is thus expected to be beneficial in a number of ocular diseases that include, but are not limited to, uveitis, diabetic retinopathy, diabetic macular edema, dry eye disease, age-related macular degeneration, retinal vein occlusion, and atopic keratoconjunctivitis.

In particular, uveitis (Horai and Caspi, *J Interferon Cytokine Res,* 2011, 31, 733-744), diabetic retinopathy (Abcouwer, *J Clin Cell Immunol,* 2013, Suppl 1, 1-12), diabetic macular edema (Sohn et al., *American Journal of Opthamology,* 2011, 152, 686-694), dry eye disease (Stevenson et al, *Arch Ophthalmol,* 2012, 130, 90-100), retinal vein occlusion (Shchuko et al, *Indian Journal of Ophthalmology,* 2015, 63(12), 905-911) and age-related macular degeneration (Knickelbein et al, *Int Ophthalmol Clin,* 2015, 55(3), 63-78) are characterized by elevation of certain pro-inflammatory cytokines that signal via the JAK-STAT pathway. Accordingly, compound 1 may be able to alleviate the associated ocular inflammation and reverse disease progression or provide symptom relief in these diseases.

In one aspect, therefore, the invention provides a method of treating an ocular disease in a mammal, the method comprising administering a pharmaceutical composition comprising 1-(2-(6-(2-ethyl-5-fluoro-4-hydroxyphenyl)-4-fluoro-1H-indazol-3-yl)-1,4,6,7-tetrahydro-5H-imidazo[4,5-c]pyridin-5-yl)-2-morpholinoethan-1-one or a pharmaceutically-acceptable salt thereof and a pharmaceutical carrier to the eye of the mammal. In one aspect, the ocular disease is uveitis, diabetic retinopathy, diabetic macular edema, dry eye disease, age-related macular degeneration, retinal vein occlusion or atopic keratoconjunctivitis. In one aspect, the method comprises administering compound 1 by intravitreal injection.

Inflammatory Skin Disease

Atopic dermatitis, for example, has been associated with elevation of proinflammatory cytokines that rely on the JAK-STAT pathway, in particular, IL-4, IL-5, IL-10, IL-13, and IFNγ. In addition to the cytokine inhibition in cellular assays cited above, compound 1 exhibited an $IC_{50}$ value of 13 nM for inhibition of IL-13, as described in Assay 2. Furthermore, model cream and ointment formulations of compound 1 have demonstrated sustained dermal levels for at least 2 days in mice and at least 7 days in mini-pig without detectable plasma exposure.

It is expected that sustained dermal levels of compound 1 in the absence of significant systemic levels will result in potent local anti-inflammatory and anti-pruritic activity in the skin without systemically-driven adverse effects. Therefore, compound 1 is expected to be beneficial in a number dermal inflammatory or pruritic conditions that include, but are not limited to alopecia areata, vitiligo, cutaneous T cell lymphoma, prurigo nodularis, lichen planus, primary localized cutaneous amyloidosis, bullous pemphigoid, skin manifestations of graft versus host disease, pemphigoid, discoid lupus, granuloma annulare, lichen simplex chronicus, vulvar/scrotal/perianal pruritus, lichen sclerosus, post herpetic neuralgia itch, lichen planopilaris, and foliculitis decalvans.

In particular, alopecia areata (Xing et al., *Nat Med.* 2014 September; 20(9): 1043-9), vitiligo (Craiglow et al, *JAMA Dermatol.* 2015 October; 151(10): 1110-2), cutaneous T cell lymphoma (Netchiporouk et al., *Cell Cycle.* 2014; 13(21): 3331-5), prurigo nodularis (Sonkoly et al., *J Allergy Clin Immunol.* 2006 February; 117(2):411-7), lichen planus (Welz-Kubiak et al., *J Immunol Res.* 2015; 2015:854747), primary localized cutaneous amyloidosis (Tanaka et al., *Br J Dermatol.* 2009 December; 161(6):1217-24), bullous pemphigoid (Feliciani et al., *Int J Immunopaxthol Pharmacol.* 1999 May-August; 12(2):55-61), and dermal manifestations of graft versus host disease (Okiyama et al., *J Invest Dermatol.* 2014 April; 134(4):992-1000) are characterized by elevation of certain cytokines that signal via JAK activation. Accordingly, compound 1 may be able to alleviate associated dermal inflammation or pruritus driven by these cytokines. In particular, compound 1 is expected to be useful for the treatment of atopic dermatitis and other inflammatory skin diseases.

In one aspect, therefore, the invention provides a method of treating an inflammatory skin disease in a mammal (e.g., a human), the method comprising applying a pharmaceutical composition comprising 1-(2-(6-(2-ethyl-5-fluoro-4-hydroxyphenyl)-4-fluoro-1H-indazol-3-yl)-1,4,6,7-tetrahydro-5H-imidazo[4,5-c]pyridin-5-yl)-2-morpholinoethan-1-one or a pharmaceutically-acceptable salt thereof and a pharmaceutical carrier to the skin of the mammal. In one aspect, the inflammatory skin disease is atopic dermatitis.

Compound 1 may also be used in combination with gram positive antibiotics, such as mupirocin and fusidic acid, to treat inflammatory skin diseases. In one aspect, therefore, the invention provides a method of treating an inflammatory skin disease in a mammal, the method comprising applying compound 1 and a gram positive antibiotic to the skin of the mammal. In another aspect, the invention provides a pharmaceutical composition comprising 1-(2-(6-(2-ethyl-5-fluoro-4-hydroxyphenyl)-4-fluoro-1H-indazol-3-yl)-1,4,6,7-tetrahydro-5H-imidazo[4,5-c]pyridin-5-yl)-2-morpholinoethan-1-one or a pharmaceutically-acceptable salt thereof, a gram positive antibiotic, and a pharmaceutically-acceptable carrier.

Respiratory Diseases

Cytokines which signal through the JAK-STAT pathway, in particular IL-2, IL-3, IL-4, IL-5, IL-6, IL-9, IL-11, IL-13, IL-23, IL-31, IL-27, thymic stromal lymphopoietin (TSLP), interferon-γ (IFNγ) and granulocyte-macrophage colony-stimulating factor (GM-CSF) have also been implicated in asthma inflammation and in other inflammatory respiratory diseases. As described above, compound 1 has been shown to be a potent inhibitor of the JAK1, JAK2, JAK3, and TYK2 enzymes and has also demonstrated potent inhibition of pro-inflammatory cytokines in cellular assays.

The anti-inflammatory activity of JAK inhibitors has been robustly demonstrated in preclinical models of asthma (Malaviya et al., *Int Immunopharmacol,* 2010, 10, 829,-836; Matsunaga et al., *Biochem and Biophys Res Commun,* 2011, 404, 261-267; Kudlacz et al., *Eur J Pharmacol,* 2008, 582, 154-161.) Accordingly, compound 1 is expected to be useful for the treatment of inflammatory respiratory disorders, in particular, asthma. Inflammation and fibrosis of the lung is characteristic of other respiratory diseases in addition to asthma such as chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, and bronchiolitis obliterans. Compound 1, therefore, is also expected to be useful for the treatment of chronic obstructive pulmonary disease, cystic fibrosis, pneumonitis, interstitial lung diseases (including idiopathic pulmonary fibrosis), acute lung injury, acute respiratory distress syndrome, bronchitis, emphysema, bronchiolitis obliterans, and sarcoidosis.

In one aspect, therefore, the invention provides a method of treating a respiratory disease in a mammal (e.g., a human), the method comprising administering to the mammal 1-(2-(6-(2-ethyl-5-fluoro-4-hydroxyphenyl)-4-fluoro-1H-indazol-3-yl)-1,4,6,7-tetrahydro-5H-imidazo[4,5-c]pyridin-5-yl)-2-morpholinoethan-1-one or a pharmaceutically-acceptable salt thereof.

In one aspect, the respiratory disease is asthma, chronic obstructive pulmonary disease, cystic fibrosis, pneumonitis, chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, bronchiolitis obliterans, or sarcoidosis. In another aspect, the respiratory disease is asthma or chronic obstructive pulmonary disease.

In a further aspect, the respiratory disease is a lung infection, a helminthic infection, pulmonary arterial hypertension, sarcoidosis, lymphangioleiomyomatosis, bronchiectasis, or an infiltrative pulmonary disease. In yet another aspect, the respiratory disease is drug-induced pneumonitis, fungal induced pneumonitis, allergic bronchopulmonary aspergillosis, hypersensitivity pneumonitis, eosinophilic granulomatosis with polyangiitis, idiopathic acute eosinophilic pneumonia, idiopathic chronic eosinophilic pneumonia, hypereosinophilic syndrome, Loffler syndrome, bronchiolitis obliterans organizing pneumonia, or immune-checkpoint-inhibitor induced pneumonitis.

The invention further provides a method of treating asthma in a mammal, the method comprising administering to the mammal a pharmaceutical composition comprising 1-(2-(6-(2-ethyl-5-fluoro-4-hydroxyphenyl)-4-fluoro-1H-indazol-3-yl)-1,4,6,7-tetrahydro-5H-imidazo[4,5-c]pyridin-5-yl)-2-morpholinoethan-1-one or a pharmaceutically-acceptable salt thereof and a pharmaceutically-acceptable carrier.

Compound 1, or a pharmaceutically acceptable salt thereof, may also be useful to treat eosinophilic lung diseases. Eosinophilic airway inflammation which is a characteristic feature of diseases collectively termed eosinophilic lung diseases (Cottin et al., *Clin. Chest. Med.*, 2016, 37(3), 535-56). Eosinophilic diseases have been associated with IL-4, IL-13 and IL-5 signaling. Eosinophilic lung diseases include infections (especially helminthic infections), drug-induced pneumonitis (induced for example by therapeutic drugs such as antibiotics, phenytoin, or 1-tryptophan), fungal-induced pneumonitis (e.g. allergic bronchopulmonary aspergillosis), hypersensitivity pneumonitis and eosinophilic granulomatosis with polyangiitis (formerly known as Churg-Strauss syndrome). Eosinophilic lung diseases of unknown etiology include idiopathic acute eosinophilic pneumonia, idiopathic chronic eosinophilic pneumonia, hypereosinophilic syndrome, and Loffler syndrome.

Compound 1, or a pharmaceutically acceptable salt thereof, may also be useful to treat PAH. A polymorphism in the IL-6 gene has been associated with elevated IL-6 levels and an increased risk of developing pulmonary arterial hypertension (PAH) (Fang et al., *J Am Soc Hypertens.*, 2017, 11(3), 171-177). Corroborating the role of IL-6 in PAH, inhibition of the IL-6 receptor chain gp130 ameliorated the disease in a rat model of PAH (Huang et al., *Can J Cardiol.*, 2016, 32(11), 1356.e1-1356.e10).

Compound 1, or a pharmaceutically acceptable salt thereof, may also be useful to treat non-allergic lung diseases such as sarcoidosis, and lymphangioleiomyomatosis. Cytokines such as IFNγ, IL-12 and IL-6 have been implicated in a range of non-allergic lung diseases such as sarcoidosis, and lymphangioleiomyomatosis (El-Hashemite et al., *Am. J. Respir. Cell Mol. Biol.*, 2005, 33, 227-230, and El-Hashemite et al., *Cancer Res.*, 2004, 64, 3436-3443).

Compound 1, or a pharmaceutically acceptable salt thereof, may also be useful to treat bronchiectasis and infiltrative pulmonary diseases which are diseases associated with chronic neutrophilic inflammation. Certain cytokines are associated with neutrophilic inflammation (e.g. IL-6, IFNγ).

Pathological T cell activation is critical in the etiology of multiple respiratory diseases. Autoreactive T cells play a role in bronchiolitis obliterans organizing pneumonia (also termed COS). Similar to COS the etiology of lung transplant rejections is linked to an aberrant T cell activation of the recipients T cells by the transplanted donor lung. Lung transplant rejections may occur early as Primary Graft Dysfunction (PGD), organizing pneumonia (OP), acute rejection (AR) or lymphocytic bronchiolitis (LB) or they may occur years after lung transplantation as Chronic Lung Allograft Dysfunction (CLAD). CLAD was previously known as bronchiolitis obliterans (BO) but now is considered a syndrome that can have different pathological manifestations including BO, restrictive CLAD (rCLAD or RAS) and neutrophilic allograft dysfunction. Chronic lung allograft dysfunction (CLAD) is a major challenge in long-term management of lung transplant recipients as it causes a transplanted lung to progressively lose functionality (Gauthier et al., Curr Transplant Rep., 2016, 3(3), 185-191). CLAD is poorly responsive to treatment and therefore, there remains a need for effective compounds capable of preventing or treating this condition. Several JAK-dependent cytokines such as IFNγ and IL-5 are up-regulated in CLAD and lung transplant rejection (Berastegui et al, *Clin Transplant.* 2017, 31, e12898). Moreover, high lung levels of CXCR3 chemokines such as CXCL9 and CXCL10 which are downstream of JAK-dependent IFN signaling, are linked to worse outcomes in lung transplant patients (Shino et al, *PLOS One*, 2017, 12 (7), e0180281). JAK inhibition has been shown to be effective in kidney transplant rejection (Vicenti et al., *American Journal of Transplantation*, 2012, 12, 2446-56). Therefore, compound 1 may have the potential to be effective in treating or preventing lung transplant rejection and CLAD. Similar T cell activation events as described as the basis for lung transplant rejection also are considered the main driver of lung graft-versus-host disease (GVHD) which can occur post hematopoietic stem cell transplants. Similar to CLAD, lung GVHD is a chronic progressive condition with extremely poor outcomes and no treatments are currently approved. A retrospective, multicenter survey study of 95 patients with steroid-refractory acute or chronic GVHD who received the systemic JAK inhibitor ruxolitinib as salvage therapy demonstrated complete or partial response to ruxolitinib in the majority of patients including those with lung GVHD (Zeiser et al, *Leukemia*, 2015, 29, 10, 2062-68). More recently, immune-checkpoint inhibitor induced pneumonitis, another T cell mediated lung disease emerged with the increased use of immune-checkpoint inhibitors. In cancer patients treated with these T cell stimulating agents, fatal pneumonitis can develop. Compound 1, or a pharmaceutically acceptable salt thereof, has the potential to present a novel treatment for these underserved serious respiratory diseases.

Gastrointestinal Diseases

As a JAK inhibitor, compound 1, or a pharmaceutically acceptable salt thereof, may also be useful for a variety of other diseases. Compound 1, or a pharmaceutically acceptable salt thereof, may be useful for a variety of gastrointestinal inflammatory indications that include, but are not limited to, inflammatory bowel disease, ulcerative colitis (proctosigmoiditis, pancolitis, ulcerative proctitis and left-sided colitis), Crohn's disease, collagenous colitis, lymphocytic colitis, Behcet's disease, celiac disease, immune checkpoint inhibitor induced colitis, ileitis, eosinophilic esophagitis, graft versus host disease-related colitis, and infectious colitis. Ulcerative colitis (Reimund et al., *J Clin Immunology*, 1996, 16, 144-150), Crohn's disease (Woywodt et al., *Eur J Gastroenterology Hepatology*, 1999, 11, 267-276), collagenous colitis (Kumawat et al., Mol Immunology, 2013, 55, 355-364), lymphocytic colitis (Kumawat et al., 2013), eosinophilic esophagitis (Weinbrand-Goichberg et al., *Immunol Res,* 2013, 56, 249-260), graft versus host disease-related colitis (Coghill et al., *Blood,* 2001, 117, 3268-3276), infectious colitis (Stallmach et al., *Int J Colorectal Dis,* 2004, 19, 308-315), Behcet's disease (Zhou et al., *Autoimmun Rev,* 2012, 11, 699-704), celiac disease (de Nitto et al., *World J Gastroenterol,* 2009, 15, 4609-4614), immune checkpoint inhibitor induced colitis (e.g., CTLA-4 inhibitor-induced colitis; (Yano et al., *J Translation Med,* 2014, 12, 191), PD-1- or PD-L1-inhibitor-induced colitis), and ileitis (Yamamoto et al., *Dig Liver Dis,* 2008, 40, 253-259) are characterized by elevation of certain pro-inflammatory cytokine levels. As many pro-inflammatory cytokines signal via JAK activation, compound 1, or a pharmaceutically acceptable salt thereof, may be able to alleviate the inflammation and provide symptom relief. In particular, compound 1, or a pharmaceutically acceptable salt thereof may be useful for the induction and maintenance of remission of ulcerative colitis, and for the treatment of Crohn's disease, immune checkpoint inhibitor induced colitis, and the gastrointestinal adverse effects in graft versus host disease. In one aspect, therefore, the invention provides a method of treating a gastrointestinal inflammatory disease in a mammal (e.g., a human), the method comprising administering to the mammal, compound 1, or a pharmaceutically acceptable salt thereof, or a pharmaceutical composition comprising a pharmaceutically-acceptable carrier and compound 1, or a pharmaceutically acceptable salt thereof.

Other Diseases

Compound 1, or a pharmaceutically acceptable salt thereof, may also be useful to treat other diseases such as other inflammatory diseases, autoimmune diseases or cancers.

Compound 1, or a pharmaceutically acceptable salt thereof, may be useful to treat one or more of arthritis, rheumatoid arthritis, juvenile rheumatoid arthritis, transplant rejection, xerophthalmia, psoriatic arthritis, diabetes, insulin dependent diabetes, motor neurone disease, myelodysplastic syndrome, pain, sarcopenia, cachexia, septic shock, systemic lupus erythematosus, leukemia, chronic lymphocytic leukemia, chronic myelocytic leukemia, acute lymphoblastic leukemia, acute myelogenous leukemia, ankylosing spondylitis, myelofibrosis, B-cell lymphoma, hepatocellular carcinoma, Hodgkins disease, breast cancer, Multiple myeloma, melanoma, non-Hodgkin lymphoma, non-small-cell lung cancer, ovarian clear cell carcinoma, ovary tumor, pancreas tumor, polycythemia vera, Sjoegrens syndrome, soft tissue sarcoma, sarcoma, splenomegaly, T-cell lymphoma, and thalassemia major.

Combination Therapy

Compounds of the disclosure or a pharmaceutically acceptable salt thereof may be used in combination with one or more agents which act by the same mechanism or by different mechanisms to treat a disease. The different agents may be administered sequentially or simultaneously, in separate compositions or in the same composition. Useful classes of agents for combination therapy include, but are not limited to, anti-angiogenic, steroid, anti-inflammatory, plasma kallikrein inhibitor, placenta growth factor ligand inhibitor, VEGF-A ligand inhibitor, angiopoietin ligand-2 inhibitor, protein tyrosine phosphatase beta inhibitor, Tek tyrosine kinase receptor stimulator, calcineurin inhibitor, VEGF ligand inhibitor, mTOR complex 1 inhibitor, mTOR inhibitor, IL-17 antagonist, calmodulin modulator, FGF receptor antagonist, PDGF receptor antagonist, VEGF receptor antagonist, TNF alpha ligand inhibitor, TNF binding agent, proteoglycan 4 stimulator, VEGF-C ligand inhibitor, VEGF-D ligand inhibitor, CD126 antagonist, complement cascade inhibitor, glucocorticoid agonist, complement C5 factor inhibitor, cannabinoid receptor antagonist, sphingosine-1-phosphate receptor-1 modulator, sphingosine-1-phosphate receptor-3 modulator, sphingosine-1-phosphate receptor-4 modulator, sphingosine-1-phosphate receptor-5 modulator, acetaldehyde dehydrogenase inhibitor, Flt3 tyrosine kinase inhibitor, Kit tyrosine kinase inhibitor, Protein kinase C inhibitor, adrenocorticotrophic hormone ligand, stromal cell-derived factor 1 ligand inhibitor, immunoglobulin G1 agonist; Interleukin-1 beta ligand inhibitor, mucin stimulator; Nuclear factor kappa B modulator, cytotoxic T-lymphocyte protein-4 stimulator, T cell surface glycoprotein CD28 inhibitor, lipoprotein lipase stimulator; PPAR alpha agonist, adenosine A3 receptor agonist, angiotensin II receptor antagonist, VEGF receptor antagonist, interferon beta ligand, SMAD-2 modulator; TGF beta 1 ligand inhibitor, somatostatin receptor agonist, IL-2 receptor alpha subunit inhibitor, VEGF-B ligand inhibitor, thymosin beta 4 ligand, angiotensin II AT-1 receptor antagonist, CCR2 chemokine antagonist, membrane copper amine oxidase inhibitor, CD11a antagonist, ICAM-1 inhibitor, insulin-like growth factor 1 antagonist, kallikrein inhibitor, fucosyltransferase 6 stimulator, GDP fucose synthetase modulator, GHR gene inhibitor, IGF1 gene inhibitor, VEGF-1 receptor antagonist, albumin agonist, IL-2 antagonist, CSF-1 antagonist; PDGF receptor antagonist, VEGF-2 receptor antagonist, mTOR inhibitor, PPAR alpha agonist, Rho GTPase inhibitor, Rho associated protein kinase inhibitor, complement C3 inhibitor, EGR-1 transcription factor inhibitor, nuclear erythroid 2-related factor modulator, nuclear factor kappa B inhibitor, integrin alpha-V/beta-3 antagonist, erythropoietin receptor agonist, glucagon-like peptide 1 agonist, TNFRSF1A gene stimulator, angiopoietin ligand-2 inhibitor, alpha-2 antiplasmin inhibitor, collagen antagonist, fibronectin inhibitor, laminin antagonist, plasmin stimulator, nerve growth factor ligand, FGF1 receptor antagonist, FGF3 receptor antagonist, itk tyrosine kinase inhibitor, Lck tyrosine kinase inhibitor, Ltk tyrosine kinase receptor inhibitor, PDGF receptor alpha antagonist, PDGF receptor beta antagonist, protein tyrosine kinase inhibitor, VEGF-3 receptor antagonist, membrane copper amine oxidase inhibitor, somatostatin 2 receptor agonist, somatostatin 4 receptor agonist, somatostatin 5 receptor agonist, protein kinase C alpha inhibitor, protein kinase C beta inhibitor, protein kinase C delta inhibitor protein kinase C epsilon inhibitor protein kinase C eta inhibitor, protein kinase C theta inhibitor, ankyrin modulator, mucin stimulator, P2Y2 purinoceptor agonist, gap junction alpha-1 protein inhibitor, CCR3 chemokine antagonist; eotaxin ligand inhibitor, amiloride sensitive sodium channel inhibitor, PDGF receptor antagonist, protein tyrosine kinase inhibitor, retinal pigment epithelium protein inhibitor, matrix metalloprotease inhibitor, PDGF receptor antagonist, PDGF receptor beta antagonist, PDGF-B ligand inhibitor, growth hormone receptor antagonist, cell adhesion molecule inhibitor, integrin modulator, CXCR4 chemokine antagonist, coiled coil domain containing protein inhibitor, Hsp 90 modulator, Rho associated protein kinase inhibitor, VEGF gene inhibitor, endoglin inhibitor, CCR3 chemokine antagonist, maxi K potassium channel modulator, maxi K potassium channel stimulator, PGF2 alpha agonist, prostanoid receptor agonist, voltage gated chloride channel 2 modulator, complement C5a receptor antagonist, inosine monophosphate dehydrogenase inhibitor, interleukin 18 ligand inhibitor, TRP cation channel M8 stimulator, CNTF receptor agonist, TRPV1 gene inhibitor, deoxyribonuclease I stimulator, IRS1 gene inhibitor, Rho associated protein kinase inhibitor, poly ADP ribose polymerase 1 inhibitor, poly ADP ribose polymerase 2 inhibitor, poly ADP ribose polymerase 3 inhibitor, vanilloid VR1 agonist, NFAT5 gene stimulator, Mucin stimulator, Syk tyrosine kinase inhibitor, alpha 2 adrenoceptor agonist, cyclooxygenase inhibitor, amyloid protein deposition inhibitor, glycogen synthase kinase-3 inhibitor, PARP stimulator, tau deposition inhibitor, DDIT4 gene inhibitor, hemoglobin synthesis modulator, interleukin-1 beta ligand inhibitor, TNF antagonist, KCNQ voltage-gated potassium channel stimulator, NMDA receptor antagonist, cyclooxygenase 1 inhibitor, cyclooxygenase inhibitor, 5-HT 1a receptor agonist, calcium channel inhibitor, FGF-2 ligand modulator, phosphoinositide 3-kinase inhibitor, CD44 antagonist, hyaluronidase modulator, hyaluronic acid agonist, IL-1 antagonist, type I IL-1 receptor antagonist, complement factor P inhibitor, tubulin antagonist, beta amyloid antagonist, IL2 gene stimulator, I-kappa B kinase beta inhibitor, nuclear factor kappa B modulator, plasminogen activator inhibitor 1 inhibitor, FGF-2 ligand, protease modulator, and corticotropin modulator.

Specific agents that may be used in combination with the present JAK inhibitor compound include, but are not limited to lanadelumab, aflibercept, RG-7716, AKB-9778, ciclosporin, bevacizumab, everolimus, secukinumab, fluocinolone acetonide, RP-101, squalamine lactate, recombinant human lubricin, OPT-302, sarilumab, dexamethasone, eculizumab, fingolimod, adalimumab, reproxalap, midostaurin, corticotropin, olaptesed pegol, canakinumab, recoflavone, abatacept, fenofibrate, piclidenoson, OpRegen, candesartan, golimumab, pegaptanib, interferon-beta, disitertide, octreotide acetate, anecortave, basiliximab, suprachoroidal triamcinolone acetonide, RGN-259, difluprednate, HL-036, avacincaptad pegol sodium, irbesartan, propagermanium, triamcinolone acetonide, azithromycin, BI-1467335, lifitegrast, loteprednol etabonate, teprotumumab, KVD-001, TZ-101, atesidorsen, Nov-03, bevacizumab, AVA-101, RU-101, voclosporin, vorolanib, sirolimus, choline fenofibrate, VX-210, APL-2, CPC-551, elamipretide. SF-0166, cibinetide, elamipretide, liraglutide, EYS-606, nesvacumab, aflibercept, ocriplasmin, filgotinib, cenegermin, adipocell, brolucizumab, ranibizumab, aflibercept, padeliporfin photodynamic therapy, pazopanib, ASP-8232, veldoreotide, sotrastaurin, abicipar pegol, diquafosol tetrasodium, HCB-1019, conbercept, bertilimumab, SHP-659, THR-317, ALK-001, PAN-90806, interferon alfa-2b, fluocinolone, sunitinib malate, emixustat, hI-con1, TB-403, minocycline, MA09-hRPE cells, pegpleranib sodium, pegvisomant, luminate, burixafor, H-1129, carotuximab, AXP-1275, ranibizumab, isopropyl unoprostone, tesidolumab, enteric-coated mycophenolate sodium, tadekinig alfa, triamcinolone acetonide, cyclosporine, ST-266, AVX-012, NT-501-ECT, tivanisiran, verteporfin, dornase alfa, aganirsen, ripasudil, rucaparib phosphate, zucapsaicin, tetrathiomolybdate, diclofenac, LHA-510, AGN-195263, tacrolimus, rebamipide, R-348, brimonidine tartrate, vizomitin, T-89, LME-636, BI-1026706, rimexolone, tobramycin, TOP-1630, talaporfin, bromfenac sodium, triamcinolone acetonide, davunetide, loteprednol etabonate, XED-60, EG-Mirotin, APD-209, adenovir, PF-04523655, hydroxycarbamide, navamepent, retinalamin, CNTO-2476, ranibizumab, flupirtine, B27PD, S-646240, GLY-230, hydralazine, nepafenac, DexNP, Trehalose, hyaluronic acid, dexamethasone-Ca sustained-release depot, naluzotan, hyaluronidase, sodium hyaluronate, isunakinra, somatostatin, CLG-561, OC-10X, UCA-002, recombinant human epidermal growth factor, pemirolast, VM-100, MB-11316, monosodium alpha luminol, ranibizumab, IMD-1041, LMG-324, HE-10, cinhyaluronate sodium, BDM-E, mesenchymal precursor cells, disulfiram, CTC-96, PG-101, Beifushu, chymotrypsin.

Also provided, herein, is a pharmaceutical composition comprising compound 1, or a pharmaceutically acceptable salt thereof, and one or more other therapeutic agents. The therapeutic agent may be selected from the class of agents specified above and from the list of specific agent described above. In some embodiments, the pharmaceutical composition is suitable for ocular delivery. In some embodiments, the pharmaceutical composition is a liquid or suspension composition.

Further, in a method aspect, the invention provides a method of treating a disease or disorder in a mammal comprising administering to the mammal compound 1, or a pharmaceutically acceptable salt thereof, and one or more other therapeutic agents.

When used in combination therapy, the agents may be formulated in a single pharmaceutical composition, or the agents may be provided in separate compositions that are administered simultaneously or at separate times, by the same or by different routes of administration. Such compositions can be packaged separately or may be packaged together as a kit. The two or more therapeutic agents in the kit may be administered by the same route of administration or by different routes of administration.

EXAMPLES

The following synthetic and biological examples are offered to illustrate the invention, and are not to be construed in any way as limiting the scope of the invention.

In the examples below, the following abbreviations have the following meanings unless otherwise indicated. Abbreviations not defined below have their generally accepted meanings.

ACN=acetonitrile
DCC=dicyclohexylcarbodiimide
DIPEA=N,N-diisopropylethylamine
DMAc=dimethylacetamide
DMF=N,N-dimethylformamide
DMSO=dimethyl sulfoxide
EtOAc=ethyl acetate
HATU=N,N,N',N'-tetramethyl-O-(7-azabenzotriazol-1-yl)uronium hexafluorophosphate
LDA=lithium diisopropylamide
min=minute(s)
MTBE=methyl tert-butyl ether
NBS=N-bromosuccinimide NMP=N-Methyl-2-pyrrolidone
RT=room temperature
THF=tetrahydrofuran
bis(pinacolato)diboron=4,4,5,5,4',4',5',5'-octamethyl-[2,2']bi[[1,3,2]dioxaborolanyl]
Pd(dppf)Cl$_2$—CH$_2$Cl$_2$=dichloro(1,1'-bis(diphenylphosphino)-ferrocene)-dipalladium(II) complex with dichloromethane Reagents and solvents were purchased from commercial suppliers (Aldrich, Fluka, Sigma, etc.), and used without further purification. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by column chromatography or by preparative HPLC, typically using C18 or BDS column packings and conventional eluents. Typical preparative HPLC conditions are described below.

Characterization of reaction products was routinely carried out by mass and $^1$H-NMR spectrometry. For NMR analysis, samples were dissolved in deuterated solvent (such as CD$_3$OD, CDCl$_3$, or d$_6$-DMSO), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or a Waters (Milford, Mass.) 3100 instrument, coupled to autopurification systems.

Preparative HPLC Conditions
Column: C18, 5 µm. 21.2×150 mm or C18, 5 µm 21×250 or C14, 5 µm 21×150 mm
Column temperature: Room Temperature
Flow rate: 20.0 mL/min
Mobile Phases: A=Water+0.05% TFA
B=ACN+0.05% TFA,
Injection volume: (100-1500 µL)
Detector wavelength: 214 nm Crude compounds were dissolved in 1:1 water:acetic acid at about 50 mg/mL. A 4 minute analytical scale test run was carried out using a 2.1×50 mm C18 column followed by a 15 or 20 minute preparative scale run using 100 µL injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.

Preparation 1: 2-(4-(benzyloxy)-2-ethyl-5-fluorophenyl)-4,4,5,5-tetramethyl-1,3,2-dioxaborolane (1-5)

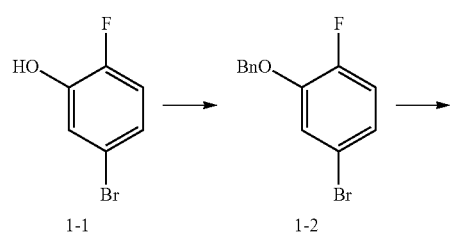

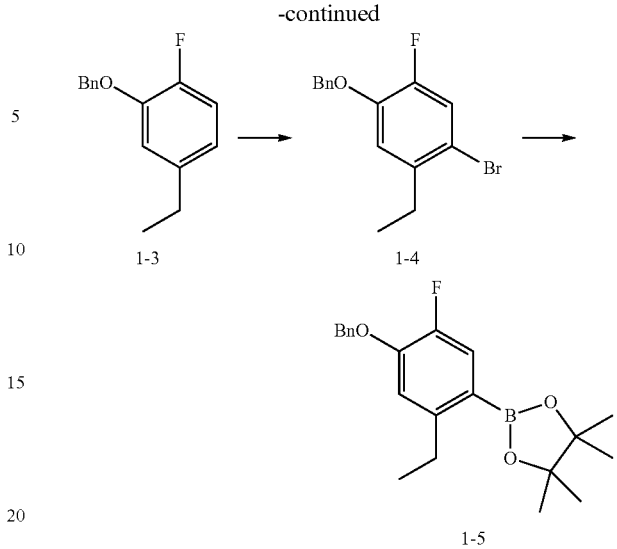

(a) 2-(Benzyloxy)-4-bromo-1-fluorobenzene (1-2)

Two reactions were carried out in parallel and combined for work-up. A mixture of 5-bromo-2-fluorophenol (1-1) (850 g, 4.5 mol), benzyl bromide (837 g, 4.9 mol) and potassium carbonate (923 g, 6.7 mol) in ACN (5 L) was stirred at 20° C. for 12 h. The reactions were combined and concentrated, diluted with water (8 L), and extracted with EtOAc (3×3 L). The organic layer was separated, washed with brine (3 L), dried over sodium sulfate and concentrated. The crude product was purified through a silica gel pad (eluted with 3:1 petroleum ether:EtOAc) to give the title intermediate (1.83 kg, 73% yield) as a white solid. $^1$H NMR (400 MHz, CDCl$_3$) δ 7.38-7.46 (m, 5H), 7.15 (dd, J=7.6, 2.0 Hz, 1H), 6.98-7.15 (m, 1H), 5.12 (s, 2H).

(b) 2-(Benzyloxy)-4-ethyl-1-fluorobenzene (1-3)

Six reactions were carried out in parallel and combined for work-up. To a solution of the product of the previous step (200 g, 711 mmol) in THF (100 mL) was added potassium carbonate (197 g, 1.4 mol). The reaction mixture was purged with nitrogen 3 times, followed by addition of Pd(dppf)Cl$_2$—CH$_2$Cl$_2$ (11.6 g, 14.2 mmol). The reaction mixture was cooled to 0° C., diethylzinc (1 M, 1.07 L) was added drop-wise, and the reaction mixture was stirred at 70° C. for 1 h. The reactions were combined, cooled to 20° C. and poured into water (7 L) slowly. To the mixture was added aq. 4 M HCl to pH 6. The organic layer was separated, and the aqueous phase was extracted with EtOAc (3×2 L). The combined organic layer was washed with brine (5 L), dried over sodium sulfate, concentrated, and purified through a silica gel pad (eluted with 50:1 petroleum ether:EtOAc)) to give the title intermediate (900 g, 92% yield) as a light yellow oil. $^1$H NMR (400 MHz, CDCl$_3$) δ 7.29-7.43 (m, 5H), 6.94-6.97 (m, 1H), 6.82 (d, J=8.0 Hz, 1H), 6.70 (m, 1H), 5.09 (s, 2H), 2.52-2.58 (m, 2H), 1.17 (t, J=7.6 Hz, 3H).

(c) 1-(Benzyloxy)-4-bromo-5-ethyl-2-fluorobenzene (1-4)

Four reactions were carried out in parallel and combined. To a solution of 2-(benzyloxy)-4-ethyl-1-fluorobenzene (1-3) (293 g, 1.3 mol) in ACN (1 L) was added NBS (249 g, 1.4 mol) in portions at 20° C. The reaction mixture was stirred at 20° C. for 2 h. The reaction mixtures were combined and concentrated. The residue was diluted with water (5 L) and extracted with EtOAc (2×5 L). The organic phase was washed with brine (4 L), dried over anhydrous sodium sulfate, filtered and concentrated in vacuo. The crude product was purified by silica gel chromatography (eluted with petroleum ether:EtOAc 100:1-10:1) to give the title intermediate (1.4 kg, 89% yield) as light yellow oil. $^1$H NMR (400 MHz, CDCl$_3$) δ 7.29-7.38 (m, 5H), 7.2 (d, J=10.4 Hz, 1H), 6.8 (d, J=8.8 Hz, 1H), 5.06 (s, 2H), 2.6 (q, J=7.6 Hz, 2H), 1.1 (t, J=7.6 Hz, 3H).

(d) 2-(4-(benzyloxy)-2-ethyl-5-fluorophenyl)-4,4,5,5-tetramethyl-1,3,2-dioxaborolane (1-5)

Seven reactions were carried out in parallel and combined for work-up. To a solution of the product of the previous step (200 g, 647 mmol) in dioxane (2 L) was added potassium acetate (190 g, 1.9 mol), bis(pinacolato)diboron (181 g, 712 mmol), and Pd(dppf)Cl$_2$—CH$_2$Cl$_2$ (10.6 g, 12.9 mmol) under nitrogen at 20° C. The mixture was stirred at 120° C. for 2 h. The reaction mixtures were combined, concentrated, diluted with water (5 L), and extracted with EtOAc (3×4 L). The combined organic phase was dried with anhydrous sodium sulfate, filtered and concentrated in vacuo. The crude product was purified by silica gel chromatography (eluted with petroleum ether:EtOAc 1:0-5:1) to give the title compound (1.35 kg, 84% yield) as a white solid. $^1$H NMR (400 MHz, CDCl$_3$) δ 7.33-7.51 (m, 6H), 6.82 (d, J=7.6 Hz, 1H), 5.17 (s, 2H), 2.85 (q, 0.1=7.6 Hz, 2H), 1.33 (s, 12H), 1.15 (t, J=7.6 Hz, 3H).

Preparation 2: 1-Benzyl-4-imino-1,4-dihydropyridin-3-amine (2)

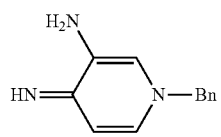

2

To a solution of pyridine-3,4-diamine (400 g, 3.67 mol) in ACN (3 L) was added benzyl bromide (596 g, 3.49 mol) in portions at 0° C. and the reaction mixture was stirred for 30 min and then at 20° C. for 12 h, and filtered. The filter cake was washed with ACN (500 mL) and dried to give the HBr salt of the title compound (600 g, 2.14 mol, 58% yield) as a white powder. $^1$H NMR (400 MHz, MeOD) δ 7.83 (d, J=5.6 Hz, 1H), 7.64 (s, 1H), 7.32-7.40 (m, 5H), 6.76 (d, J=6.8 Hz, 1H), 5.28 (s, 2H).

Preparation 3: 6-(4-(Benzyloxy)-2-ethyl-5-fluorophenyl)-4-fluoro-1H-indazole-3-carbaldehyde (3)

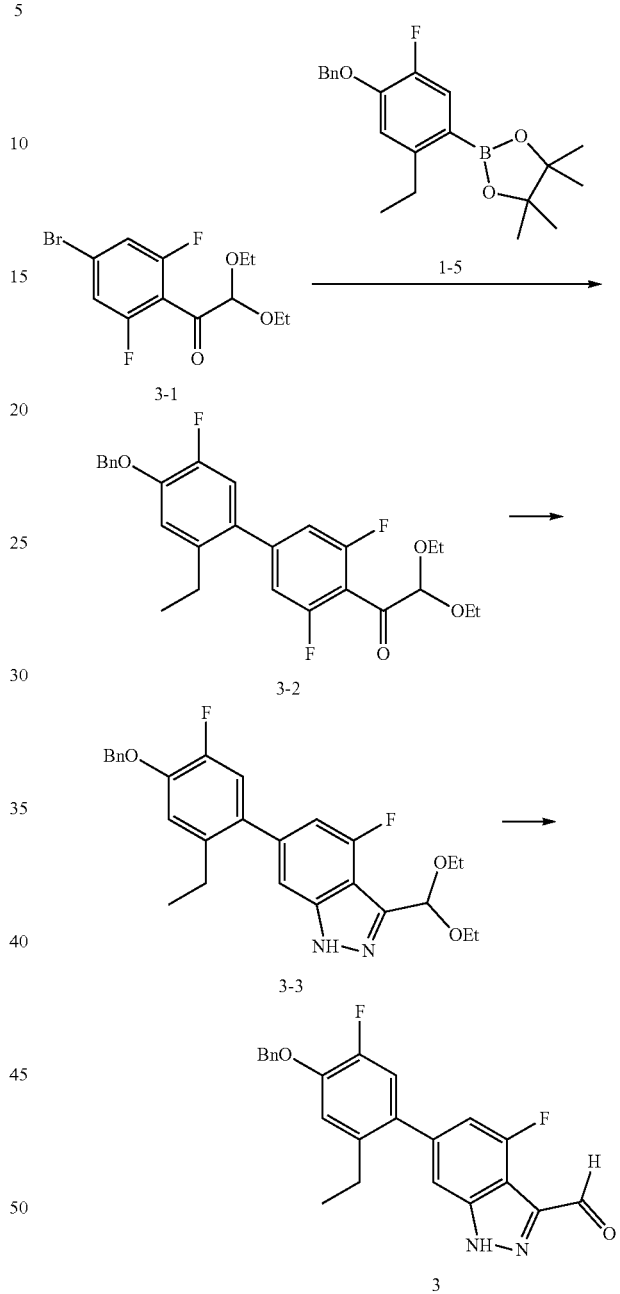

(a) 1-(4-Bromo-2,6-difluorophenyl)-2,2-diethoxyethan-1-one (3-1)

Nine reactions were carried out in parallel and combined for work-up. A solution of 1-bromo-3,5-difluorobenzene (100 g, 518 mmol) in THF (700 mL) was degassed and purged with nitrogen three times. Then 2 M LDA (311 mL) was added at −70° C. and the reaction mixture was stirred at −70° C. for 0.5 h under nitrogen. A solution of ethyl 2,2-diethoxyacetate (96 g, 544 mmol) in THF (200 mL) was added drop-wise at −70° C. under nitrogen and the reaction mixture was stirred for 1 h. The reactions were combined and poured into ice saturated ammonium chloride (10 L) in portions and extracted with EtOAc (3×3 L). The organic layer was separated, washed with brine (5 L), dried over sodium sulfate, concentrated, and purified by silica gel chromatography (eluted with petroleum ether EtOAc 1:0-100:1) to give the title compound (1.26 kg, 84% yield) as a yellow oil. $^1$H NMR (400 MHz, CDCl$_3$) δ 7.12 (d, J=7.2 Hz, 2H), 5.15 (s, 1H), 3.61-3.7 (m, 4H), 1.2 (t, J=7.2 Hz, 6H).

(b) 1-(4'-(benzyloxy)-2'-ethyl-3,5,5'-trifluoro-[1,1'-biphenyl]-4-yl)-2,2-diethoxyethan-1-one (3-2)

Five reactions were carried out in parallel and combined for work-up. To a mixture of 1-(4-bromo-2,6-difluorophenyl)-2,2-diethoxyethan-1-one (3-1) (189 g, 586 mmol) in ethanol (150 mL) and toluene (1.5 L) was added water (150 mL), sodium carbonate (84.8 g, 800 mmol), and 2-(4-(benzyloxy)-2-ethyl-5-fluorophenyl)-4,4,5,5-tetramethyl-1,3,2-dioxaborolane (1-5) (190 g, 533 mmol) at 20° C. The suspension was degassed under vacuum and purged with nitrogen several times. Pd(dppf)Cl$_2$—CH$_2$Cl$_2$ (13 g, 16 mmol) was added and the reaction mixture was purged with nitrogen several times and stirred at 120° C. for 2 h. The reactions were combined, cooled to 20° C., poured into water (5 L) and extracted with EtOAc (3×4 L). The combined organic layers were washed with brine (5 L), dried over sodium sulfate, filtered, concentrated, and purified by silica gel chromatography (eluted with petroleum ether: EtOAc 100:1-5:1) to give the title intermediate (880 g, 70% yield) as a yellow oil. $^1$H NMR (400 MHz, CDCl$_3$) δ 7.36-7.48 (m, 5H), 6.94-6.96 (m, 2H), 6.86-6.92 (m, 2H), 5.29 (s, 1H), 5.19 (s, 2H), 3.67-3.77 (m, 4H), 2.52 (q, J=7.6 Hz, 2H), 1.25 (t, J=6.8 Hz, 6H), 1.07 (t, J=7.2 Hz, 3H).

(c) 6-(4-(benzyloxy)-2-ethyl-5-fluorophenyl)-3-(diethoxymethyl)-4-fluoro-1H-indazole (3-3)

Four reactions were carried out in parallel and combined for work-up. To a solution of the product of the previous step (220 g, 466 mmol) in THF (2 L) was added hydrazine monohydrate (47.6 g, 931 mmol) at 20° C. The reaction mixture was stirred at 100° C. for 12 h. Four reactions were combined and cooled to 20° C. and concentrated. The residue was dissolved in EtOAc (5 L) and washed with 0.1 M HCl (2×1.5 L). The combined organic layers were washed with brine (1.5 L), dried over sodium sulfate, filtered and concentrated to give the title intermediate (900 g, crude) as yellow gum, which was used directly in the next step. $^1$H NMR (400 MHz, CDCl$_3$) δ 7.36-7.48 (m, 5H), 6.94-6.96 (m, 2H), 6.86-6.92 (m, 2H), 5.29 (s, 1H), 5.19 (s, 2H), 3.67-3.77 (m, 4H), 2.52 (q, J=7.6 Hz, 2H), 1.25 (t, J=6.8 Hz, 6H), 1.07 (t, J=7.2 Hz, 3H).

(d) 6-(4-(Benzyloxy)-2-ethyl-5-fluorophenyl)-4-fluoro-1H-indazole-3-carbaldehyde (3)

Three reactions were carried out in parallel and combined for work-up. To a solution of the product of the previous step (300 g, 643 mmol) in acetone (1.5 L) was added 4 M HCl (16 mL) drop-wise at 20° C. and the reaction mixture was stirred at 20° C. for 0.17 h. The reactions were combined, concentrated, diluted with MTBE (1 L), and filtered. The filter cake was washed with MTBE (2×300 mL) and dried under reduced pressure to give the title intermediate (705 g, crude) as a yellow solid, which was used directly in the next step. (m/z): [M+H]$^+$ calcd for C$_{23}$H$_{18}$F$_2$N$_2$O$_2$ 393.13 found 393.1. $^1$H NMR (400 MHz, DMSO-d$_6$) δ 14.51 (s, 1H), 10.17 (d, J=3.6 Hz, 1H), 7.50 (d, J=7.2 Hz, 2H), 7.40-7.42 (m, 4H), 7.24 (d, J=8.4 Hz, 1H), 7.15 (d, J=12.4 Hz, 1H), 7.06 (d, J=8.4 Hz, 1H), 5.25 (s, 2H), 2.52-2.53 (m, 2H), 1.03 (t, J=7.6 Hz, 3H).

Preparation 4: 5-Benzyl-2-(6-(4-(benzyloxy)-2-ethyl-5-fluorophenyl)-4-fluoro-1H-indazol-3-yl)-5H-imidazo[4,5-c]pyridine (4)

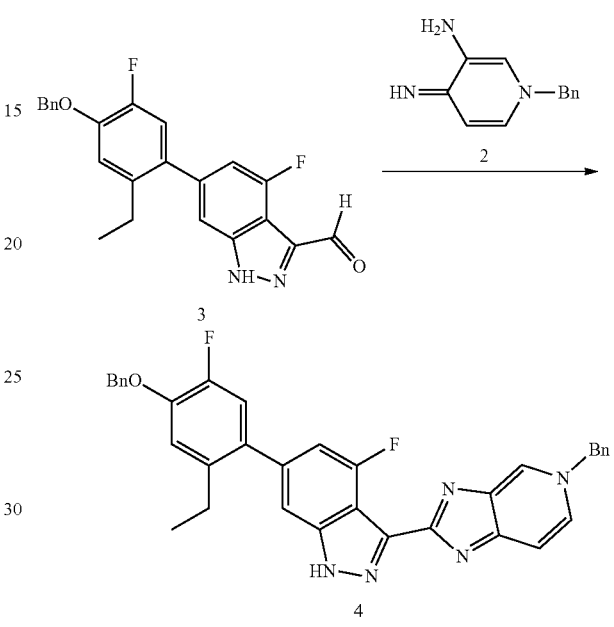

Four reactions were carried out in parallel and combined for work-up. To a solution of 6-(4-(benzyloxy)-2-ethyl-5-fluorophenyl)-4-fluoro-1H-indazole-3-carbaldehyde (3), the product of Preparation 3 (172 g, 440 mmol) in DMF (1.1 L) was added sodium bisulfite (68.6 g, 659 mmol) and 1-benzyl-4-imino-1,4-dihydropyridin-3-amine (2) (136 g, 484 mmol) at 20° C. and the reaction mixture was stirred at 150° C. for 2 h. Four reactions were combined and the reaction mixture was concentrated under reduced pressure. The residue was poured into water (10 L) and filtered. The filter cake was dried under reduced pressure to give the title intermediate (990 g, crude) as a yellow solid, which was used directly without purification. (m z): [M+H]$^+$ calcd for C$_{35}$H$_{27}$F$_2$N$_5$O 572.2 found 572.3.

Preparation 5: 5-Benzyl-2-(6-(4-(benzyloxy)-2-ethyl-5-fluorophenyl)-4-fluoro-1H-indazol-3-yl)-4,5,6,7-tetrahydro-1H-imidazo[4,5-c]pyridine (5)

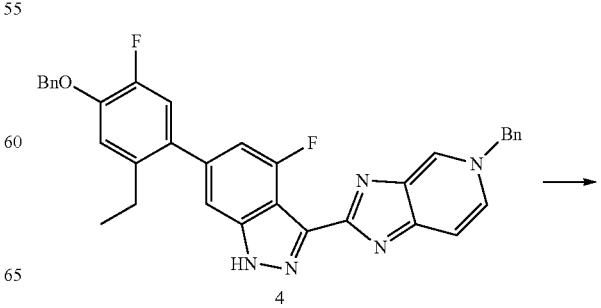

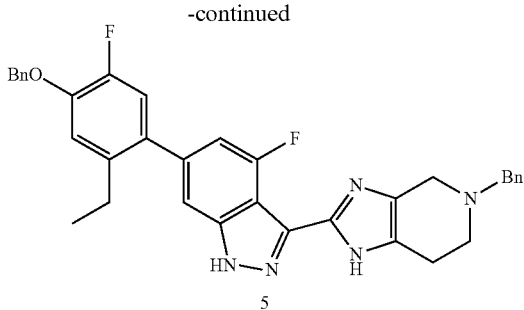

Three reactions were carried out in parallel and combined for work-up. To a mixture of 5-benzyl-2-(6-(4-(benzyloxy)-2-ethyl-5-fluorophenyl)-4-fluoro-1H-indazol-3-yl)-5H-imidazo[4,5-c]pyridine (4), the product of Preparation 4 (330 g, 577 mmol) in methanol (1.5 L) and THF (1 L) was added sodium borohydride (267 g, 6.9 mol) in portions at 20° C. and the reaction mixture was stirred at 20° C. for 24 h. Three reactions were combined and the reaction mixture was added to water (10 L), stirred for 10 min, and filtered. The filtrate was extracted with EtOAc (2×5 L) and the combined organic phase was dried with anhydrous sodium sulfate, filtered and concentrated under vacuum. The crude product was diluted with EtOAc (2 L), stirred for 30 min, and filtered. The filter cake was washed with MTBE (3×200 mL) to give the title intermediate (275 g, 28% yield) as a light yellow solid. (m/z): [M+H]$^+$ calcd for $C_{35}H_{31}F_2N_5O$ 576.25 found 576.3. $^1$H NMR (400 MHz, DMSO-$d_6$) δ 7.50-7.52 (m, 2H), 7.35-7.43 (m, 7H), 7.23-7.25 (m, 3H), 7.15 (d, J=12.0 Hz, 1H), 6.81 (d, J=12.0 Hz, 1H), 5.25 (s, 2H), 3.72 (s, 2H), 3.43 (br. s, 2H), 2.78 (br. s, 2H), 2.66 (br. s, 2H), 2.55 (q, 2H), 1.04 (t, J=7.6 Hz, 3H).

Preparation 6: 5-Ethyl-2-fluoro-4-(4-fluoro-3-(4,5,6,7-tetrahydro-1H-imidazo[4,5-c]pyridin-2-yl)-1H-indazol-6-yl)phenol (6)

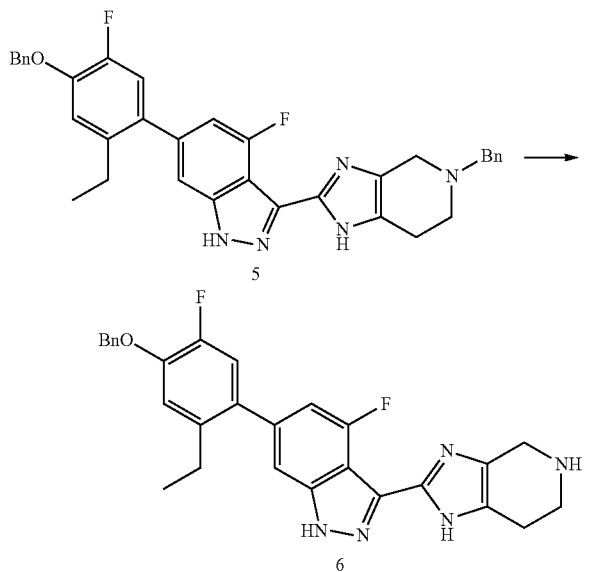

Five reactions were carried out in parallel and combined for work-up. To a mixture of 5-benzyl-2-(6-(4-(benzyloxy)-2-ethyl-5-fluorophenyl)-4-fluoro-1H-indazol-3-yl)-4,5,6,7-tetrahydro-1H-imidazo[4,5-c]pyridine (5), the product of Preparation 5 (55 g, 95.5 mmol) in THF (500 mL) and methanol (500 mL) was added palladium on carbon (15 g, 9.6 mmol) and aq. 12 M HCl (10 mL). The suspension was degassed under vacuum, purged with hydrogen several times and stirred under hydrogen (50 psi) at 50° C. for 12 h. The reactions were combined and the reaction mixture was filtered. The filtrate was concentrated under vacuum to provide the HCl salt of the title intermediate (150 g crude) as an off-white solid. (m/z): [M+H]$^+$ calcd for $C_{21}H_{19}F_2N_5O$ 396.16 found 396.2. $^1$H NMR (400 MHz, MeOD) δ 7.43 (s, 1H), 7.07 (d, J=11.6 Hz, 1H), 6.97 (d, J=11.6 Hz, 1H), 6.91 (d, J=8.8 Hz, 1H), 4.57 (s, 2H), 3.74 (s, 2H), 3.24 (s, 2H), 2.55 (q, J=7.6 Hz, 2H), 1.08 (t, J=7.6 Hz, 3H).

Preparation 7: 2,5-dioxopyrrolidin-1-yl 2-morpholinoacetate (7')

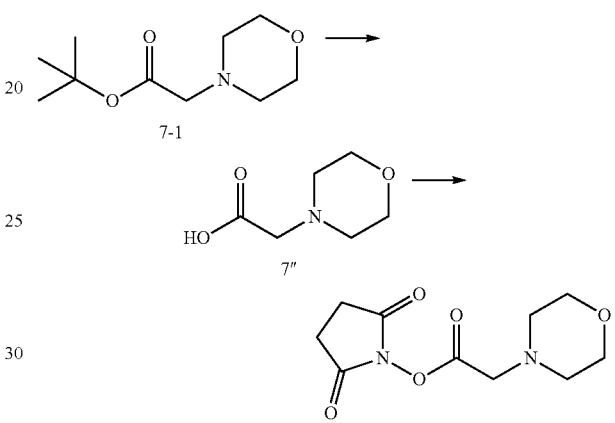

(a) tert-Butyl 2-morpholinoacetate (7-1)

To a mixture of morpholine (160 g, 1.84 mol) and potassium carbonate (381 g, 2.76 mol) in THF (3 L) was added tert-butyl 2-bromoacetate (341 g, 1.75 mol) slowly at 0° C. The reaction mixture was stirred for 30 min and then at 20° C. for 12 h, and concentrated. Water (1.5 L) was added and the reaction mixture was extracted with EtOAc (3×1 L). The organic layer was separated, washed with brine (500 mL), dried over sodium sulfate and concentrated to give the title intermediate (300 g, 81% yield) as a yellow oil. $^1$H NMR (400 MHz, CDCl$_3$) δ 3.74 (t, J=4.8 Hz, 4H), 3.10 (s, 2H), 2.57 (t, J=4.8 Hz, 4H), 1.46 (s, 9H).

(b) 2-Morpholinoacetic acid (7″)

A mixture of the product of the previous step (7-1) (300 g, 1.49 mol) in 3 M HCl in dioxane (2.0 L) was stirred at 20° C. for 12 h and concentrated to give the HCl salt of the title compound (270 g, 99% yield) as a pale solid, which was used directly in the next step $^1$H NMR (400 MHz, MeOD) δ 4.13 (s, 2H), 3.93 (br. s, 4H), 3.64 (br. s, 4H).

(c) 2,5-dioxopyrrolidin-1-yl 2-morpholinoacetate (7')

A mixture of the product of the previous step (150 g, 826 mmol), 1-hydroxypyrrolidine-2,5-dione (95 g, 826 mmol), DCC (256 g, 1.24 mol) and DIPEA (160 g, 1.24 mol) in DCM (2 L) was stirred at 15° C. for 12 h and filtered. The filtrate was concentrated and washed with EtOAc (800 mL). The solid was collected by filtration and concentrated to give the title compound (150 g, 75% yield) as a white solid. $^1$H NMR (400 MHz, DMSO-$d_6$) δ 3.68 (s, 2H), 3.58 (t, J=4.8 Hz, 4H), 2.82 (s, 4H), 2.57 (t, J=5.2 Hz, 4H).

Example 1: 1-(2-(6-(2-Ethyl-5-fluoro-4-hydroxyphenyl)-4-fluoro-1H-indazol-3-yl)-1,4,6,7-tetrahydro-5H-imidazo[4,5-c]pyridin-5-yl)-2-morpholinoethan-1-one (1)

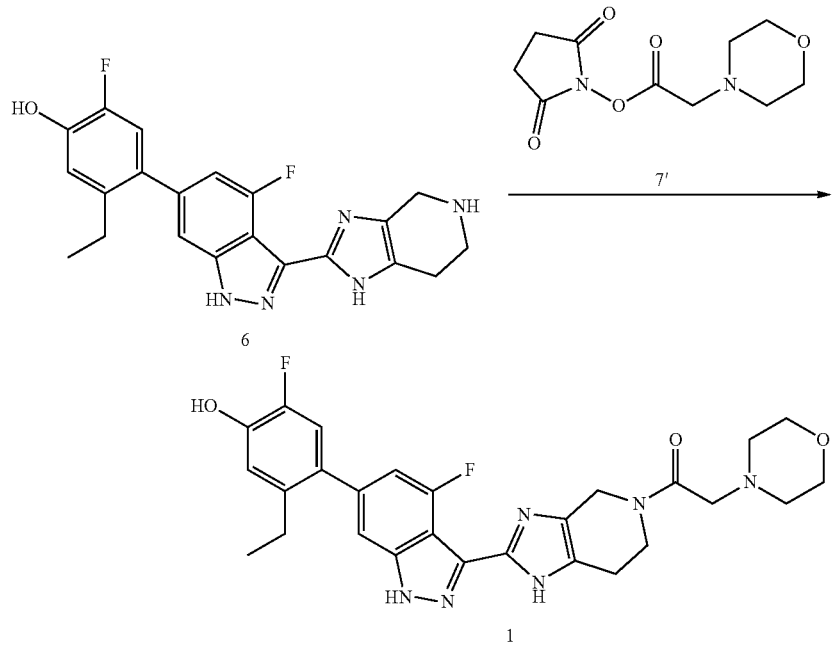

A mixture of 5-ethyl-2-fluoro-4-(4-fluoro-3-(4,5,6,7-tetrahydro-1H-imidazo[4,5-c]pyridin-2-yl)-1H-indazol-6-yl)phenol (6) 2 HCl (100 g, 214 mmol), 2,5-dioxopyrrolidin-1-yl 2-morpholinoacetate (7') (67.2 g, 278 mmol), and DIPEA (69 g, 534 mmol) in DMF (600 mL) was stirred at 15° C. for 12 h and filtered. The solution was purified by reverse-phase chromatography (Agela FLEXATM FS-1L instrument; 2 kg Agela C18 DAC column; 200 g sample dissolved in DMF (900 mL); flow rate 300 mL/min; solvent A water, solvent B ACN; gradient (% B, time (min): 0/15, 0-40/45, 40/50) to afford the title compound (50.0 g, 44.8% yield) as a light yellow solid. (m/z): [M+H]$^+$ calcd for $C_{27}H_{28}F_2N_6O_3$ 523.22 found 523.0. $^1$H NMR (400 MHz, MeOD) δ 7.22 (s, 1H), 6.80-6.96 (m, 3H), 4.68-4.78 (m, 2H), 3.96 (s, 2H), 3.65-3.95 (m, 4H), 3.35-3.38 (m, 2H), 2.77-2.92 (m, 2H), 2.52-2.56 (m, 6H), 1.06 (t, J=7.6 Hz, 3H).

Example 2: Crystalline 1-(2-(6-(2-Ethyl-5-fluoro-4-hydroxyphenyl)-4-fluoro-1H-indazol-3-yl)-1,4,6,7-tetrahydro-5H-imidazo[4,5-c]pyridin-5-yl)-2-morpholinoethan-1-one (1) Form 1

To a 250 mL flask was added 1-(2-(6-(2-ethyl-5-fluoro-4-hydroxyphenyl)-4-fluoro-1H-indazol-3-yl)-1,4,6,7-tetrahydro-5H-imidazo[4,5-c]pyridin-5-yl)-2-morpholinoethan-1-one (1), the product of Example 1 (5 g) and ethanol (50 mL) and the reaction mixture was stirred at 50-80° C. for 10 min and then ACN (75 mL) was added slowly at 50-80° C. followed by seeds from Example 3. The reaction mixture was stirred at 20-25° C. for 18 h. The resulting solid was collected by filtration and dried at 50° C. under vacuum for 18 h to provide the title compound Form 1 (3.6 g, 72% yield)

Example 3: Crystalline 1-(2-(6-(2-Ethyl-5-fluoro-4-hydroxyphenyl)-4-fluoro-1H-indazol-3-yl)-1,4,6,7-tetrahydro-5H-imidazo[4,5-c]pyridin-5-yl)-2-morpholinoethan-1-one (1) Form 1

Compound 1, the product of Example 1, (1 g) was added to ethanol (10 mL) and heated to dissolution. Acetonitrile (10 mL) was added and the reaction mixture was stirred and warmed and then stirred at RT for 16 h, filtered, and dried at 50° C. under vacuum for 18 h to provide the title compound Form 1 (0.23 g).

Example 4: 1-(2-(6-(2-Ethyl-5-fluoro-4-hydroxyphenyl)-4-fluoro-1H-indazol-3-yl)-1,4,6,7-tetrahydro-5H-imidazo[4,5-c]pyridin-5-yl)-2-morpholinoethan-1-one (1)

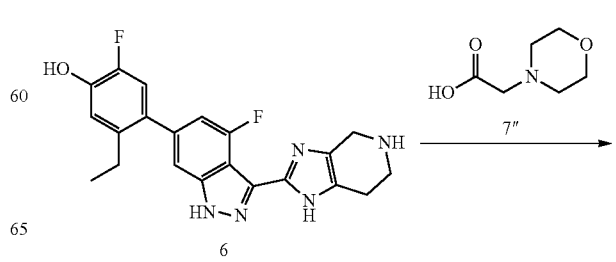

-continued

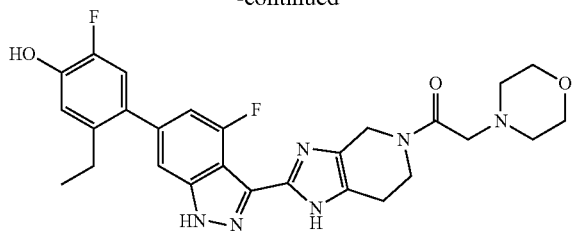

1

N,N-diisopropylethylamine (0.298 mL, 1.707 mmol) was added to a solution of 5-ethyl-2-fluoro-4-(4-fluoro-3-(4,5,6,7-tetrahydro-1H-imidazo[4,5-c]pyridin-2-yl)-1H-indazol-6-yl)phenol (135 mg, 0.341 mmol) (6), HATU (156 mg, 0.410 mmol) and 2-morpholinoacetic acid (7") (54.5 mg, 0.376 mmol) in DMF (0.5 mL) and the reaction mixture was stirred at RT for 24 h. Lithium hydroxide (49.1 mg, 2.049 mmol) was added and the reaction mixture was stirred at 65° C. for 1 h, and concentrated in vacuo to yield a clear yellow liquid. The crude liquid was purified via preparatory HPLC to yield the TFA salt of the title compound (142 mg, 0.223 mmol, 65.3% yield) as a beige solid.

Example 5: Crystalline 1-(2-(6-(2-Ethyl-5-fluoro-4-hydroxyphenyl)-4-fluoro-1H-indazol-3-yl)-1,4,6,7-tetrahydro-5H-imidazo[4,5-c]pyridin-5-yl)-2-morpholinoethan-1-one (1) Form 2

The compound 1 of example 1 (2.5 g) was dissolved in DMSO (5 mL) at 60° C. Once a homogenous solution was obtained, MeOH (2.5 mL) was added to the solution. The homogenous mixture was added dropwise over 30 min to a premixed solution of MeOH (12.75 mL) and H$_2$O (11.25 mL) at 75° C. Once the mixture had been fully added, the combined mixture was allowed to stir at 75° C. for 1 h while a crystalline slurry formed. H$_2$O (36 mL) was added dropwise over 2 h at 75° C. After the H$_2$O charge was complete, the slurry was stirred at 75° C. for 1 h, then slowly cooled to 20° C. over 6 h. The slurry was held at 20° C. for an additional 10 h before being filtered, washed with 70% H$_2$O/MeOH (10 mL), dried at 50° C. under vacuum for 18 h to provide the title compound Form 2 (2.13 g).

Properties of the Solid Forms of the Invention

Samples of the two anhydrous forms, Form 1 and Form 2 of 1-(2-(6-(2-Ethyl-5-fluoro-4-hydroxyphenyl)-4-fluoro-1H-indazol-3-yl)-1,4,6,7-tetrahydro-5H-imidazo[4, 5-c]pyridin-5-yl)-2-morpholinoethan-1-one (1) of Examples 2 and 5, respectively, were analyzed by powder X-ray diffraction (PXRD), differential scanning calorimetry (DSC), thermogravimetric analysis (TGA), dynamic moisture sorption (DMS), and polarized light microscopy image. Form 2 was also analyzed by single crystal x-ray diffraction.

Example 6: Powder X-Ray Diffraction

Figure 6:
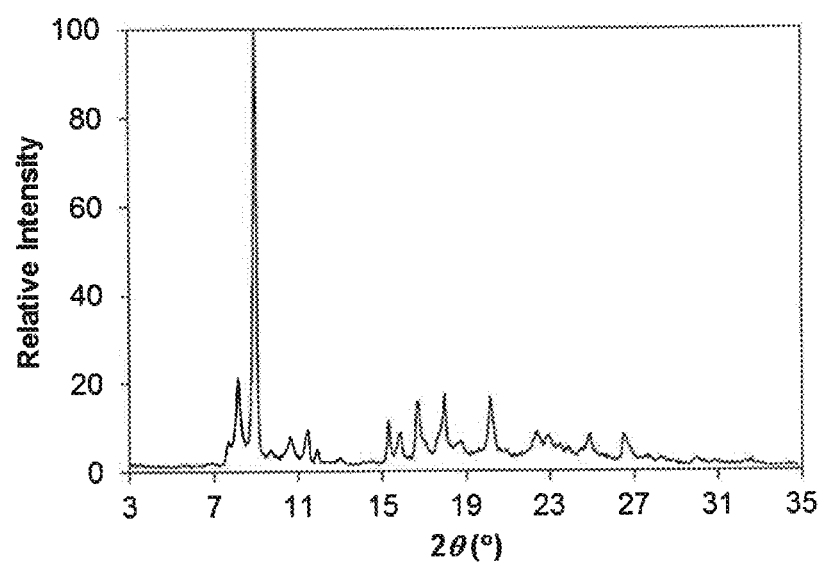
FIG. 6 shows a powder x-ray diffraction (PXRD) pattern of crystalline Form 1 of compound 1 (hereinafter Form 1).

The powder X-ray diffraction patterns of FIGS. 1 and 6 were obtained with a Bruker D8-Advance X-ray diffractometer using Cu-Kα radiation (λ=1.54051 Å) with output voltage of 45 kV and current of 40 mA. The instrument was operated in Bragg-Brentano geometry with incident, divergence, and scattering slits set to maximize the intensity at the sample. For measurement, a small amount of powder (5-25 mg) was gently pressed onto a sample holder to form a smooth surface and subjected to X-ray exposure. The samples were scanned in 2θ-2θ mode from 2° to 35° in 2θ with a step size of 0.020 and a scan speed of 0.30° seconds per step. The data acquisition was controlled by Bruker DiffracSuite measurement software and analyzed by Jade software (version 7.5.1). The instrument was calibrated with a corundum standard, within ±0.02° two-theta angle. Observed PXRD two-theta peak positions and d-spacings are shown in Tables 1 and 2, respectively for crystalline Form 1 and the crystalline Form 2.

TABLE 1

PXRD Data for Crystalline Form 1

| 2-Theta | d (Å) | Area | A % |
| --- | --- | --- | --- |
| 7.69 | 11.49 | 5570 | 7.30 |
| 8.16 | 10.83 | 36847 | 48.60 |
| 8.97 | 9.85 | 75877 | 100.00 |
| 10.66 | 8.29 | 7323 | 9.70 |
| 11.46 | 7.72 | 5841 | 7.70 |
| 11.91 | 7.43 | 1496 | 2.00 |
| 15.29 | 5.79 | 7115 | 9.40 |
| 15.80 | 5.60 | 7841 | 10.30 |
| 16.70 | 5.31 | 14679 | 19.30 |
| 17.02 | 5.20 | 8024 | 10.60 |
| 18.00 | 4.92 | 17834 | 23.50 |
| 18.83 | 4.71 | 2658 | 3.50 |
| 20.18 | 4.40 | 18636 | 24.60 |
| 22.39 | 3.97 | 7067 | 9.30 |
| 22.98 | 3.87 | 9029 | 11.90 |
| 24.89 | 3.57 | 8561 | 11.30 |
| 26.54 | 3.36 | 7831 | 10.30 |

TABLE 2

PXRD Data for the Crystalline Form 2

| 2-Theta | d (Å) | Area | A % |
| --- | --- | --- | --- |
| 10.61 | 8.33 | 706299 | 100.00 |
| 10.85 | 8.15 | 192921 | 27.30 |
| 11.84 | 7.47 | 487816 | 69.10 |
| 13.32 | 6.64 | 97980 | 13.90 |
| 14.94 | 5.93 | 519386 | 73.50 |
| 16.14 | 5.49 | 110314 | 15.60 |
| 16.35 | 5.42 | 75483 | 10.70 |
| 17.69 | 5.01 | 197341 | 27.90 |
| 18.26 | 4.85 | 445270 | 63.00 |
| 18.43 | 4.81 | 152845 | 21.60 |
| 19.06 | 4.65 | 564088 | 79.90 |
| 19.20 | 4.62 | 427174 | 60.50 |
| 19.49 | 4.55 | 266328 | 37.70 |
| 20.72 | 4.28 | 72244 | 10.20 |
| 21.10 | 4.21 | 236517 | 33.50 |
| 21.94 | 4.05 | 287485 | 40.70 |
| 22.64 | 3.93 | 121406 | 17.20 |
| 23.64 | 3.76 | 152841 | 21.60 |
| 25.19 | 3.53 | 68220 | 9.70 |
| 28.08 | 3.17 | 139597 | 19.80 |

Example 7: Thermal Analysis

Differential scanning calorimetry (DSC) was performed using a TA Instruments Model Q-100 module with a Thermal Analyst controller. Data were collected and analyzed using TA Instruments Thermal Analysis software. A sample of each crystalline form was accurately weighed into a covered aluminum pan. After a 5 minute isothermal equilibration period at 5° C., the sample was heated using a linear heating ramp of 10° C./min from 0° C. to 300° C.

Figure 7:
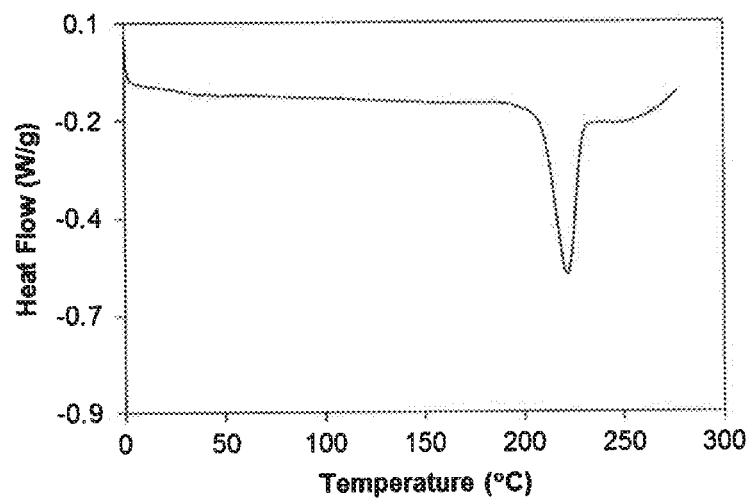
FIG. 7 shows a differential scanning calorimetry (DSC) thermogram of crystalline Form 1.
Figure 8:
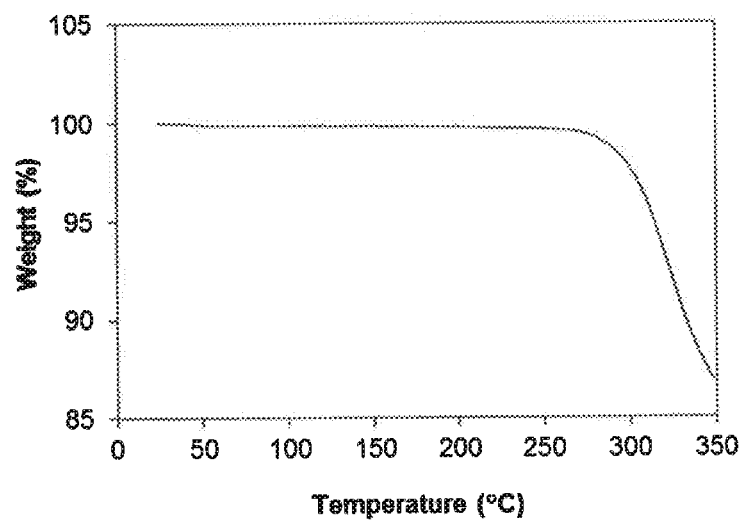
FIG. 8 shows a thermal gravimetric analysis (TGA) plot of crystalline Form 1.

A representative DSC thermogram of the Form 1 crystalline free form of the invention is shown in FIG. 7. The differential scanning calorimetry (DSC) trace recorded at a heating rate of 10° C. per minute exhibits a peak in endothermic heat flow, identified as a melt transition, in the range of about 210° C. to about 234° C., or in the range of between about 215° C. to about 229° C., or in the range of between about 220° C. to about 224° C. The crystalline form is characterized by a differential scanning calorimetry trace recorded at a heating rate of 10° C. per minute which shows a maximum in endothermic heat flow with a peak at about 221.7° C., or at 221.7±3° C.

Figure 2:
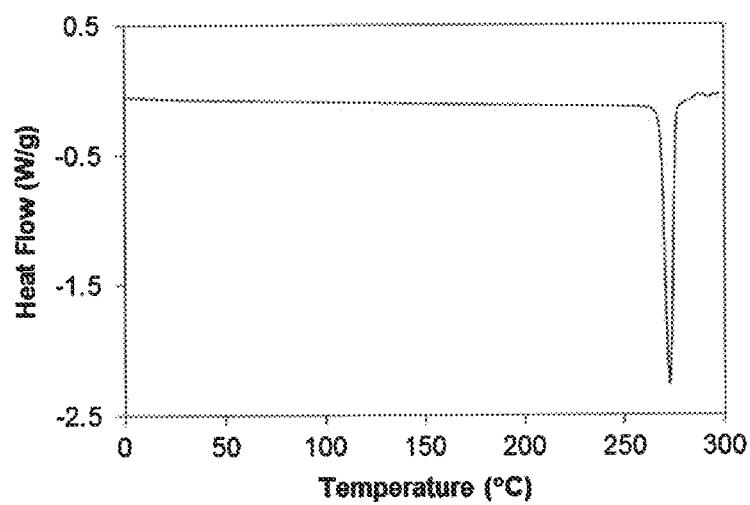
FIG. 2 shows a differential scanning calorimetry (DSC) thermogram of crystalline Form 2.

A representative DSC thermogram of the Form 2 crystalline free form of the invention is shown in FIG. 2. The differential scanning calorimetry (DSC) trace recorded at a heating rate of 10° C. per minute exhibits a peak in endothermic heat flow, identified as a melt transition, in the range of about 268° C. to about 277° C., or in the range of between about 270° C. to about 275° C., or in the range of between about 271° C. to about 274° C. The crystalline form is characterized by a differential scanning calorimetry trace recorded at a heating rate of 10° C. per minute which shows a maximum in endothermic heat flow with a peak at about 272.6° C., or at 272.6±2° C.

Thermogravimetric analysis (TGA) measurements were performed using a TA Instruments Model Q-50 module equipped with high resolution capability. Data were collected using TA Instruments Thermal Analyst controller and analyzed using TA Instruments Universal Analysis software. A weighed sample was placed onto a platinum pan and scanned with a heating rate of 10° C. from ambient temperature to 300-350° C. The balance and furnace chambers were purged with nitrogen flow during use.

A representative TGA trace of the Form 1 crystalline free form of the invention is shown in FIG. 8. The thermal gravimetric analysis (TGA) trace of FIG. 8 shows no significant weight loss at temperatures below the onset of decomposition at about 293° C.

A representative TGA trace of the Form 2 crystalline free form of the invention is shown in FIG. 3. The thermal gravimetric analysis (TGA) trace of FIG. 3 shows no significant weight loss at temperatures below the onset of decomposition at about 269° C.

Example 8: Dynamic Moisture Sorption Assessment

Dynamic moisture sorption (DMS) measurement was performed using a VTI atmospheric microbalance, SGA-100 system (VTI Corp., Hialeah, Fla. 33016). A weighed sample was used and the humidity was lowest possible value (close to 0% RH) at the start of the analysis. The DMS analysis consisted of an initial drying step (0% RH) for 120 minutes, followed by two cycles of sorption and desorption with a scan rate of 5% RH/step over the humidity range of 5% RH to 90% RH. The DMS run was performed isothermally at 25° C.

A representative DMS trace for the Form 1 crystalline free form of the invention is shown in FIG. 9.

Crystalline Form 1 demonstrated a small hysteresis between two cycles of sorption and desorption. Form 1 demonstrated about 0.99% weight gain in the humidity range of 5% to 70% relative humidity and about 1.32% weight gain in the humidity range of 5% to 90% relative humidity at room temperature, as shown in FIG. 9. Form 1 is considered to be slightly-hygroscopic.

A representative DMS trace for the Form 2 crystalline free form of the invention is shown in FIG. 4. Crystalline Form 2 showed no hysteresis between two cycles of sorption and desorption and demonstrated an exceptionally small propensity for hygroscopicity. Form 2 demonstrated about 0.12% weight gain in the humidity range of 5% to 70% relative humidity and about 0.18° % weight gain in the humidity range of 5% to 90% relative humidity at room temperature, as shown in FIG. 4. Form 2 is considered to be non-hygroscopic.

Example 9: Single Crystal X-Ray Diffraction of Form 2

Data were collected on a Rigaku Oxford Diffraction Supernova Dual Source, Cu at Zero, Atlas CCD diffractometer equipped with an Oxford Cryosystems Cobra cooling device. The data were collected using Cu Kα radiation. The structure was solved and refined using the Bruker AXS SHELXTL suite crystallographic software. Full details can be found in the CIF. Unless otherwise stated, hydrogen atoms attached to carbon were placed geometrically and allowed to refine with a riding isotropic displacement parameter. Hydrogen atoms attached to the heteroatoms were located in a difference Fourier map and were allowed to refine freely with an isotropic displacement parameter.

TABLE 3

Data from Single Crystal X-ray Diffraction Analysis for Form 2

| | |
|---|---|
| Empirical formula | $C_{27}H_{28}F_2N_6O_3$ |
| Formula weight | 522.55 |
| Crystal size | 0.14 × 0.10 × 0.02 mm$^3$ |
| Temperature of Data Collection | 293(2) K |
| Wavelength used for Data Collection | 1.54178 Å |
| Crystal system | Orthorhombic |
| Space group | Pbca |
| Unit cell dimensions | a = 9.7245(11) Å |
| | b = 16.8197(14) Å |
| | c = 32.604(4) Å |
| | α = 90° |
| | β = 90° |
| | γ = 90° |
| Unit cell volume | 5332.8(10) Å$^3$ |
| Z (Number of molecules in the unit cell) | 8 |
| Density (calculated) | 1.302 g/cm$^3$ |
| Theta range for data collection | 5.26-66.60° |
| Index ranges | −11 ≤ h ≤ 11 |
| | −12 ≤ k ≤ 20 |
| | −38 ≤ l ≤ 38 |
| Reflections collected | 24516 |
| Independent reflections | 4708 [$R_{int}$ = 0.0927] |
| Final R indices [F2 > 2sigma(F2)] | R1 = 0.0808, wR2 = 0.2159 |
| R indices (all data) | R1 = 0.1452, wR2 = 0.2859 |

Example 10: Solid State Stability Assessment of Form 1

Samples of the Form 1 crystalline free form of the invention were stored at 25° C. and 60% relative humidity (RH) and at 40° C. and 75% RH under two configurations a) open glass vial and b) closed glass vial placed inside an HDPE bottle containing desiccant. HDPE bottle was induction sealed. At specific intervals, the contents of a representative sample were removed and analyzed by HPLC for chemical purity (shown below as HPLC Purity (% a/a)).

TABLE 4

Crystalline Form 1 Stability Study

| | Condition | | | |
|---|---|---|---|---|
| Time Point (weeks) | 40° C./ 75% RH Closed With Desiccant | 40° C./ 75% RH Open | 25° C/ 60% RH Closed With Desiccant | 25° C./ 60% RH Open |
| 0 | | | 98.73 | |
| 2 | NT | 98.72 | NT | NT |
| 4 | 98.75 | 98.70 | 98.75 | 98.75 |
| 8 | 98.80 | 98.97 | 98.87 | 98.75 |
| 24 | 99.06 | 98.89 | 99.02 | 98.78 |
| 36 | 98.86 | 98.71 | 98.80 | 98.75 |

NT: Not Tested

Example 11: Polarized Light Microscopy (PLM) Image of Form 1 and Form 2

Samples of Form 1 and Form 2 were examined under an optical microscope (Olympus BX51) with cross-polarized light filter. Images were collected with a PaxCam camera controlled by PaxIt Imaging Software (version 6.4). Samples were prepared on glass slides with light mineral oil as immersion medium. Depending on the size of the particles, a 4×, a 10× or a 20× objective lens was used for magnification.

Preparation 8: tert-butyl 2-iodo-1-((2-(trimethylsilyl)ethoxy)methyl)-1,4,6,7-tetrahydro-5H-imidazo[4,5-c]pyridine-5-carboxylate (C-5)

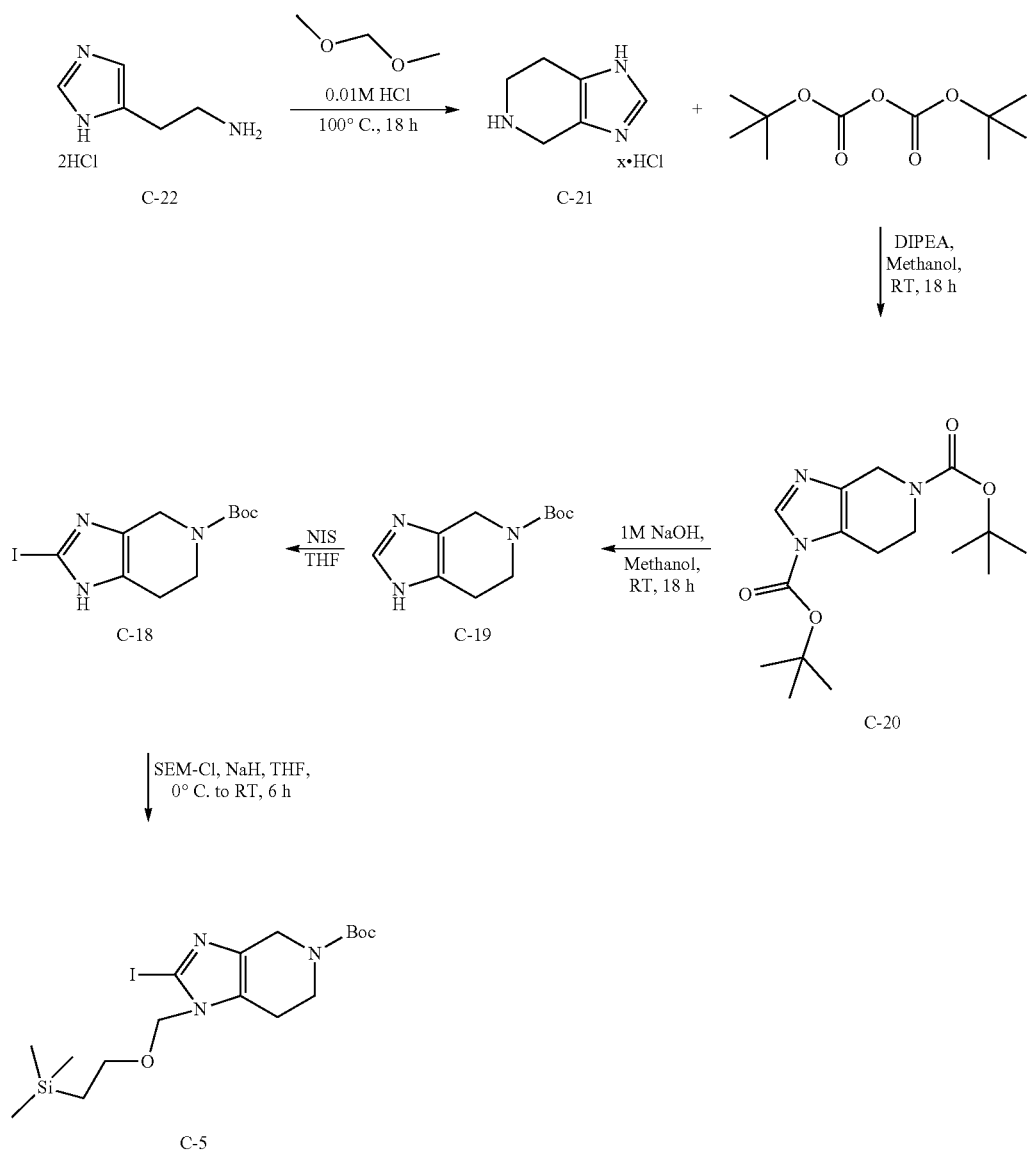

To a solution of compound C-22 (25 g, 135.86 mmol) in 0.01M HCl (500 mL) was added dimethoxymethane (21.64 mL, 244.54 mmol). The resulting solution was stirred at 100° C. for 18 h. The solvent was removed under vacuum and the residue was triturated twice with diethyl ether and ethanol, filtered and dried to provide compound C-21 (25.2 g, 94.6% yield).

To a solution of compound C-21 (25.0 g, 127.55 mmol) in methanol (250 mL) was added DIPEA (57.23 mL, 318.87 mmol) followed by addition of (Boc)$_2$O (68.23 mL, 318.87 mol) and the reaction was stirred at RT for 18 h. The resulting reaction was diluted with water (150 mL) and extracted using ethyl acetate (3×200 mL). The combined organic layer was dried over anhydrous sodium sulfate, decanted and concentrated under reduced pressure to obtain crude product C-20 which was taken forward to the next step without further purification.

To a solution of this crude compound C-20 (40.0 g, 123.8 mmol) in Methanol (500 mL) was added 1M NaOH Solution (200 mL) and resulting solution was stirred at RT for 18 h. The solvent was distilled off under vacuum and the resulting crude diluted with water (200 mL) and extracted using ethyl acetate (3×300 mL). The combined organic layer was dried over anhydrous sodium sulphate and concentrated under reduced pressure to obtain crude product which was purified through column chromatography (100-200 silica gel), eluted with 5-10% MeOH: DCM to get desired product C-19 (20 g, 72.4% yield).

To a solution of compound C-19 (20 g, 89.68 mmol) in THF (400 mL) was added NIS (30.26 g, 134.52 mmol) at RT and the resulting solution was stirred for 2 hours at the same temperature. The reaction mixture was diluted with water (200 mL) and extracted in ethyl acetate (2×300 mL), the organic layer was washed with a 10% sodium thiosulphate aqueous solution (3×100 mL) followed by brine, dried over anhydrous sodium sulphate and concentrated under reduced pressure to obtain crude product C-18 which was used in the next step without further purification.

To a stirred solution of compound C-18 (15.0 g, 42.97 mmol) in THF (150 mL) was added NaH (1.8 g 45.11 mmol) at 0° C. portionwise and the reaction mixture was stirred for 1 hour at RT. Then SEM chloride (8.18 mL, 45.11 mmol) was added drop-wise at 0° C. The reaction was stirred for 6 hours at RT. Progress of reaction was monitored by TLC, the reaction was quenched with ice water (200 mL) at 0° C. and extracted with ethyl acetate (2×200 mL). The combined organic layer was washed with brine and dried over anhydrous sodium sulphate. The organic layer was filtered and concentrated under reduced pressure to obtain crude product, which was purified by column chromatography (100-200) silica (eluted with 10-15% EtOAc: Hexane) to get the desired product C-5 as a viscous liquid (11 g, 55%).

Preparation 9: 2-(2-ethyl-5-fluoro-4-methoxyphenyl)-4,4,5,5-tetramethyl-1,3,2-dioxaborolane (C-12)

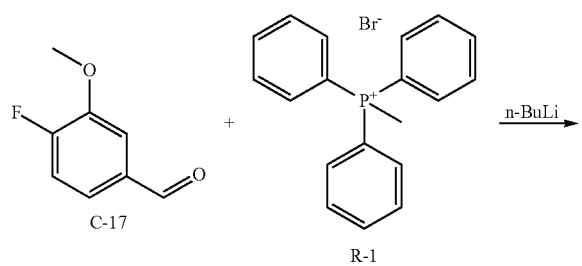

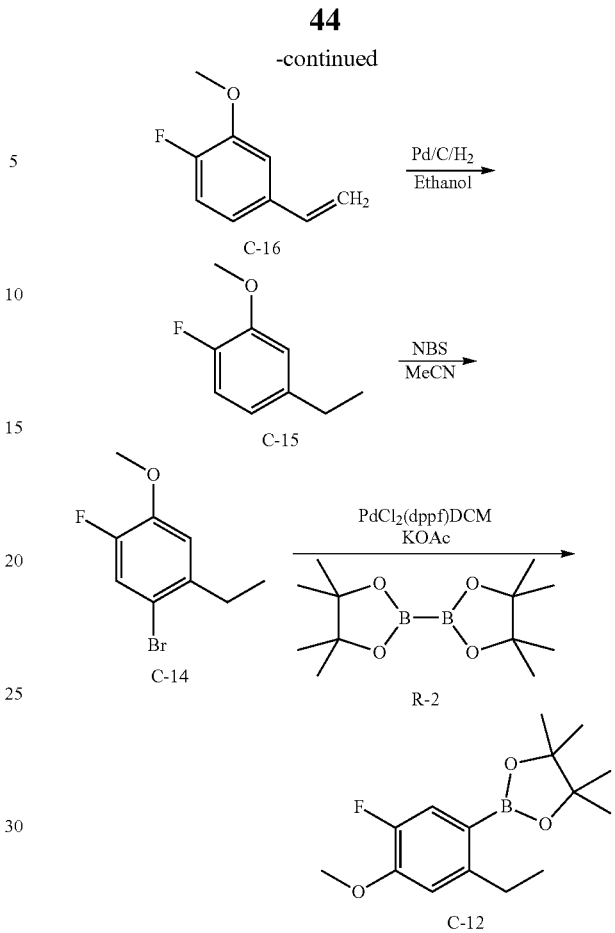

To a stirred suspension of compound C-17 (347.6 g, 973.14 mmol) in anhydrous THF (1000 mL) cooled to −40° C., was added n-Butyl lithium (2.5 M in hexane, 362.6 mL, 905.02 mmol) over 50 min, at which point the characteristic yellow color of the phosphorus ylide persisted. The reaction mixture was warmed to −10° C. and stirred for 1 h then the mixture was cooled to −30° C. and a solution of compound R-1 (50 g, 324.38 mmol) in anhydrous THF (200 mL) was added over 30 min. The resultant mixture was warmed to ambient temperature and stirred overnight. Progress of the reaction was monitored by TLC. On completion, the reaction was quenched by gradual addition of water (500 mL) and extracted with diethyl ether (3×500 mL). The combined organic layer was washed with water (2×500 mL), brine (250 mL), dried over (anhydrous Na$_2$SO$_4$) and concentrated under reduced pressure to give crude compound. The obtained crude product C-16 was used in the next step without purification.

To a solution crude C-16 (110 g, 723.39 mmol) in ethanol (1000 mL) was added 10% Pd/C (50 g). A balloon of hydrogen gas was mounted and the reaction was evacuated and back-filled with hydrogen three times. The reaction was stirred under a hydrogen atmosphere overnight at room temperature. After stirring at RT overnight, the reaction was complete. It was filtered through a pad of Celite and concentrated in vacuo to provide crude compound, which was purified through column chromatography (100-200) silica gel, eluted using 3-5% ethyl acetate/hexane to obtain the desired product C-15 as colorless liquid (24 g, 48% over the 2 steps).

To a solution of compound C-15 (24.0 g, 155.84 mmol) in MeCN (200 mL) was added a solution of NBS (28.0 g, 157.40 mmol) in MeCN (100 mL). The resulting solution was stirred at room temperature for 18 h. Solvent was removed in vacuo and the residue was diluted with diethyl ether (100 mL). Precipitation observed, which was removed by filtration and the filtrate was washed with sodium sulfite aqueous solution (200 mL) and brine (100 mL), dried over anhydrous sodium sulphate and concentrated in vacuo to give the desired product C-14 as yellow oil (35.0 g, 97% yield).

To a solution of compound C-14 (20 g, 85.836 mmol) in Dioxane (400 mL) were added compound R-2 (32.69 g, 128.755 mmol) and KOAc (25.27 g, 257.508 mmol). The reaction mixture was degassed with nitrogen for 15 minutes then palladium catalyst (3.5 g, 4.29 mmol) was added. The reaction mixture was stirred and heated at 110° C. for 3 hours. The reaction was filtered through a pad of Celite and washed with ethyl acetate. The filtrate was diluted with ethyl acetate (200 mL) and washed with water (2×200 mL)) and brine (100 mL), dried over sodium sulphate and concentrated under vacuum. The crude product obtained was purified through column chromatography (100-200 silica gel), eluted with 3-5% EtOAc: Hexane to give the desired product C-12 (20 g, 83% yield).

Preparation 10: 3-(dimethyl-stannyl)-6-(2-ethyl-5-fluoro-4-methoxyphenyl)-1-(tetrahydro-2H-pyran-2-yl)-1H-indazole (C-6)

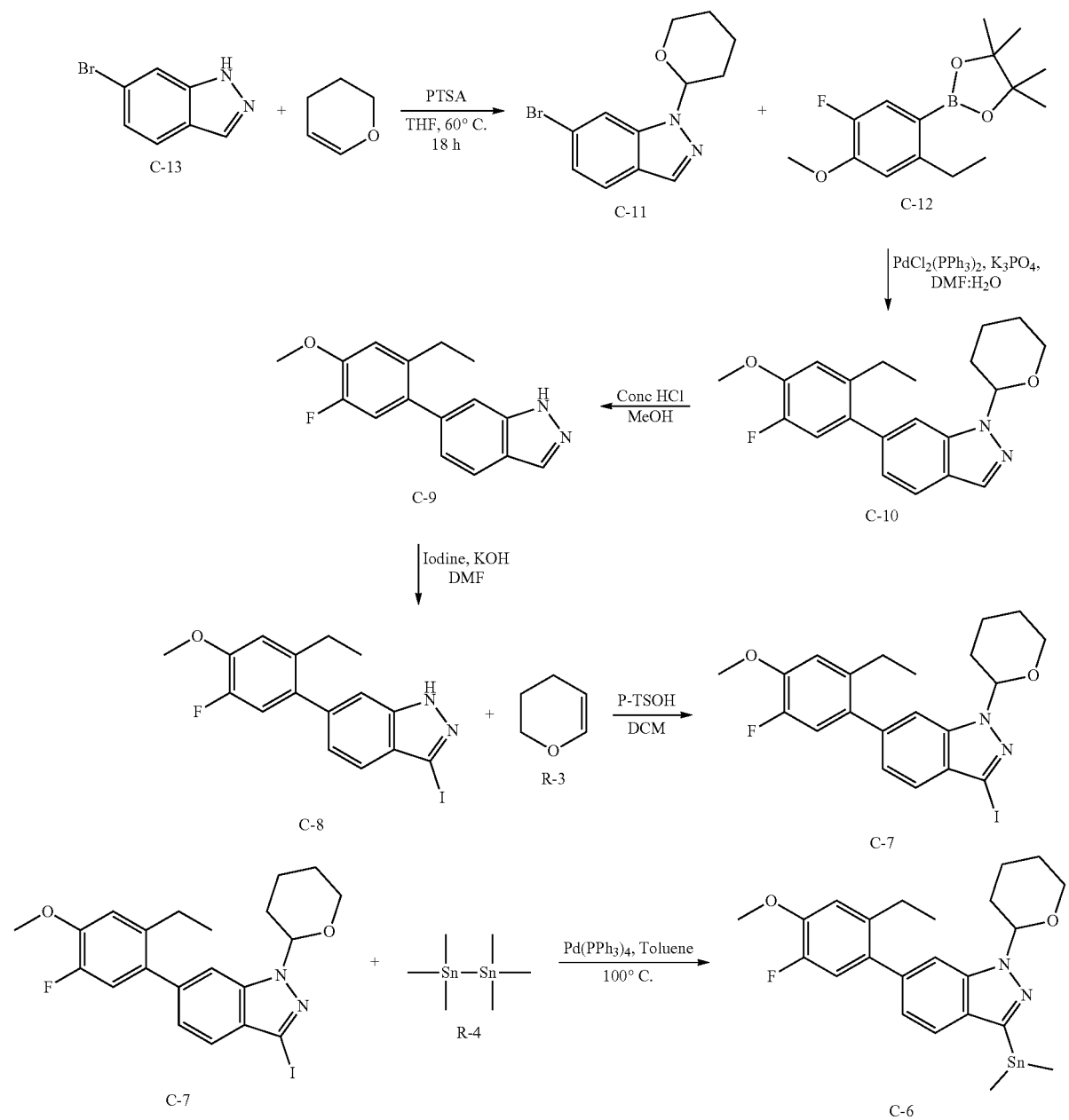

A mixture of compound C-13 (25 g, 126.84 mmol), 3,4-dihydro-2H-pyran (134.5 mL, 1471.5 mL) and p-TSA (5.57 g, 29.18 mmol) was taken in THF (700 mL) and heated at 60° C. overnight. The reaction mixture was poured into ice water and the aqueous phase was extracted with ethyl acetate. The organic layer was dried over sodium sulfate and filtered. The filtrate was evaporated under reduced pressure and residue purified over silica gel (230-400) column (eluting with 1-2% ethyl acetate in hexane) to give desired compound C-11 (23.5 g, 67% yield).

A solution of compound C-11 (13.3 g, 47.5 mmol), compound C-12 (15.96 g, 57.0 mmol) and $K_3PO_4$ (30.21 g, 142.5 mmol) in $DMF:H_2O$ (396:99 mL) was degassed with nitrogen for 15 minutes then palladium catalyst (1.6 g, 2.37 mmol) was added and the reaction mixture was purged with nitrogen for 5 minutes. The resulting reaction mixture was heated at 100° C. for 12 h under continuous stirring. The reaction mixture was filtered through a pad of Celite and washed with ethyl acetate. The filtrate was diluted with ethyl acetate (200 mL), extracted with EtOAc (2×100 mL) and washed with cold water (100 mL) and brine (50 mL), dried over sodium sulphate and concentrated under vacuum to get crude product which was purified through flash chromatography (100-200 silica gel), eluted with 10% EtOAc:Hexane to give C-10 (14 g, 91.4% yield)).

To a solution of compound C-10 (52 g, 146.89 mmol) in methanol (600 mL) was added Concentrated HCl (50 mL) and the resulting solution was heated at 60° C. overnight. The reaction mixture was cooled to RT and concentrated under vacuum. The residue was diluted with EtOAc (200 mL) and washed with a saturated $NaHCO_3$ aqueous solution (2×150 mL). The organic layer was dried over $Na_2SO_4$ and concentrated to get the desired product C-9 (35 g, 88.9% yield).

To a solution of C-9 (17.5 g, 64.81 mmol) in DMF (100 mL) was added KOH (14.5 g, 259.54 mmol) and the mixture was stirred for 15 minutes. A solution of iodine (32.7 g, 129.62 mmol) in DMF (50 mL) was added slowly at 0° C. and the reaction mixture was stirred at RT for 30 min. Progress of the reaction was monitored by TLC then the reaction mixture was diluted with water (200 mL) and extracted with ethyl acetate (2×200 mL). The organic layer was washed with saturated sodium metabisulfite aqueous solution (2×150 mL) and water (3×100 mL), dried over $Na_2SO_4$ and concentrated under vacuum to get crude product C-8 (21 g).

To a solution of C-8 (21.0 g, 53.02 mmol) in DCM (230 mL) was added p-TsOH (1.8 g, 10.60 mmol) and the mixture was cooled to 0° C. Compound R-3 (7.04 mL, 79.54 mmol) was added drop wise to the above solution and the reaction mixture was stirred at RT overnight. TLC monitoring showed completion of the reaction. The reaction mixture was diluted with DCM (2×150 mL) and washed with saturated $NaHCO_3$ aqueous solution (200 mL) and brine (200 mL). The organic layer was dried over anhydrous $Na_2SO_4$ and concentrated in vacuo to give crude product which was purified by flash chromatography to give C-7.

A solution of C-7 (10.0 g, 20.83 mmol) in Toluene (200 mL) was degassed with nitrogen for 20 minutes followed by addition of R-4 (4.89 mL, 22.91 mmol) and $Pd(PPh_3)_4$ (1.2 g, 1.04 mmol). The reaction mixture was purged with nitrogen for an additional 5 minutes and then stirred at 100° C. After 2 h, TLC shows completion of the reaction. The reaction mixture was cooled to room temperature, filtered through a Celite pad and the residue was washed with ethyl acetate. The concentrated filtrate was purified by column chromatography (neutral alumina), eluted with 2-5% EtOAc: Hexane to give product C-6 (6.4 g, 57.6% yield).

Preparation 11: 2-(6-(2-ethyl-5-fluoro-4-methoxyphenyl)-1H-indazol-3-yl)-4,5,6,7-tetrahydro-1H-imidazo[4,5-c]pyridine (C-3)

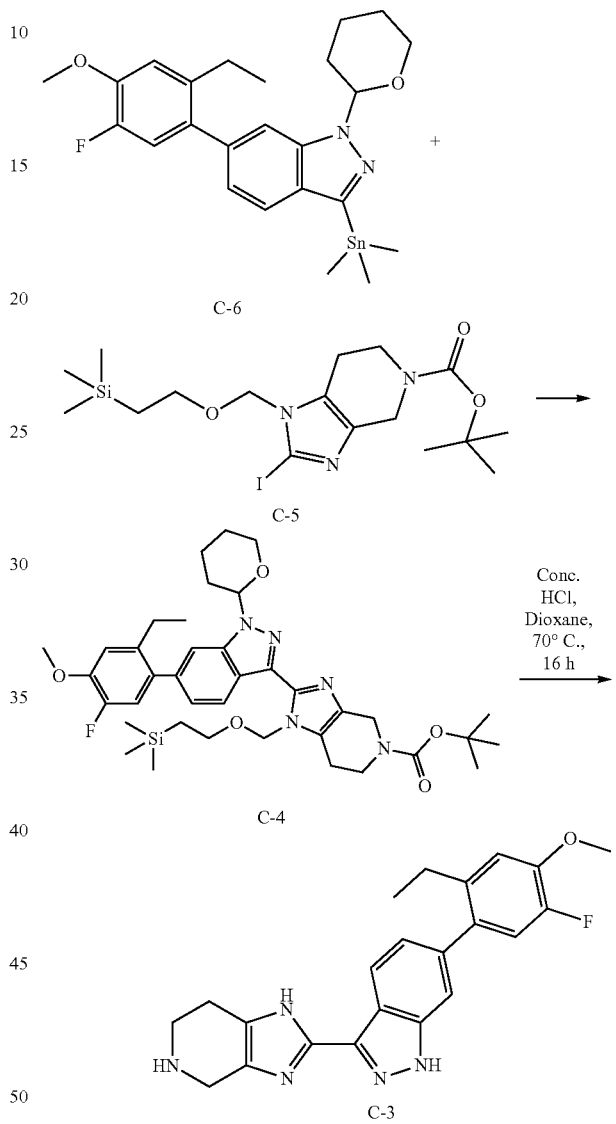

To a solution of compound C-6 (6.4 g, 12.37 mmol) in Toluene (100 mL) was added Compound C-5 (5.9 g, 12.37 mmol). The reaction mixture was degassed with nitrogen for 20 minutes, followed by addition of copper (I) iodide (470 mg, 2.47 mmol) and $Pd(PPh_3)_4$ (714 mg, 1.237 mmol) then stirred at 100° C. for 12 h. Progress of the reaction was monitored by TLC. The reaction was cooled to RT and filtered through a Celite pad, the residue was washed with ethyl acetate. The organic layer was diluted with water, separated and the organic part was washed with brine, dried over $Na_2SO_4$ and filtered. The filtrate was concentrated under reduced pressure to give crude product which was purified by column chromatography (100-200 mesh size silica), eluted with 20%, EtOAc: Hexane to give C-4 (4 g, 45.90/%).

To a solution of compound C-4 (4.0 g, 5.6 mmol) in Dioxane (30 mL) was added concentrated HCl (30 mL). The reaction mixture was stirred at 70° C. for 16 h. Progress of the reaction was monitored by LCMS. The reaction was cooled to RT, concentrated in vacuo, triturated with diethyl ether and purified through prep HPLC to give the desired compound C-3 (0.65 g, 29.5%).

Example 12: 1-(2-(6-(2-Ethyl-5-fluoro-4-hydroxyphenyl)-1H-indazol-3-yl)-1,4,6,7-tetrahydro-5H-imidazo[4,5-c]pyridin-5-yl)-2-morpholinoethan-1-one (C-1)

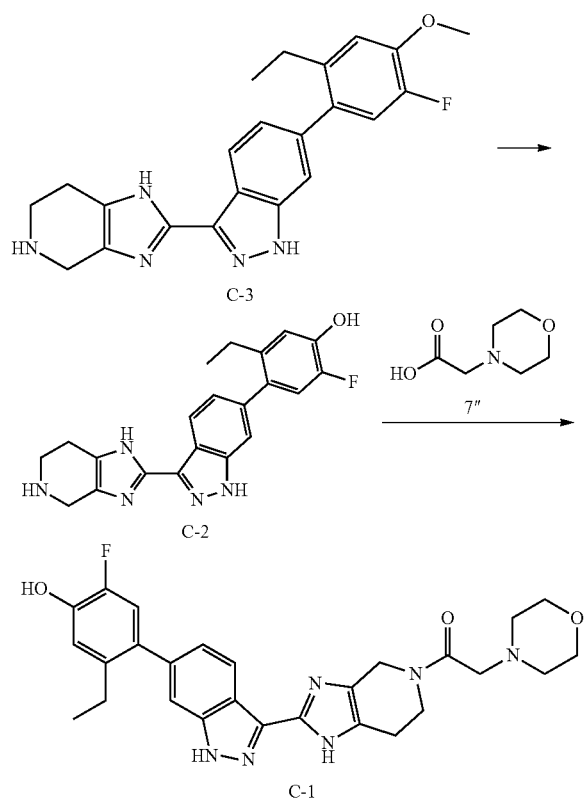

To the mixture of C-3 (180 mg, 0.460 mmol) in DCM (0.5 ml) at rt was added boron tribromide, 1 m in DCM [100 ml] (2.299 ml, 2.299 mmol). The resulting mixture was stirred for 30 mins before it was concentrated. The resulting residue was co-evaporated with MeOH (3×3.0 mL), re-dissolved in 1:1 mixture of AcOH:H$_2$O (3.0 mL), filtered and purified by reverse phase prep HPLC. Desired fractions were combined and frozen dried to give C-2 ((5-ethyl-2-fluoro-4-(3-(4,5,6,7-tetrahydro-1H-imidazo[4,5-c]pyridin-2-yl)-1H-indazol-6-yl)phenol) as a TFA salt.

To the mixture of C-2, TFA (15 mg, 0.031 mmol) and 7" (2 equivalents, 0.061 mmol) in DMF (0.5 ml) at rt was added HATU (25.5 mg, 0.067 mmol) and DIEA (0.043 ml, 0.244 mmol). The resulting mixture was stirred at rt overnight. The reaction was diluted with MeOH (0.5000 ml) and water (0.500 ml). LiOH (2.193 mg, 0.092 mmol) was added. The resulting mixture was heated at 65° C. for 1 hr. The reaction was then concentrated, the resulting residue was treated with a mixture of DCM (0.500 ml) and TFA (0.500 ml) at rt for 30 mins, concentrated, re-dissolved in 1:1 mixture of AcOH:H$_2$O (1.5 mL), filtered and purified by reverse phase prep HPLC to give compound C-1 as a TFA salt. (m/z): [M+H]$^+$ calcd for C$_{27}$H$_{29}$FN$_6$O$_3$ 504.23 found 505.2.

Biological Assays

Compound 1 has been characterized in one or more of the following biological assays.

Assay 1: Biochemical JAK Kinase Assays

A panel of four LanthaScreen JAK biochemical assays (JAK1, 2, 3 and Tyk2) were carried in a common kinase reaction buffer (50 mM HEPES, pH 7.5, 0.01% Brij-35, 10 mM MgCl$_2$, and 1 mM EGTA). Recombinant GST-tagged JAK enzymes and a GFP-tagged STAT1 peptide substrate were obtained from Life Technologies.

Serially diluted compound was pre-incubated with each of the four JAK enzymes and the substrate in white 384-well microplates (Corning) at ambient temperature for 1 h. ATP was subsequently added to initiate the kinase reactions in 10 μL total volume, with 1% DMSO. The final enzyme concentrations for JAK1, 2, 3 and Tyk2 are 4.2 nM, 0.1 nM, 1 nM, and 0.25 nM respectively; the corresponding Km ATP concentrations used are 25 μM, 3 μM, 1.6 μM, and 10 μM; while the substrate concentration is 200 nM for all four assays. Kinase reactions were allowed to proceed for 1 hour at ambient temperature before a 10 μL preparation of EDTA (10 mM final concentration) and Tb-anti-pSTAT1 (pTyr701) antibody (Life Technologies, 2 nM final concentration) in TR-FRET dilution buffer (Life Technologies) was added. The plates were allowed to incubate at ambient temperature for 1 h before being read on the EnVision reader (Perkin Elmer). Emission ratio signals (520 nm/495 nm) were recorded and utilized to calculate the percent inhibition values based on DMSO and background controls.

For dose-response analysis, percent inhibition data were plotted vs. compound concentrations, and IC$_{50}$ values were determined from a 4-parameter robust fit model with the Prism software (GraphPad Software). Results were expressed as pIC$_{50}$ (negative logarithm of IC$_{50}$) and subsequently converted to pK$_i$ (negative logarithm of dissociation constant, Ki) using the Cheng-Prusoff equation.

Compound 1 exhibited the following enzyme potency.

TABLE 5

| JAK 1 pK$_i$ | JAK 2 pK$_i$ | JAK 3 pK$_i$ | Tyk2 Pk$_i$ |
|---|---|---|---|
| 10 | 10.6 | 9.7 | 8.7 |

Assay 2: Cellular JAK Potency Assay: Inhibition of IL-13

The AlphaScreen JAKI cellular potency assay was carried out by measuring interleukin-13 (IL-13, R&D Systems) induced STAT6 phosphorylation in BEAS-2B human lung epithelial cells (ATCC). The anti-STAT6 antibody (Cell Signaling Technologies) was conjugated to AlphaScreen acceptor beads (Perkin Elmer), while the anti-pSTAT6 (pTyr641) antibody (Cell Signaling Technologies) was biotinylated using EZ-Link Sulfo-NHS-Biotin (Thermo Scientific).

BEAS-2B cells were grown at 37° C. in a 5% CO$_2$ humidified incubator in 50% DMEM/50% F-12 medium (Life Technologies) supplemented with 10% FBS (Hyclone), 100 U/mL penicillin, 100 μg/mL streptomycin (Life Technologies), and 2 mM GlutaMAX (Life Technologies). On day 1 of the assay, cells were seeded at a 7,500 cells/well density in white poly-D-lysine-coated 384-well plates (Corning) with 25 μL medium, and were allowed to adhere overnight in the incubator. On day 2 of the assay, the medium was removed and replaced with 12 μL of assay buffer (Hank's Balanced Salt Solution/HBSS, 25 mM HEPES, and 1 mg/mL bovine serum albumin/BSA) containing dose-responses of test compounds. The compound was serially diluted in DMSO and then diluted another 1000-fold in media to bring the final DMSO concentration to 0.1%. Cells were incubated with test compounds at 37° C. for 1 h, and followed by the addition of 12 μl of pre-warmed IL-13 (80 ng/mL in assay buffer) for stimulation. After incubating at 37° C. for 30 min, the assay buffer (containing compound and IL-13) was removed, and 10 μL of cell lysis buffer (25 mM HEPES, 0.1% SDS, 1% NP-40, 5 mM $MgCl_2$, 1.3 mM EDTA, 1 mM EGTA, and supplement with Complete Ultra mini protease inhibitors and PhosSTOP from Roche Diagnostics). The plates were shaken at ambient temperature for 30 min before the addition of detection reagents. A mixture of biotin-anti-pSTAT6 and anti-STAT6 conjugated acceptor beads was added first and incubated at ambient temperature for 2 h, followed by the addition of streptavidin conjugated donor beads (Perkin Elmer). After a minimum of 2 h incubation, the assay plates were read on the EnVision plate reader. AlphaScreen luminescence signals were recorded and utilized to calculate the percent inhibition values based on DMSO and background controls.

For dose-response analysis, percent inhibition data were plotted vs. compound concentrations, and $IC_{50}$ values were determined from a 4-parameter robust fit model with the Prism software. Results may also be expressed as the negative logarithm of the $IC_{50}$ value, $pIC_{50}$. Compound 1 exhibited a $pIC_{50}$ value of 7.9 in this assay.

Assay 3: Cellular JAK Potency Assay: Inhibition of IL-2/Anti-CD3 Stimulated IFNγ in Human PBMCs The potency of the test compound for inhibition of interleukin-2 (IL-2)/anti-CD3 stimulated interferon gamma (IFNγ) was measured in human peripheral blood mononuclear cells (PBMCs) isolated from human whole blood (Stanford Blood Center). Because IL-2 signals through JAK, this assay provides a measure of JAK cellular potency.

(1) Human peripheral blood mononuclear cells (PBMC) were isolated from human whole blood of healthy donors using a ficoll gradient. Cells were cultured in a 37° C., 5% $CO_2$ humidified incubator in RPMI (Life Technologies) supplemented with 10% Heat Inactivated Fetal Bovine Serum (FBS, Life Technologies), 2 mM Glutamax (Life Technologies), 25 mM HEPES (Life Technologies) and 1× Pen/Strep (Life Technologies). Cells were seeded at 200,000 cells/well in media (50 μL) and cultured for 1 h. The compound was serially diluted in DMSO and then diluted another 500-fold (to a 2× final assay concentration) in media. The test compound dilutions (100 μL/well) were added to cells, and incubated at 37° C., 5% $CO_2$ for 1 h, followed by the addition of IL-2 (R&D Systems; final concentration 100 ng/mL) and anti-CD3 (BD Biosciences; final concentration 1 μg/mL) in pre-warmed assay media (50 μL) for 24 h.

(2) After cytokine stimulation, cells were centrifuged at 500 g for 5 min and supernatants removed and frozen at −80° C. To determine the inhibitory potency of test compounds in response to IL-2/anti-CD3, supernatant IFNγ concentrations were measured via ELISA (R&D Systems). $IC_{50}$ values were determined from analysis of the inhibition curves of concentration of IFNγ vs compound concentration. Data are expressed as $pIC_{50}$ (negative decadic logarithm $IC_{50}$) values. Compound 1 exhibited a $pIC_{50}$ value of about 6.7 in this assay.

Assay 4: Cellular JAK Potency Assay: Inhibition of IL-2 Stimulated pSTAT5 in CD4+ T Cells The potency of the test compound for inhibition of interleukin-2 (IL-2)/anti-CD3 stimulated STAT5 phosphorylation was measured in CD4-positive (CD4+) T cells in human peripheral blood mononuclear cells (PBMCs) isolated from human whole blood (Stanford Blood Center) using flow cytometry. Because IL-2 signals through JAK, this assay provides a measure of JAK cellular potency.

CD4+ T cells were identified using a phycoerythrobilin (PE) conjugated anti-CD4 antibody (Clone RPA-T4, BD Biosciences), while an Alexa Fluor 647 conjugated anti-pSTAT5 antibody (pY694, Clone 47, BD Biosciences) was used to detect STAT5 phosphorylation.

(1) The protocol of Assay 3 paragraph (1) was followed with the exception that the cytokine stimulation with IL-2/anti-CD3 was performed for 30 min instead of 24 h.

(2) After cytokine stimulation, cells were fixed with pre warmed fix solution (200 μL; BD Biosciences) for 10 min at 37° C., 5% $CO_2$, washed twice with DPBS buffer (1 mL, Life Technologies), and resuspended in ice cold Perm Buffer III (1000 μL, BD Biosciences) for 30 min at 4° C. Cells were washed twice with 2% FBS in DPBS (FACS buffer), and then resuspended in FACS buffer (100 μL) containing anti-CD4 PE (1:50 dilution) and anti-CD3 anti-CD3Alexa Fluor 647 (1:5 dilution) for 60 min at room temperature in the dark. After incubation, cells were washed twice in FACS buffer before being analyzed using a LSRII flow cytometer (BD Biosciences). To determine the inhibitory potency of the test compound in response to IL-2/anti-CD3, the median fluorescent intensity (MFI) of pSTAT5 was measured in CD4+ T cells. $IC_{50}$ values were determined from analysis of the inhibition curves of MFI vs compound concentration. Data are expressed as $pIC_{50}$ (negative decadic logarithm $IC_{50}$) values. Compound 1 exhibited a $pIC_{50}$ value of about 7.7 in this assay.

Assay 5: Cellular JAK Potency Assay: Inhibition of IL-6 Stimulated CCL2 (MCP-1) in Human PBMCs The potency of the test compound for inhibition of interleukin-6 (IL-6) stimulated CCL2 (MCP-1) production was measured in human peripheral blood mononuclear cells (PBMCs) isolated from human whole blood (Stanford Blood Center). Because IL-6 signals through JAK, this assay provides a distal measure of JAK cellular potency.

(1) The protocol of Assay 3 paragraph (1) was followed up to the incubation with test compounds. In the present assay, after test compounds were added to wells and incubated, IL-6 (R&D Systems; final concentration 10 ng/ml) in pre-warmed assay media (50 μL) was added.

(2) After cytokine stimulation for 48 h, cells were centrifuged at 500 g for 5 min and supernatants were removed and frozen at −80° C. To determine the inhibitory potency of the test compound in response to IL-6, supernatant CCL2 (MCP-1) concentrations were measured via ELISA (R&D Systems). $IC_{50}$ values were determined from analysis of the inhibition curves of concentration of CCL2/MCP-1 vs compound concentration. Data are expressed as $pIC_{50}$ (negative decadic logarithm $IC_{50}$) values. Compound 1 exhibited a $pIC_{50}$ value of about 6.4 in this assay.

Assay 6: Cellular JAK Potency Assay: Inhibition of IFNγ-Induced pSTAT1

The potency of the test compound for inhibition of interferon gamma (IFNγ) stimulated STAT1 phosphorylation was measured in CD14-positive (CD14+) monocytes derived from human whole blood (Stanford Blood Center) using flow cytometry. Because IFNγ signals through JAK, this assay provides a measure of JAK cellular potency.

Monocytes were identified using a fluorescein isothiocyanate (FITC) conjugated anti-CD14 antibody (Clone RM052, Beckman Coulter), and an Alexa Fluor 647 conjugated anti-pSTAT1 antibody (pY701, Clone 4a, BD Biosciences) was used to detect STAT1 phosphorylation.

Human peripheral blood mononuclear cells (PBMC) were isolated from human whole blood of healthy donors using a ficoll gradient. Cells were cultured in a 37° C., 5% $CO_2$ humidified incubator in RPMI (Life Technologies) supplemented with 10% Fetal Bovine Serum (FBS, Life Technologies), 2 mM Glutamax (Life Technologies), 25 mM HEPES (Life Technologies) and 1× Pen/Strep (Life Technologies). Cells were seeded at 250,000 cells/well in media (200 μL), cultured for 2 h and resuspended in assay media (50 μL) (RPMI supplemented with 0.1% bovine serum albumin (Sigma), 2 mM Glutamax, 25 mM HEPES and 1× Penstrep) containing various concentrations of test compounds. Compounds were serially diluted in DMSO and then diluted another 1000-fold in media to bring the final DMSO concentration to 0.1%. The test compound dilutions were incubated with cells at 37° C., 5% $CO_2$ for 1 h, followed by the addition of pre-warmed IFNγ (R&D Systems) in media (50 μL) at a final concentration of 0.6 ng/mL for 30 min. After cytokine stimulation, cells were fixed with pre-warmed fix solution (100 μL) (BD Biosciences) for 10 min at 37° C., 5% $CO_2$, washed twice with FACS buffer (1 mL) (1% BSA in PBS), resuspended in 1:10 anti-CD14 FITC:FACS buffer (100 μL), and incubated at 4° C. for 15 min. Cells were washed once, and then resuspended in ice cold Perm Buffer III (BD Biosciences) (100 μL) for 30 min at 4° C. Cells were washed twice with FACS buffer, and then resuspended in 1:10 anti-pSTAT1 Alexa Fluor 647:FACS buffer (100 μL) for 30 min at RT in the dark, washed twice in FACS buffer, and analyzed using a LSRII flow cytometer (BD Biosciences).

To determine the inhibitory potency of the test compound, the median fluorescent intensity (MFI) of pSTAT1 was measured in CD14+ monocytes. $IC_{50}$ values were determined from analysis of the inhibition curves of MFI vs compound concentration. Data are expressed as $pIC_{50}$ (negative decadic logarithm $IC_{50}$) values. Compound 1 exhibited a $pIC_{50}$ value of about 7.1 in this assay.

Assay 7: Ocular Pharmacokinetics in Rabbit Eyes

The objective of this assay was to determine the pharmacokinetics of a test compound in rabbit ocular tissues.

Solution Formulation 1-(2-(6-(2-ethyl-5-fluoro-4-hydroxyphenyl)-4-fluoro-1H-indazol-3-yl)-1,4,6,7-tetrahydro-5H-imidazo[4,5-c]pyridin-5-yl)-2-morpholinoethan-1-one (1), prepared in Example 2, was dissolved in 2% 2-hydroxypropyl-β-cyclodextrin to attain a target concentration of 1 mg/mL. Bilateral intravitreal injection (50 μL/eye) of the solution of test compound was administered to New Zealand white rabbits (50 μg/eye). The test compound concentration was measured in ocular tissues: vitreous, aqueous, retina/choroid and iris-ciliary body at pre-determined time points post injection (30 min, 4 h, 1 d, 3 d, 7 d, 14 d). Two rabbits (four eyes) were dosed for each time point. In the vitreous tissue, compound 1 exhibited a two-phase decrease in concentration characterized by an initial decrease in concentration with a half-life of approximately 9 hours and finally a terminal half-life of approximately 2 days. The compound was found to distribute quickly into the retinal and choroidal region as well and shows a similar pharmacokinetic profile as in the vitreous tissue.

Suspension Formulation

A suspension formulation was prepared by combining compound 1 of Example 2 (Form 1), with 0.5% hydroxypropyl methylcellulose (HPMC E5)+0.02% Tween 80 in normal saline to attain a target concentration of 5 mg/mL, 20 mg/mL and 80 mg/mL for the 0.25 mg/eye, 1 mg/eye and 4 mg/eye doses respectively. Bilateral intravitreal injection (50 μL/eye) of the suspension of test compound was administered to New Zealand white rabbits. The test compound concentration was measured in ocular tissues as in the solution formulation assay at 30 min, 4 h, 24 h, 72 h, 7 d, 14 d, 28 d, 56 d and 84 d post injection. For the 4 mg/eye dose group, an additional time point at 168 d post injection was also collected. All dose groups demonstrated measurable drug concentration in the eye up to the last time point tested in this study. Robust sustained exposure was observed for all doses at 12 weeks (84 d). Sustained exposure was observed at 24 weeks (84 d) for the 4 mg/eye does group. The compound showed a linear decrease in drug concentration in the vitreous tissue from 30 min to 24 weeks with a drug clearance rate of approximately 5 to 10 μg/mL/day. The clearance rate is consistent with the solubility of compound 1 in the vehicle and the ocular pharmacokinetic behavior in the solution formulation. All dose groups demonstrated measurable drug concentration in the eye up to the last time point tested in this study. Therefore, it is plausible that drug exposure is longer than that observed in this study. The drug concentration in plasma was measured and found to be at least 3 orders of magnitude lower than the concentration in vitreous tissue at all three concentrations.

A suspension formulation was prepared by combining compound 1 of Example 5 (Form 2), with 0.5% hydroxypropyl methylcellulose (HPMC E5)+0.02% Tween 80 in normal saline to attain a target concentration of 0.4 mg/mL, 1 mg/mL, 2 mg/mL and 20 mg/mL for the 0.02 mg/eye, 0.05 mg/eye, 0.1 mg/eye and 1 mg/eye doses respectively. Bilateral intravitreal injection (50 μL/eye) of the suspension of test compound was administered to Dutch Belted rabbits. The test compound concentration was measured in vitreous humor, aqueous humor, iris-ciliary body, retina, retinal pigment epithelial/choroidal cells and plasma at 30 min, 7 d, 14 d, 28 d, 42 d and 56 d post injection. The compound showed a very gradual decrease in drug concentration in the vitreous tissue from 30 min to the last time point tested (28 d for 0.02 mg/eye dose, 42 d for 0.05 mg/eye and 1 mg/eye doses and 56 d for the 0.1 mg/eye dose). All dose groups demonstrated measurable drug concentration in the eye up to the last time point tested in this study. Therefore, it is plausible that drug exposure is longer than that observed in this study. The drug concentration in plasma was measured and found to be at least 3 orders of magnitude lower than the concentration in vitreous tissue at all three concentrations. The 3 orders of magnitude correspond to a logarithmic scale (i.e. 1000 on a non-logarithmic scale).

Assay 8: Pharmacodynamic Assay: Inhibition of IL6-Induced pSTAT3 in Rats

The ability of a single intravitreal administration of test compound to inhibit IL-6 induced pSTAT3 was measured in rat retina/choroid homogenates.

A suspension formulation was prepared by combining compound 1 of Example 2, with 0.5% hydroxypropyl methylcellulose (HPMC E5 LV), 0.02% Tween 80, and 9 mg/mL sodium chloride in purified water to attain a target concentration of 10 mg/mL.

Female Lewis rats were intravitreally (IVT) dosed (5 μL per eye) with the suspension formulation. Three days later, IL-6 (Peprotech; 0.1 mg/mL; 5 μL per eye) or vehicle was intravitreally administered to induce pSTAT3. Ocular tissues were dissected one hour after the second IVT injection with IL-6. The retina/choroid tissues were homogenized and pSTAT3 levels were measured using an ELISA (Cell Signaling Technology). The percent inhibition of IL-6-induced pSTAT3 was calculated in comparison to the vehicle/vehicle and vehicle/IL-6 groups. Inhibition of greater than 100% reflects a reduction of pSTAT3 levels to below those observed in the vehicle/vehicle group.

With a 3 day pre-treatment prior to IL-6 challenge, a 50 μg dose of compound 1 administered by the suspension formulation inhibited IL-6-induced pSTAT3 by 116% in the retina/choroid tissues.

Assay 9: Pharmacodynamic Assay: Inhibition of IFNγ-Induced IP-10 in Rabbit Eyes

The ability of a single intravitreal administration of test compound to inhibit interferon-gamma (IFNγ) induced IP-10 protein levels was measured in rabbit vitreous and retina/choroid tissues.

A suspension formulation was prepared by combining compound 1 of Example 2 (Form 1), with 0.5% hydroxypropyl methylcellulose (HPMC E5), 0.02% Tween 80, and 9 mg/mL sodium chloride in purified water to attain a target concentration of 20 mg/mL.

Male, New Zealand White rabbits (Liveon Biolabs, India) were used for the studies. Animals were acclimated after arrival at the research facilities (Jubilant Biosys Ltd., India). Each rabbit was given a total of two intravitreal (IVT) injections with a total dose volume of 50 μL per eye. The first IVT injection (45 μL per eye) delivered 0.9 mg of test compound or vehicle. One week later, a second IVT injection (5 μL per eye) delivered IFNγ (1 μg/eye; stock solution 1 mg/mL; Kingfisher Biotech) or vehicle for the induction of IP-10. On the day of the injections, rabbits were anesthetized with an intramuscular injection of ketamine (35 mg/kg) and xylazine (5 mg/kg). Once deeply anesthetized, each eye was rinsed with sterile saline and IVT injections were performed using a 0.5 mL insulin syringe (50 units=0.5 mL) with a 31-gauge needle at the supra-nasal side of the both eyes by marking the position with a Braunstein fixed caliper (2¾") 3.5 mm from the rectus muscle and 4 mm from the limbus.

Tissues were collected 24 hours after the second IVT injection with IFNγ. Vitreous humor (VH) and retina/choroid tissues (R/C) were collected and homogenized, and IP-10 protein levels were measured using a rabbit CXCL10 (IP-10) ELISA kit (Kingfisher Biotech). The percent inhibition of IFNγ-induced IP-10 was calculated in comparison to the vehicle/vehicle and vehicle/IFNγ groups.

With a 1 week pre-treatment prior to the IFNγ challenge, the suspension formulation of compound 1 inhibited IFNγ-induced IP-10 by 81% and 80% in the vitreous humor and retina/choroid tissues, respectively. Similar efficacy was also observed with a 1 month pre-treatment prior to the IFNγ challenge.

Assay 10: Dermal Pharmacokinetics in Mouse and Mini-Pig Skin

The objective of this assay was to determine the epidermal, dermal and plasma pharmacokinetics of a test compound following a 24 hr exposure to intact mouse or mini-pig skin.

1-(2-(6-(2-Ethyl-5-fluoro-4-hydroxyphenyl)-4-fluoro-1H-indazol-3-yl)-1,4,6,7-tetrahydro-5H-imidazo[4,5-c]pyridin-5-yl)-2-morpholinoethan-1-one (1), was formulated to 0.5% (w/w) in cream or ointment as described, as Formulation A or Formulation B, respectively in Table 6.

Twenty-four hours prior to dosing the hair was shaved from the back of 25 g male Balb/c mice exposing an area at of least 6 cm² (about 10% of body surface) and, in a separate experiment, of 10 kg Gottingen mini-pigs exposing an area of at least 450 cm² (about 10% of body surface). At time zero, following isoflurane anesthesia, the test compound was applied to the back of mice or mini-pigs at a dose of 25 μL/cm². The skin was covered with an adhesive cover to prevent loss of compound to the cage or bedding.

Following 24 h exposure, the backs were gently washed with soap and water to remove non-absorbed drug and patted dry. Immediately following this washing, blood was drawn by cardiac puncture from the mice and via venipuncture from the mini-pigs. The outer skin (stratum corneum) was then removed by adhesive tape stripping. Upon exposure of the epidermis a 0.5 cm punch biopsy was taken. The epidermis and dermis were quickly separated, weighed and snap frozen. Similar samples were obtained at 48 h post dosing in mice and at 48 h, 94 h, and 168 h (7 days) post-dosing in mini-pigs.

Epidermis and dermis samples were homogenized in 1:10 (w/v) water using a Covaris ultrasonic homogenizer. Samples were extracted in 3 volumes of acetonitrile and quantified against a standard curve via LC-MS analysis. As evidenced by the pharmacokinetic parameters $AUC_{0-t}$ for plasma, epidermis and dermis shown in Table 7 below, significant compound exposure was exhibited in epidermis and dermis layers while the plasma exposure was negligible in mice in Formulation A and below the limit of quantitation in Formulation B in mice and in both formulations in mini-pig.

TABLE 6

| Formulation A | | Formulation B | |
|---|---|---|---|
| Compound 1 | 0.5% | Compound 1 | 0.5% |
| Stearic Acid | 5% | Octylhydroxystearate | 5% |
| Cetostearyl Alcohol | 5% | C8-C10 Triglyceride | 5% |
| Isopropyl Palmitate | 4% | Vaseline (Petrolatum) | 79.5% |
| Octylhydroxystearate | 2% | N-Methylpyrrolidone | 10% |
| BRIJ S2 (PEG 2 Stearyl Ether) | 1.08% | | |
| BRIJ S20 (PEG 20 Stearyl Ether) | 6.92% | | |
| N-Methylpyrrolidine | 10% | | |
| PEG400 | 10% | | |
| RO Water | 55.5% | | |

TABLE 7

| | Plasma $AUC_{0-t}$ (μg * hr/mL) | Epidermis $AUC_{0-t}$ (μg * hr/g) | Dermis $AUC_{0-t}$ (μg * hr/g) |
|---|---|---|---|
| Mouse Formulation A | 0.022 | 1370 | 99 |
| Mouse Formulation B | <0.001 | 10700 | 1110 |
| Mini-pig Formulation A | <0.001 | 1220 | 44 |
| Mini-pig Formulation B | <0.001 | 2460 | 88 |

Assay 11: Lung and Plasma Pharmacokinetics in Mice

Plasma and lung concentrations of compound 1 and ratios thereof were determined in the following manner. BALB/c mice from Charles River Laboratories were used in the assay. Compound 1 Form 1 of example 2 was formulated in 0.01% Tween 80 in normal saline (0.9% sodium chloride in water) at a concentration of 0.1 mg/mL as a suspension. 50 μL of the suspension formulation was introduced into the trachea of a mouse by oral aspiration. At various time points (0.083, 1, 4, 24, 48, 72, and 96 hr). Post dosing, blood samples were removed via cardiac puncture and intact lungs were excised from the mice. Blood samples were centrifuged (Eppendorf centrifuge, 5804R) for 4 minutes at approximately 12,000 rpm at 4° C. to collect plasma. Lungs were padded dry, weighed, and homogenized at a dilution of 1:3 in sterile water. Plasma and lung concentrations of compound 1 were determined by LC-MS analysis against analytical standards constructed into a standard curve in the test matrix. Good exposure in lungs was found with a lung AUC (0-96 hr) of 360 µg hr/g. The lung half-life was calculated at approximately 40 hours. The lung to plasma ratio was determined as the ratio of the lung AUC in µg hr/g to the plasma AUC in µg hr/mL (where AUC is conventionally defined as the area under the curve of test compound concentration vs. time). The lung to plasma AUC ratio was 1780, showing very low exposure in the plasma.

Assay 12: Pharmacodynamic Assay: Inhibition of IFNγ-Induced pSTAT1 in Rabbit Eyes The ability of a single intravitreal administration of test compound to inhibit interferon-gamma (IFNγ) induced phosphorylation of STAT1 protein (pSTAT1) was measured in rabbit retina/choroid tissue.

A suspension formulation was prepared by combining compound 1 of Example 2 (Form 1), with 0.5% hydroxypropyl methylcellulose (HPMC E5), 0.02% Tween 80, and 9 mg/mL sodium chloride in purified water to attain a target concentration of 20 mg/mL.

Male, New Zealand White rabbits (Liveon Biolabs, India) were used for the studies. Animals were acclimated after arrival at the research facilities (Jubilant Biosys Ltd., India). Each rabbit was given a total of two intravitreal (IVT) injections with a total dose volume of 50 µL per eye. The first IVT injection (45 µL per eye) delivered 0.9 mg of test compound or vehicle. One week later, a second IVT injection (5 µL per eye) delivered IFNγ (1 µg/eye stock solution 1 mg/mL Kingfisher Biotech) or vehicle for the induction of IP-10. On the day of the injections, rabbits were anesthetized with an intramuscular injection of ketamine (35 mg/kg) and xylazine (5 mg/kg). Once deeply anesthetized, each eye was rinsed with sterile saline and IVT injections were performed using a 0.5 mL insulin syringe (50 units=0.5 mL) with a 31-gauge needle at the supra-nasal side of the both eyes by marking the position with a Braunstein fixed caliper (2¾") 3.5 mm from the rectus muscle and 4 mm from the limbus.

Tissues were collected 2 hours after the second IVT injection with IFNγ. Retina/choroid tissues (R/C) were collected and homogenized, and pSTAT1 levels were measured by quantitative Western Blot on the ProteinSimple WES instrument. The percent inhibition of IFNγ-induced pSTAT1 was calculated in comparison to the vehicle/vehicle and vehicle/IFNγ groups.

With a 1 week pre-treatment prior to the IFNγ challenge, the suspension formulation of compound 1 inhibited IFNγ-induced pSTAT1 by 85%. After a 3 month pre-treatment with a single dose of the suspension formulation prior to the IFNγ challenge, the suspension formulation of compound 1 inhibited IFNγ-induced pSTAT1 by 76%.

A suspension formulation was prepared by combining compound 1 of Example 5 (Form 2), with 0.5% hydroxypropyl methylcellulose (HPMC E5)+0.02% Tween 80 in normal saline to attain a target concentration of 11.1, 3.3, and 1.1 mg/mL.

Male, New Zealand White rabbits (Liveon Biolabs, India) were used for the studies. Animals were acclimated after arrival at the research facilities (Jubilant Biosys Ltd., India). Each rabbit was given a total of two intravitreal (IVT) injections with a total dose volume of 50 µL per eye. The first IVT injection (45 µL per eye) delivered 500 µg, 150 µg, or 50 µg of test compound or vehicle. Two weeks later, a second IVT injection (5 µL per eye) delivered IFNγ (1 µg/eye; stock solution 1 mg/mL; Kingfisher Biotech) or vehicle for the induction of IP-10. On the day of the injections, rabbits were anesthetized with an intramuscular injection of ketamine (35 mg/kg) and xylazine (5 mg/kg). Once deeply anesthetized, each eye was rinsed with sterile saline and IVT injections were performed using a 0.5 mL insulin syringe (50 units=0.5 mL) with a 31-gauge needle at the supra-nasal side of the both eyes by marking the position with a Braunstein fixed caliper (2¾") 3.5 mm from the rectus muscle and 4 mm from the limbus.

Tissues were collected 2 hours after the second IVT injection with IFNγ. Retina/choroid tissues (R/C) were collected and homogenized, and pSTAT1 levels were measured by quantitative Western Blot on the ProteinSimple WES instrument. The percent inhibition of IFNγ-induced pSTAT1 was calculated in comparison to the vehicle/vehicle and vehicle/IFNγ groups.

With a 2 week pre-treatment prior to the IFNγ challenge, the suspension formulation of compound 1 inhibited IFNγ-induced pSTAT1 by 79%, for the 500 µg dose, by 58% for the 150 µg does and 61% for the 50 µg dose.

Assay 13: Kinome Screen and GINI Coefficient

Compounds 1 and C-1 were screened against other kinases to evaluate their selectivity profile.

Kinase-tagged T7 phage strains were grown in parallel in 24-well blocks in an E. coli host derived from the BL21 strain. E. coli were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 µm) to remove cell debris. The remaining kinases were produced in HEK-293 cells and subsequently tagged with DNA for qPCR detection.

Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 40× stocks in 100% DMSO and directly diluted into the assay. All reactions were performed in polypropylene 384-well plates in a final volume of 0.04 ml. The assay plates were incubated at room temperature with shaking for 1 hour and the affinity beads were washed with wash buffer (1×PBS, 0.05°% Tween 20). The beads were then re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR.

The compounds were screened at 1 µM, and results for primary screen binding interactions in Table 8 and 9 are reported as "% inhibition" (=100−((test compound signal−positive control signal)/((negative control signal)−(positive control signal))×100) where the negative control is DMSO and the positive control is a control compound.

TABLE 8

| Compound | ALK | AURKA | CDK2 | CDK7 | CDK9 | CSF1R | EPHB6 | GSK3B |
|---|---|---|---|---|---|---|---|---|
| 1 | 75 | 11 | 6 | 74 | 9 | 98 | 88 | 31 |
| C-1 | 81 | 57 | 53 | 99 | 95 | 100 | 98 | 68 |

TABLE 9

| Compound | KIT | PAK4 | PKAC-ALPHA | PLK4 | SLK | SRC | SYK | VEGFR2 |
|---|---|---|---|---|---|---|---|---|
| 1 | 87 | 93 | 20 | 58 | 100 | 93 | 46 | 42 |
| C-1 | 99 | 99 | 70 | 68 | 100 | 100 | 78 | 63 |

Compound 1 was found to exhibit significantly lower binding inhibition for CDK7 and CDK9 than compound C-1. Compound 1 also had lower binding inhibition for several other kinases.

Both compounds 1 and C-1 were screened against 35 different kinases. The Gini coefficient was determined for both compounds. Compound 1 had a GINI coefficient of 0.62 and compound C-1 had a GINI coefficient of 0.46. The Gini coefficient is used to express the selectivity of a compound against a panel of kinases (Graczyk, *J. Med. Chem.*, 2007, 50, 5773-5779). A higher number corresponds to a more selective compound.

The only structural difference between compound 1 and compound C-1 is the presence of a fluoro group on the core. This structural difference has been shown to have an important effect on the kinome selectivity of the compound.

Assay 14: Cytotoxicity Assay

A CellTiter-Glo luminescent cell viability/cytotoxicity assay was carried out in BEAS-2B human lung epithelial cells (ATCC) under the normal growth condition.

Cells were grown at 37° C. in a 5% $CO_2$ humidified incubator in 50% DMEM/50% F-12 medium (Life Technologies) supplemented with 10% FBS (Hyclone), 100 U/mL penicillin, 100 µg/mL streptomycin (Life Technologies), and 2 mM GlutaMAX (Life Technologies). On day 1 of the assay, cells were seeded at a 500 cells/well density in white 384-well tissue culture plates (Corning) with 25 µL medium, and were allowed to adhere overnight in the incubator. On day 2 of the assay, 5 µL of medium containing dose-responses of test compounds was added, and incubated at 37° C. for 48 h. 30 µL of CellTiter-Glo detection solution (Promega) was subsequently added, mixed on an orbital shaker for 5 min, and incubated for additional 10 min before being read on the EnVision reader. Luminescence signals were recorded and percent DMSO control values were calculated.

For dose-response analysis, percent DMSO control data were plotted vs. compound concentrations to derive dose-response curves by line connecting each data point. The concentration at which each curve crosses the 15% inhibition threshold is defined as $CC_{15}$.

It is expected that test compounds exhibiting a higher $CC_{15}$ value in this assay have less likelihood to cause cytotoxicity.

Compound 1 exhibited a $CC_{15}$ of 3.16 µM whereas compound C-1 exhibited a $CC_{15}$ of 630 nM. Therefore, compound 1 is significantly less likely to cause cytotoxicity than compound C-1 based on this assay.

The only structural difference between compound 1 and compound C-1 is the presence of a fluoro group on the core. This structural difference has been shown to have an important effect on the cytotoxicity of the compound.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A method of treating an ocular disease in a mammal, the method comprising administering a pharmaceutical composition comprising a compound of formula:

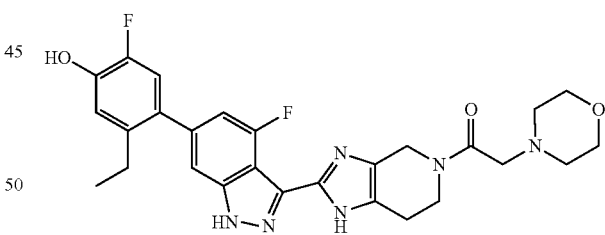

or a pharmaceutically-acceptable salt thereof, and a pharmaceutically-acceptable carrier to the eye of the mammal.

2. The method of claim 1, wherein the ocular disease is uveitis, diabetic retinopathy, diabetic macular edema, dry eye disease, age-related macular degeneration, retinal vein occlusion, or atopic keratoconjunctivitis.

3. The method of claim 2 wherein the ocular disease is uveitis.

4. The method of claim 2, wherein the ocular disease is diabetic macular edema.

5. The method of claim 1, wherein the pharmaceutical composition is administered by intravitreal injection.

6. The method of claim 5, wherein the pharmaceutical composition is a suspension.

7. A method of treating an ocular disease in a mammal, the method comprising administering to the eye of the mammal a pharmaceutical composition comprising a crystalline form of the compound of formula:

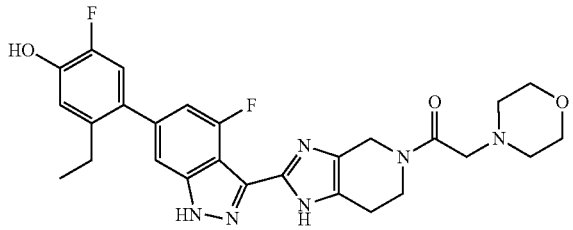

wherein the crystalline form is characterized by a powder X-ray diffraction pattern comprising diffraction peaks at 2θ values of 10.61±0.20, 11.84±0.20, 14.94±0.20, 18.26±0.20, and 19.06±0.20, and a pharmaceutically-acceptable carrier.

8. The method of claim 7, wherein the powder X-ray diffraction pattern is further characterized by having additional diffraction peaks at 2θ values of 13.32±0.20, 17.69±0.20, and 21.10±0.20.

9. The method of claim 7, wherein the powder X-ray diffraction pattern is further characterized by having two or more additional diffraction peaks at 2θ values selected from 10.85±0.20, 16.14±0.20, 16.35±0.20, 18.43±0.20, 19.20±0.20, 19.49±0.20, 20.72±0.20, 21.94±0.20, 22.64±0.20, 23.64±0.20, 25.19±0.20, and 28.08±0.20.

10. The method of claim 7, wherein the crystalline form is characterized by a powder X-ray diffraction pattern in which the peak positions are substantially in accordance with the peak positions of the pattern shown in FIG. 1.

11. The method of claim 7, wherein the crystalline form is characterized by a differential scanning calorimetry trace recorded at a heating rate of 10° C. per minute which shows a maximum in endothermic heat flow at a temperature between 268° C. and 277° C.

12. The method of claim 7, wherein the crystalline form is characterized by a differential scanning calorimetry trace substantially in accordance with that shown in FIG. 2.

13. The method of claim 7, wherein the ocular disease is uveitis, diabetic retinopathy, diabetic macular edema, dry eye disease, age-related macular degeneration, retinal vein occlusion, or atopic keratoconjunctivitis.

14. The method of claim 13 wherein the ocular disease is uveitis.

15. The method of claim 13 wherein the ocular disease is diabetic macular edema.

16. The method of claim 7, wherein the pharmaceutical composition is administered by intravitreal injection.

17. The method of claim 16, wherein the pharmaceutical composition is a suspension.

18. A method of treating an ocular disease in a mammal, the method comprising administering to the eye of the mammal a pharmaceutical composition comprising a crystalline form of the compound of formula:

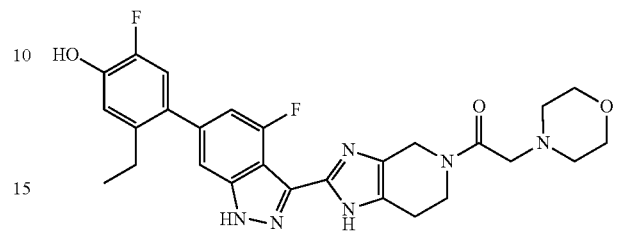

wherein the crystalline form is characterized by a powder X-ray diffraction pattern comprising diffraction peaks at 2θ values of 8.16±0.20, 8.97±0.20, 15.29±0.20, 16.70±0.20, 18.00±0.20, and 20.18±0.20, and a pharmaceutically-acceptable carrier.

19. The method of claim 18, wherein the powder X-ray diffraction pattern is further characterized by having two or more additional diffraction peaks at 2θ values selected from 7.69±0.20, 10.66±0.20, 11.46±0.20, 11.91±0.20, 15.80±0.20, 17.02±0.20, 18.83±0.20, 22.39±0.20, 22.98±0.20, 24.89±0.20, and 26.54±0.20.

20. The method of claim 18, wherein the crystalline form is characterized by a powder X-ray diffraction pattern in which the peak positions are substantially in accordance with the peak positions of the pattern shown in FIG. 6.

21. The method of claim 18, wherein the crystalline form is characterized by a differential scanning calorimetry trace recorded at a heating rate of 10° C. per minute which a maximum in endothermic heat flow at a temperature between 215° C. and 229° C.

22. The method of claim 18, wherein the crystalline form is characterized by a differential scanning calorimetry trace substantially in accordance with that shown in FIG. 7.

23. The method of claim 18, wherein the ocular disease is uveitis, diabetic retinopathy, diabetic macular edema, dry eye disease, age-related macular degeneration, retinal vein occlusion, or atopic keratoconjunctivitis.

24. The method of claim 23 wherein the ocular disease is uveitis.

25. The method of claim 23 wherein the ocular disease is diabetic macular edema.

26. The method of claim 18, wherein the pharmaceutical composition is administered by intravitreal injection.

27. The method of claim 26, wherein the pharmaceutical composition is a suspension.

* * * * *

UNITED STATES PATENT AND TRADEMARK OFFICE
CERTIFICATE OF CORRECTION

PATENT NO. : 11,160,810 B2
APPLICATION NO. : 16/656940
DATED : November 2, 2021
INVENTOR(S) : McKinnell et al.

Page 1 of 1

It is certified that error appears in the above-identified patent and that said Letters Patent is hereby corrected as shown below:

In the Claims

Claim 21, Column 62, Line 35, delete "which a" and insert -- which shows a --.

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*